(12) United States Patent
Zeller et al.

(10) Patent No.: US 7,700,522 B2
(45) Date of Patent: *Apr. 20, 2010

(54) α-OXYGENATED OR α-THIOLATED CARBOXYLIC ACID PHENETHYLAMIDE DERIVATIVES

(75) Inventors: Martin Zeller, Muenchwilen (CH); Clemens Lamberth, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 1467 days.

This patent is subject to a terminal disclaimer.

(21) Appl. No.: 10/495,256

(22) PCT Filed: Nov. 15, 2002

(86) PCT No.: PCT/EP02/12846

§ 371 (c)(1),
(2), (4) Date: May 7, 2004

(87) PCT Pub. No.: WO03/042168

PCT Pub. Date: May 22, 2003

(65) Prior Publication Data

US 2005/0038082 A1 Feb. 17, 2005

(30) Foreign Application Priority Data

Nov. 16, 2001 (GB) .................. 0127557.7

(51) Int. Cl.
A01N 37/18 (2006.01)
C07C 233/00 (2006.01)

(52) U.S. Cl. ........................ 504/336; 564/170

(58) Field of Classification Search ........... 504/336, 504/294, 289, 271, 266, 244, 236, 239, 235, 504/293, 247, 296, 298; 564/170; 549/493, 549/496, 366, 441, 469, 76; 548/247, 204; 546/336, 175; 544/241, 238, 334, 335, 400

See application file for complete search history.

(56) References Cited

FOREIGN PATENT DOCUMENTS

| JP | 05070428 | 3/1993 |
|----|----------|--------|
| WO | 9429267 | 12/1994 |
| WO | 9617840 | 6/1996 |
| WO | 9933810 | 7/1999 |
| WO | 0187822 | 11/2001 |

OTHER PUBLICATIONS

Pettit et al, Isolation and structure of Hemibastadinols 1-3 from the Papua New Guinea marine sponge lanthella basta, 1996, 59,p. 927-934.*

Patent Abstracts of Japan, vol. 017, No. 391 (C-1087), Jul. 22, 1993 & JP 05 070428 A (Mitsubishi Petrochem Co. Ltd); Mar. 23, 1993; abstract.
Pettit G R et al:, "Isolation and Structure of Hemibastadinols 1-3 from the Papua New Guinea Marine Sponge lanthella basta"; Journal of Natural Products, vol. 59, No. 10, 1996, pp. 927-934, cited in application; examples 9, 10, 13-16.

* cited by examiner

*Primary Examiner*—Taylor Victor Oh
(74) *Attorney, Agent, or Firm*—William F. Mulholland, Inc.

(57) ABSTRACT

The invention relates to α-oxygenated or α-thiolated carboxylic acid phenethylamide derivatives of general formula (I) including the optical isomers thereof and mixtures of such isomers, wherein A stands for optionally substituted aryl or optionally substituted heteroaryl; X is oxygen or sulfur; Y is oxygen or sulfur; $R_1$, is hydrogen, alkyl, alkenyl, alkynyl, cycloalkyl, haloalkyl, haloalkenyl, haloalkynyl or halocycloalkyl; $R_2$ is hydrogen, alkyl, alkenyl, alkynyl, cycloalkyl, cycloalkylalkyl, alkoxy-alkyl, alkoxy-alkenyl, alkoxy-alkynyl, whereof all alkyl- alkenyl-, alkynyl-, or cycloalkyl-groups may be optionally substituted by halogen; or optionally substituted aryl-alkyl, optionally substituted aryl-alkenyl, optionally substituted aryl-alkynyl or optionally substituted aryloxy-alkyl; $R_3$ is hydrogen, alkyl, alkenyl, alkynyl, cycloalkyl, cycloalkyl-alkyl, alkoxy-alkyl, alkoxy-alkenyl, alkoxy-alkynyl, whereof all alkyl- alkenyl-, alkynyl-, or cycloalkyl-groups may be optionally substituted by halogen; or is optionally substituted aryl-alkyl, optionally substituted aryl-alkenyl, optionally substituted aryl-alkynyl, optionally substituted aryloxy-alkyl, optionally substituted heteroaryl-alkyl, optionally substituted heteroaryl-alkenyl or optionally substituted heteroaryl-alkynyl; $R_4$ is alkyl, alkenyl, alkynyl, alkoxy-alkyl, alkoxy, alkenyloxy, alkenyloxy, alkylthio, alkanoyl, alkylamino, dialkylamino, alkoxycarbonyl, whereof all alkyl- alkenyl or alkynyl-groups may be optionally substituted by halogen; or is halogen, cyano, nitro, amino, formyl or carboxyl; $R_5$ is hydrogen, alkyl, alkenyl or alkynyl; n is an integer 0, 1, 2, 3, or 4; B, represents a bridge member —$CR_{10}R_{11}$—, wherein $R_{10}$ and $R_{11}$ independently of each other are hydrogen or alkyl; and $B_2$ is an alkylene bridge. These compounds possess useful plant protecting properties and may advantageously be employed in agricultural practice for controlling or preventing the infestation of plants by phytopathogenic microorganisms, especially fungi.

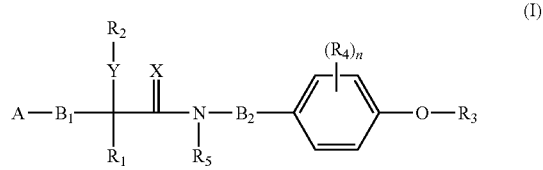

(I)

20 Claims, No Drawings

α-OXYGENATED OR α-THIOLATED CARBOXYLIC ACID PHENETHYLAMIDE DERIVATIVES

This application is a 371 of International Application No. PCT/EP02/12846 filed Nov. 15, 2002, which claims priority to GB 0127557.7, filed Nov. 16, 2001, the contents of which are incorporated herein by reference.

The present invention relates to novel agrochemical compositions comprising as active ingredients at least one compound of the α-oxygenated or α-thiolated carboxylic acid phenethylamide derivatives of formula I. It relates to the preparation of the active ingredients and to the novel compounds encompassed by the general formula I. The invention further relates to the preparation of the agrochemical compositions and to the use of the compounds of formula I, or the use of the compositions for controlling or preventing the infestation of cultivated crop plants by phytopathogenic microorganisms, especially fungi.

The invention relates to microbiocidal α-oxygenated or α-thiolated carboxylic acid phenethylamide derivatives of the general formula I

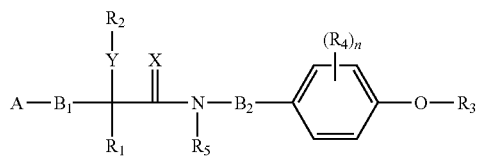

(I)

including the optical isomers thereof and mixtures of such isomers, wherein

A stands for optionally substituted aryl or optionally substituted heteroaryl;
X is oxygen or sulfur;
Y is oxygen or sulfur;
$R_1$ is hydrogen, alkyl, alkenyl, alkynyl, cycloalkyl, haloalkyl, haloalkenyl, haloalkynyl or halocycloalkyl;
$R_2$ is hydrogen, alkyl, alkenyl, alkynyl, cycloalkyl, cycloalkyl-alkyl, alkoxy-alkyl, alkoxy-alkenyl, alkoxy-alkynyl, whereof all alkyl- alkenyl-, alkynyl-, or cycloalkyl-groups may be optionally substituted by halogen; or optionally substituted aryl-alkyl, optionally substituted aryl-alkenyl, optionally substituted aryl-alkynyl or optionally substituted aryloxy-alkyl;
$R_3$ is hydrogen, alkyl, alkenyl, alkynyl, cycloalkyl, cycloalkyl-alkyl, alkoxy-alkyl, alkoxy-alkenyl, alkoxy-alkynyl, whereof all alkyl- alkenyl-, alkynyl-, or cycloalkyl-groups may be optionally substituted by halogen; or is optionally substituted aryl-alkyl, optionally substituted aryl-alkenyl, optionally substituted aryl-alkynyl, optionally substituted aryloxy-alkyl, optionally substituted heteroaryl-alkyl, optionally substituted heteroaryl-alkenyl or optionally substituted heteroaryl-alkynyl;
$R_4$ is alkyl, alkenyl, alkynyl, alkoxy-alkyl, alkoxy, alkenyloxy, alkynyloxy, alkylthio, alkanoyl, alkylamino, dialkylamino, alkoxycarbonyl, whereof all alkyl- alkenyl or alkynyl-groups may be optionally substituted by halogen; or is halogen, cyano, nitro, amino, formyl or carboxyl;
$R_5$ is hydrogen, alkyl, alkenyl or alkynyl;
n is an integer 0, 1, 2, 3, or 4;
$B_1$ represents a bridge member —$CR_{10}R_{11}$—, wherein $R_{10}$ and $R_{11}$ independently of each other are hydrogen or alkyl; and
$B_2$ is an alkylene bridge.

In the above definition aryl includes aromatic hydrocarbon rings like phenyl, naphthyl, anthracenyl, phenanthrenyl and biphenyl like 1,3-biphenyl and 1,4-biphenyl, with phenyl being preferred. The same definition applies where aryl is part of aryloxy. Heteroaryl stands for aromatic ring systems comprising mono-, bi- or tricyclic systems wherein at least one oxygen, nitrogen or sulfur atom is present as a ring member. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothienyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

The above aryl and heteroaryl groups may be optionally substituted. This means that they may carry one or more identical or different substituents. Normally not more than three substituents are present at the same time. Examples of substituents of aryl or heteroaryl groups are: alkyl, alkenyl, alkynyl, cycloalkyl, cycloalkyl-alkyl, phenyl and phenyl-alkyl, it being possible in turn for all of the preceding groups to carry one or more identical or different halogen atoms; alkoxy; alkenyloxy; alkynyloxy; alkoxyalkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; or alkynyloxycarbonyl. Typical examples include 4-chlorophenyl, 4-bromophenyl, 3,4-dichlorophenyl, 4-chloro-3-fluorophenyl, 3-chloro-4-fluorophenyl, 4-methylphenyl, 4-ethylphenyl, 4-propargyloxyphenyl, 1-naphthyl, 2-naphthyl, 4-biphenylyl, 4'-chloro-4-biphenylyl, 5-chloro-thien-2-yl, 5-methyl-thien-2-yl, 5-methyl-fur-2-yl, 5,6,7,8-tetrahydro-1-naphthyl, 5,6,7,8-tetrahydro-2-naphthyl, 3,4-dioxomethylenyl-phenyl, 3,4-dioxoethylenyl-phenyl, 6-benzothienyl, 7-benzothienyl, 3-methylphenyl, 4-fluorophenyl, 4-ethenylphenyl, 4-ethynylphenyl, 4-propylphenyl, 4-isopropylphenyl, 4-tert-butylphenyl, 4-ethoxyphenyl, 4-ethynyloxyphenyl, 4-phenoxyphenyl, 4-methylthiophenyl, 4-methylsulfonylphenyl, 4-cyanophenyl, 4-nitrophenyl, 4-methoxycarbonyl-phenyl, 3-bromophenyl, 3-chlorophenyl, 2-chlorophenyl, 2,4-dichlorophenyl, 3,4,5-trichlorophenyl, 3,4-difluorophenyl, 3,4-dibromophenyl, 3,4-dimethoxyphenyl, 3,4-dimethylphenyl, 3-chloro-4-cyanophenyl, 4-chloro-3-cyanophenyl, 3-bromo-4-methylphenyl, 4-methoxy-3-methylphenyl, 3-fluoro-4-methoxyphenyl, 4-chloro-3-methylphenyl, 4-chloro-3-trifluoromethyl-phenyl, 4-bromo-3-chlorophenyl, 4-trifluoromethylphenyl, 4-trifluoromethoxyphenyl, 4-methoxyphenyl, 4'-methyl-4-biphenylyl, 4'-trifluoromethyl-4-biphenylyl, 4'-bromo-4-biphenylyl, 4'-cyano-4-biphenylyl, 3'4'-dichloro-4-biphenylyl, etc.

Again, the same optional substituents may be present when aryl is part of aryloxy or arylthio.

Optionally substituted alkyl, alkenyl or alkynyl groups may carry one or more substituents selected from halogen, alkyl, alkoxy, alkylthio, cycloalkyl, phenyl, nitro, cyano, hydroxy, mercapto, alkylcarbonyl or alkoxycarbonyl. This also applies where alkyl, alkenyl or alkynyl is part of another substituent like alkoxy, alkylthio, alkylsulfinyl, alkylsulfonyl, alkenyloxy, alkenylthio, alkenylsulfinyl, alkenylsufonyl, alkynyloxy, alkynylthio, alkynylsulfinyl and alkynylsulfonyl.

Preferably, the number of substituents is no more than three with the exception of halogen, where the alkyl groups may be perhalogenated.

In the above definitions "halo" or "halogen" includes fluorine, chlorine, bromine and iodine. The alkyl, alkenyl and alkynyl radicals may be straight-chain or branched. This applies also to the alkyl, alkenyl or alkynyl parts of other alkyl-, alkenyl- or alkynyl-containing groups. Depending upon the number of carbon atoms mentioned, alkyl on its own or as part of another substituent is to be understood as being, for example, methyl, ethyl, propyl, butyl, pentyl, hexyl, heptyl, octyl, nonyl, decyl, undecyl, dodecyl and the isomers thereof, for example isopropyl, isobutyl, tert-butyl or sec-butyl, isopentyl or tert-pentyl.

Cycloalkyl for example is, depending upon the number of carbon atoms mentioned, cyclopropyl, cyclobutyl, cyclopentyl, cyclohexyl, bicyclohexyl, cycloheptyl, bicycloheptyl, cyclooctyl or bicyclooctyl.

Depending upon the number of carbon atoms mentioned, alkenyl as a group or as a structural element of other groups is to be understood as being, for example —CH=CH$_2$, —CH$_2$—CH=CH$_2$, —CH=CH—CH$_3$, —CH$_2$—CH=CH—CH$_3$, —CH$_2$—CH$_2$—CH=CH$_2$, —CH$_2$—CH(CH$_3$)—CH=CH$_2$, —CH$_2$—C(CH$_3$)=CH$_2$, —CH=CH—(CH$_2$)$_2$—CH$_3$, —CH$_2$—CH$_2$—CH=CH—CH$_3$, —CH$_2$—CH$_2$—C(CH$_3$)=CH—CH$_3$, —CH(CH$_3$)—CH$_2$—CH=CH—CH$_3$, —CH$_2$—CH$_2$—CH=CH—CH$_2$—CH$_3$, —CH=CH—(CH$_2$)$_3$—CH$_3$, —CH$_2$—CH$_2$—CH=C(CH$_3$)—CH$_3$, —CH$_2$—CH$_2$—CH=C(CH$_3$)—CH$_2$—CH$_3$, —C(CH$_3$)=CH$_2$, —CH(CH$_3$)—CH=CH$_2$, —CH(CH$_3$)—CH=CH—CH$_3$, —CH(CH$_3$)—CH$_2$—CH=CH—CH$_2$, —CH$_2$—C(CH$_3$)=CH—CH$_3$, CH(CH$_3$)—C(CH$_3$)=CH$_2$, —CH$_2$—C(CH$_3$)=CH—CH$_3$, —C(CH$_3$)=CH—(CH$_2$)$_2$—CH$_3$, —CH(CH$_3$)—CH$_2$—C(CH$_3$)=CH—CH$_3$, —CH(CH$_3$)—(CH$_2$)$_2$—CH=CH$_2$, —C(CH$_3$)=CH—(CH$_2$)$_3$—CH$_3$, —CH(CH$_3$)—CH$_2$—CH=CH—CH$_2$—CH$_3$, —(CH$_2$)$_3$—CH=CH$_2$, —C(CH$_3$)=CH—CH$_3$, —CH(CH$_3$)—CH$_2$—C(CH$_3$)=CH—CH$_3$, or —CH(CH$_3$)—CH$_2$—CH=CH—CH$_2$—CH$_3$.

Alkynyl as a group or as a structural element of other groups is, for example —C≡CH, —CH$_2$—C≡CH, —C≡C—CH$_3$, —CH$_2$—C≡C—CH$_3$, —CH$_2$—CH$_2$—C≡CH, —O≡C—CH$_2$—CH$_3$, —CH$_2$—CH(CH$_3$)—C≡CH, —C≡C—(CH$_2$)$_2$—CH$_3$, —CH$_2$—CH$_2$—C≡C—CH$_3$, —CH(CH$_3$)—CH$_2$—C≡C—CH$_3$, —CH$_2$—CH$_2$—C≡C—CH$_2$—CH$_3$, —O≡C—(CH$_2$)$_3$—CH$_3$, —C≡C—(CH$_2$)$_4$—CH$_3$, —CH(CH$_3$)—C≡CH, —CH(CH$_3$)—C≡C—CH$_3$, —CH(C$_2$H$_5$)—C≡C—CH$_3$, —CH(CH$_3$)—CH$_2$—C≡CH, —CH(CH$_3$)—(CH$_2$)$_2$—C≡CH, —CH(CH$_3$)—CH$_2$—C≡C—CH$_2$—CH$_3$, —(CH$_2$)$_3$—C≡CH, or —CH(CH$_3$)—CH$_2$—C≡C—CH$_2$—CH$_3$, depending on the number of carbon atoms present.

A haloalkyl, haloalkenyl, haloalkynyl or halocycloalkyl group may contain one or more (identical or different) halogen atoms, and for example may stand for CHCl$_2$, CH$_2$F, CCl$_3$, CH$_2$Cl, CHF$_2$, CF$_3$, CH$_2$CH$_2$Br, C$_2$Cl$_5$, CH$_2$Br, CHClBr, CF$_3$CH$_2$, CH$_2$CH$_2$Cl, CH$_2$CH$_2$F, CH$_2$CHF$_2$, CH$_2$—C=CHCl, CH=CCl$_2$, CH=CF$_2$, CH$_2$—C=CCl, CH$_2$—C≡C—CF$_3$, etc.

B$_1$ and B$_2$ characterize bivalent portions of the molecular structure of formula I, which have the function of bridging members. Typically, these portions have a linear structure, but may also be branched and may carry further substituents. Examples include the bridge members of the formula —CH(R$_{20}$)—(CH$_2$)$_p$—, wherein R$_{20}$ stands for hydrogen or C$_1$-C$_4$-alkyl and p is an integer 0 or 1 for the bridge B$_2$, which belong to the generic group of alkylenes. Examples for the B$_1$-bridge stand for an C$_1$-C$_4$-alkylene bridge which links the adjacent part of the molecule of formula I to one single carbon atom. Typical examples for B$_2$ include —CH$_2$—, —CH$_2$CH$_2$—, —CH(CH$_3$)—CH$_2$—, —CH(CH$_3$)—, —CH$_2$—CH$_2$—CH$_2$—, —CH(CH$_3$)—CH$_2$— or —CH$_2$—CH(CH$_3$)—. Examples for the linking members for B, include the linking members having only a single carbon atom as linking member. Typical examples encompass —CH$_2$—, —CH(CH$_3$)—, —CH(C$_2$H$_5$)— and —C(CH$_3$)$_2$—.

The presence of at least one asymmetric carbon atom in the compounds of formula I means that the compounds may occur in optically isomeric and enantiomeric forms. As a result of the presence of a possible aliphatic C=C double bond, geometric isomerism may also occur. Formula I is intended to include all those possible isomeric forms and mixtures thereof. Where no specific isomer is specified the mixtures of diastereomers or racemat is meant, as obtainable from the synthesis methods.

Preferred subgroups of compounds of formula I are those wherein

A is phenyl, naphthyl, 1,3-biphenyl, 1,4-biphenyl, fluorenyl, tetralinyl, indanyl, methylendioxyphenyl, (1,2-ethylene)dioxyphenyl, furanyl, thienyl, pyrrolyl, imidazolyl, pyrazolyl, oxazolyl, isoxazolyl, thiazolyl, isothiazolyl, oxadiazolyl, thiadiazolyl, triazolyl, tetrazolyl, pyridyl, pyridazinyl, pyrimidinyl, pyrazinyl, triazinyl, tetrazinyl, indolyl, indazolyl, benzofuranyl, benzothienyl, benzothiazolyl, benzoxazolyl, quinolinyl or isoquinolinyl, each optionally substituted by one or more substituents selected from the group comprising C$_1$-C$_{10}$-alkyl, C$_2$-C$_{10}$-alkenyl, C$_2$-C$_{10}$-alkynyl, C$_1$-C$_8$-cycloalkyl, C$_1$-C$_8$-cycloalkyl-C$_1$-C$_{10}$-alkyl, phenyl, phenyl-C$_1$-C$_{10}$-alkyl, C$_1$-C$_{10}$-alkoxy, C$_3$-C$_{10}$-alkenyloxy, C$_3$-C$_{10}$-alkynyloxy, C$_1$-C$_{10}$-alkylthio, C$_1$-C$_{10}$-alkylsulfonyl, C$_1$-C$_{10}$-alkoxy-C$_1$-C$_{10}$-alkyl, C$_1$-C$_{10}$-alkanoyl, C$_1$-C$_{10}$-alkoxycarbonyl, C$_3$-C$_{10}$-alkenyloxycarbonyl, C$_3$-C$_{10}$-alkynyloxycarbonyl, C$_1$-C$_{10}$-alkylamino, di-C$_1$-C$_{10}$-alkylamino, hydroxy, halogen, cyano, nitro, amino and formyl radicals, wherein in turn the alkyl- alkenyl-, alkynyl- and cycloalkyl-groups may be optionally substituted by one or more halogen atoms; or A is phenyl, naphthyl, 1,4-biphenyl, tetralinyl, indanyl, methylendioxyphenyl, (1,2-ethylene)dioxyphenyl, furanyl, thienyl or pyridyl, each optionally substituted by one, two or three substituents selected from the group comprising C$_1$-C$_{10}$-alkyl, C$_1$-C$_{10}$-haloalkyl, C$_2$-C$_{10}$-alkenyl, C$_2$-C$_{10}$-haloalkenyl, C$_2$-C$_{10}$-alkynyl, benzyl, C$_1$-C$_{10}$-alkoxy, C$_1$-C$_{10}$-haloalkoxy, C$_3$-C$_{10}$-alkenyloxy, C$_3$-C$_{10}$-alkynyloxy, C$_1$-C$_{10}$-alkylthio, C$_1$-C$_{10}$-haloalkylthio, C$_1$-C$_{10}$-alkylsulfonyl, C$_1$-C$_6$-alkoxy-C$_1$-C$_6$-alkyl, C$_1$-C$_{10}$-alkanoyl, C$_1$-C$_{10}$-alkoxycarbonyl, hydroxy, halogen, cyano, nitro and formyl; or A is phenyl, naphthyl, 1,4-biphenyl, tetralinyl, indanyl, methylendioxyphenyl, thienyl, each optionally substituted by one, two or three substituents selected from the group comprising C$_1$-C$_{10}$-alkyl, C$_1$-C$_{10}$-haloalkyl, C$_2$-C$_{10}$-alkenyl, C$_2$-C$_{10}$-alkynyl, benzyl, C$_1$-C$_{10}$-alkoxy, C$_1$-C$_{10}$-haloalkoxy, C$_1$-C$_{10}$-alkylthio, C$_1$-C$_{10}$-haloalkylthio, C$_1$-C$_{10}$-alkanoyl, C$_1$-C$_{10}$-alkoxycarbonyl, halogen, cyano, nitro and formyl; or A is phenyl or thienyl, optionally substituted by one or two substituents selected from the group comprising C$_1$-C$_4$-alkyl, C$_1$-C$_4$-haloalkyl, C$_2$-C$_4$-alkenyl, C$_1$-C$_4$-alkoxy, C$_1$-C$_{10}$alkylthio, C$_1$-C$_4$-alkanoyl, halogen and cyano; or A is phenyl, optionally substituted by one or two substituents selected from the group comprising C$_1$-C$_4$-alkyl, C$_1$-C$_4$-haloalkyl, halogen and cyano; or X is oxygen; or Y is oxygen; or R$_1$ stands for hydrogen, C$_1$-C$_{10}$-alkyl, C$_3$-C$_{10}$-alkenyl, C$_3$-C$_{10}$-alkynyl or C$_3$-C$_8$-cycloalkyl, wherein each alkyl- alkenyl-, alkynyl- and cycloalkyl-group may be optionally substituted by halogen; or $R_1$ is hydrogen, $C_1$-$C_{10}$-alkyl, $C_3$-$C_{10}$-alkenyl, $C_3$-$C_{10}$-alkynyl, $C_1$-$C_{10}$-haloalkyl, $C_3$-$C_{10}$-haloalkenyl or $C_3$-$C_{10}$-haloalkynyl; or $R_1$ is hydrogen, $C_1$-$C_8$-alkyl, $C_3$-$C_8$-alkenyl or $C_3$-$C_8$-alkynyl; or $R_1$ is hydrogen; or $R_2$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_1$-$C_6$-alkoxy-$C_1$-$C_6$-alkyl, $C_1$-$C_6$-alkoxy-$C_3$-$C_{10}$-alkenyl or $C_1$-$C_6$-alkoxy-$C_3$-$C_{10}$-alkynyl, wherein all alkyl- alkenyl-, alkynyl-, or cycloalkyl-groups may be optionally substituted by halogen; or stands for optionally substituted aryl-$C_1$-$C_6$-alkyl, optionally substituted aryl-$C_3$-$C_{10}$-alkenyl, optionally substituted aryl-$C_3$-$C_{10}$-alkynyl or optionally substituted aryloxy-$C_1$-$C_6$-alkyl; or $R_2$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$ cycloalkyl-$C_1$-$C_6$-alkyl, $C_3$-$C_8$-cycloalkyl-$C_3$-$C_6$-alkenyl, $C_3$-$C_8$-cycloalkyl-$C_3$-$C_6$-alkynyl, $C_1$-$C_6$-alkoxy-$C_1$-$C_6$-alkyl, $C_1$-$C_6$-alkoxy-$C_3$-$C_6$-alkenyl, $C_1$-$C_6$-alkoxy-$C_3$-$C_6$-alkynyl, $C_1$-$C_{10}$-haloalkyl, $C_3$-$C_{10}$-haloalkenyl, $C_3$-$C_{10}$-haloalkynyl, phenyl-$C_1$-$C_6$-alkyl, phenyl-$C_1$-$C_6$alkenyl or phenyl-$C_1$-$C_6$-alkynyl, wherein phenyl may optionally be mono- or disubstituted by substituents selected from the group comprising $C_1$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkanoyl, $C_1$-$C_6$alkoxycarbonyl, halogen, cyano, nitro and formyl; or $R_2$ stands for hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl, $C_1$-$C_4$-alkoxy-$C_3$-$C_4$-alkynyl, $C_1$-$C_8$-haloalkyl or $C_3$-$C_8$-haloalkynyl; or $R_2$ is hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl or $C_1$-$C_4$-alkoxy-$C_3$-$C_4$-alkynyl; or $R_2$ is hydrogen, $C_1$-$C_4$-alkyl, $C_3$-$C_4$-alkenyl or $C_3$-$C_4$-alkynyl; or $R_3$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_1$-$C_6$-alkoxy-$C_1$-$C_6$-alkyl, $C_1$-$C_6$-alkoxy-$C_3$-$C_{10}$-alkenyl or $C_1$-$C_6$-alkoxy-$C_3$-$C_{10}$-alkynyl, wherein all alkyl- alkenyl-, alkynyl-, or cycloalkyl-groups may be optionally substituted by halogen; or is optionally substituted aryl-$C_1$-$C_6$-alkyl, optionally substituted aryl-$C_3$-$C_{10}$-alkenyl, optionally substituted aryl-$C_3$-$C_{10}$-alkynyl, optionally substituted aryloxy-$C_1$-$C_6$-alkyl, optionally substituted heteroaryl-$C_1$-$C_6$-alkyl, optionally substituted heteroaryl-$C_3$-$C_{10}$-alkenyl or optionally substituted heteroaryl-$C_3$-$C_{10}$-alkynyl; or $R_3$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_3$-$C_8$-cycloalkyl-$C_3$-$C_6$-alkenyl, $C_3$-$C_8$-cycloalkyl-$C_3$-$C_6$-alkynyl, $C_1$-$C_6$-alkoxy-$C_1$-$C_6$-alkyl, $C_1$-$C_6$-alkoxy-$C_3$-$C_6$-alkenyl, $C_1$-$C_6$-alkoxy-$C_3$-$C_6$-alkynyl, $C_1$-$C_{10}$-haloalkyl, $C_3$-$C_{10}$-haloalkenyl, $C_3$-$C_{10}$-haloalkynyl, phenyl-$C_1$-$C_6$-alkyl, phenyl-$C_1$-$C_6$alkenyl or phenyl-$C_1$-$C_6$-alkynyl, wherein the phenyl groups are optionally mono- or disubstituted by radicals selected from the group comprising $C_1$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkanoyl, $C_1$-$C_6$-alkoxycarbonyl, halogen, cyano, nitro and formyl; or $R_3$ is hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl, $C_1$-$C_4$-alkoxy-$C_3$-$C_4$-alkynyl, $C_1$-$C_8$-haloalkyl or $C_3$-$C_8$-haloalkynyl; or $R_3$ is hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl or $C_1$-$C_4$-alkoxy-$C_3$-$C_4$-alkynyl; or $R_3$ is $C_1$-$C_4$-alkyl, $C_3$-$C_4$-alkenyl or $C_3$-$C_4$-alkynyl; or $R_4$ is $C_1$-$C_6$-alkyl, $C_3$-$C_6$-alkenyl, $C_3$-$C_6$-alkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-alkynyloxy, $C_1$-$C_6$-alkylthio, $C_1$-$C_6$-alkanoyl, $C_1$-$C_6$-alkylamino, di-$C_1$-$C_6$alkylamino or $C_1$-$C_6$-alkoxycarbonyl, wherein each alkyl- alkenyl or alkynyl-group may be optionally substituted by halogen; or is halogen, cyano, nitro, amino, formyl or carboxyl; or $R_4$ is $C_1$-$C_6$-alkyl, $C_1$-$C_6$-haloalkyl, $C_1$-$C_6$-alkoxy, $C_3$-$C_6$-alkenyloxy, $C_3$-$C_6$-alkynyloxy, $C_1$-$C_6$alkylthio, halogen, cyano or nitro; or $R_4$ is $C_1$-$C_6$-alkoxy, $C_3$-$C_6$-alkenyloxy, $C_3$-$C_6$-alkynyloxy or halogen; or $R_4$ is 3-$C_1$-$C_6$-alkoxy; or $R_4$ is 3-methoxy or 3-ethoxy; or $R_5$ is hydrogen, $C_1$-$C_6$-alkyl, $C_3$-$C_6$-alkenyl or $C_3$-$C_6$-alkynyl; or $R_5$ is hydrogen or $C_1$-$C_4$-alkyl; or $R_5$ is hydrogen or methyl; or $R_5$ is hydrogen; or $B_1$ stands for a bridge member —$CR_{10}R_{11}$—, wherein $R_{10}$ and $R_1$, independently of each other are hydrogen or $C_1$-$C_4$-alkyl; or $B_1$ is selected from —$CH_2$—, —$CH(CH_3)$— and —$C(CH_3)_2$—; or n is an integer from 0 to 2; or n is the integer 0 or 1; or n is the integer 1; or $B_2$ is an $C_1$-$C_6$-alkylene-bridge; or $B_2$ is an alkylene-bridge of the formula —$CH(R_{20})$—$(CH_2)_p$—, wherein $R_{20}$ stands for hydrogen or $C_1$-$C_4$-alkyl and p is an integer 0, 1 or 2; or $B_2$ is —$CH_2$—$CH_2$—, $CH_2$—, $CH(CH_3)$—$CH_2$— or $CH(CH_3)$—; or $B_2$ is —$CH_2$—$CH_2$—.

Further preferred subgroups are those wherein

A is phenyl, naphthyl, 1,3-biphenyl, 1,4-biphenyl, fluorenyl, tetralinyl, indanyl, methylendioxyphenyl, (1,2-ethylene)dioxyphenyl, furanyl, thienyl, pyrrolyl, imidazolyl, pyrazolyl, oxazolyl, isoxazolyl, thiazolyl, isothiazolyl, oxadiazolyl, thiadiazolyl, triazolyl, tetrazolyl, pyridyl, pyridazinyl, pyrimidinyl, pyrazinyl, triazinyl, tetrazinyl, indolyl, indazolyl, benzofuranyl, benzothienyl, benzothiazolyl, benzoxazolyl, quinolinyl or isoquinolinyl, each optionally substituted by one or more substituents selected from the group comprising $C_1$-$C_{10}$-alkyl, $C_2$-$C_{10}$-alkenyl, $C_2$-$C_{10}$-alkynyl, $C_1$-$C_8$-cycloalkyl, $C_1$-$C_8$-cycloalkyl-$C_1$-$C_{10}$-alkyl, phenyl, phenyl-$C_1$-$C_{10}$-alkyl, $C_1$-$C_{10}$-alkoxy, $C_3$-$C_{10}$-alkenyloxy, $C_3$-$C_{10}$-alkynyloxy, $C_1$-$C_{10}$-alkylthio, $C_1$-$C_{10}$-alkylsulfonyl, $C_1$-$C_{10}$-alkoxy-$C_1$-$C_{10}$-alkyl, $C_1$-$C_{10}$-alkanoyl, $C_1$-$C_{10}$-alkoxycarbonyl, $C_3$-$C_{10}$-alkenyloxycarbonyl, $C_3$-$C_{10}$-alkynyloxycarbonyl, $C_1$-$C_{10}$-alkylamino, di-$C_1$-$C_{10}$-alkylamino, hydroxy, halogen, cyano, nitro, amino and formyl radicals, wherein in turn the alkyl- alkenyl-, alkynyl- and cycloalkyl-groups may be optionally substituted by one or more halogen atoms; and X is oxygen or sulfur; and Y is oxygen or sulfur; and $R_1$ stands for hydrogen, $C_1$-$C_{10}$-alkyl, $C_3$-$C_{10}$-alkenyl, $C_3$-$C_{10}$-alkynyl or $C_3$-$C_8$-cycloalkyl, wherein each alkyl- alkenyl-, alkynyl- and cycloalkyl-group may be optionally substituted by halogen; and $R_2$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_1$-$C_6$-alkoxy-$C_1$-$C_6$-alkyl, $C_1$-$C_6$-alkoxy-$C_3$-$C_{10}$-alkenyl or $C_1$-$C_6$-alkoxy-$C_3$-$C_{10}$-alkynyl, wherein all alkyl- alkenyl-, alkynyl-, or cycloalkyl-groups may be optionally substituted by halogen; or stands for optionally substituted aryl-$C_1$-$C_6$-alkyl, optionally substituted aryl-$C_3$-$C_{10}$-alkenyl, optionally substituted aryl-$C_3$-$C_{10}$-alkynyl or optionally substituted aryloxy-$C_1$-$C_6$-alkyl; and $R_3$ is hydrogen, $C_1$-$C_{10}$-alkyl, $C_3$-$C_{10}$ alkenyl, $C_3$-$C_{10}$-alkynyl, $C_3$-$C_8$-cycloalkyl, $C_3$-$C_8$ cycloalkyl-$C_1$-$C_6$-alkyl, $C_1$-$C_6$-alkoxy-$C_1$-$C_6$-alkyl, $C_1$-$C_6$-alkoxy-$C_3$-$C_{10}$-alkenyl or $C_1$-$C_6$-alkoxy-$C_3$-$C_{10}$-alkynyl, wherein each alkyl- alkenyl-, alkynyl-, or cycloalkyl-group may be optionally substituted by halogen; or is optionally substituted aryl-$C_1$-$C_6$-alkyl, optionally substituted aryl-$C_3$-$C_{10}$-alkenyl, optionally substituted aryl-$C_3$-$C_{10}$-alkynyl, optionally substituted aryloxy-$C_1$-$C_6$-alkyl, optionally substituted heteroaryl-$C_1$-$C_6$-alkyl, optionally substituted heteroaryl-$C_3$-$C_{10}$-alkenyl or optionally substituted heteroaryl-$C_3$-$C_{10}$-alkynyl; and $R_4$ is $C_1$-$C_6$-alkyl, $C_3$-$C_6$-alkenyl, $C_3$-$C_6$-alkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-alkynyloxy, $C_1$-$C_6$-alkylthio, $C_1$-$C_6$-alkanoyl, $C_1$-$C_6$-alkylamino, di-$C_1$-$C_6$alkylamino or $C_1$-$C_6$-alkoxycarbonyl, wherein each alkyl- alkenyl or alkynyl-group may be optionally substituted by halogen; or is halogen, cyano, nitro, amino, formyl or carboxyl; and $R_5$ is hydrogen, $C_1$-$C_6$-alkyl, $C_3$-$C_6$-alkenyl or $C_3$-$C_6$-alkynyl; and $B_2$ is an $C_1$-$C_6$-alkylene-bridge; and n is an integer from 0 to 2.

Among these compounds those are preferred wherein A is phenyl, naphthyl, 1,4-biphenyl, tetralinyl, indanyl, methylendioxyphenyl, (1,2-ethylene)dioxyphenyl, furanyl, thienyl or pyridyl, each optionally substituted by one, two or three substituents selected from the group comprising $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, benzyl, $C_1$-$C_{10}$-alkoxy, $C_1$-$C_{10}$-haloalkoxy, $C_3$-$C_{10}$-alkenyloxy, $C_3$-$C_{10}$-alkynyloxy, $C_1$-$C_{10}$-alkylthio, $C_1$-$C_{10}$-haloalkylthio, $C_1$-$C_{10}$-alkylsulfonyl, $C_1$-$C_6$-alkoxy-$C_1$-$C_6$-alkyl, $C_1$-$C_{10}$-alkanoyl, $C_1$-$C_{10}$-alkoxycarbonyl, hydroxy, halogen, cyano, nitro and formyl.

Further preferred subgroups are those wherein

A is phenyl, naphthyl, 1,4-biphenyl, tetralinyl, indanyl, methylendioxyphenyl, (1,2-ethylene)dioxyphenyl, furanyl, thienyl or pyridyl, each optionally substituted by one, two or three substituents selected from the group comprising $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, benzyl, $C_1$-$C_{10}$-alkoxy, $C_1$-$C_{10}$-haloalkoxy, $C_3$-$C_{10}$-alkenyloxy, $C_3$-$C_{10}$-alkynyloxy, $C_1$-$C_{10}$-alkylthio, $C_1$-$C_{10}$-haloalkylthio, $C_1$-$C_{10}$-alkylsulfonyl, $C_1$-$C_6$-alkoxy-$C_1$-$C_6$-alkyl, $C_1$-$C_{10}$-alkanoyl, $C_1$-$C_{10}$-alkoxycarbonyl, hydroxy, halogen, cyano, nitro and formyl; and X is oxygen or sulfur; and Y is oxygen or sulfur; and $R_1$ is hydrogen, $C_1$-$C_{10}$-alkyl, $C_3$-$C_{10}$-alkenyl, $C_3$-$C_{10}$-alkynyl, $C_1$-$C_{10}$-haloalkyl, $C_3$-$C_{10}$-haloalkenyl or $C_3$-$C_{10}$-haloalkynyl; and $R_2$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_3$-$C_8$-cycloalkyl-$C_3$-$C_6$-alkenyl, $C_3$-$C_8$-cycloalkyl-$C_3$-$C_6$-alkynyl, $C_1$-$C_6$-alkoxy-$C_1$-$C_6$-alkyl, $C_1$-$C_6$-alkoxy-$C_3$-$C_6$-alkenyl, $C_1$-$C_6$-alkoxy-$C_3$-$C_6$-alkynyl, $C_1$-$C_{10}$-haloalkyl, $C_3$-$C_{10}$-haloalkenyl, $C_3$-$C_{10}$-haloalkynyl, phenyl-$C_1$-$C_6$-alkyl, phenyl-$C_1$-$C_6$-alkenyl or phenyl-$C_1$-$C_6$-alkynyl, wherein phenyl may optionally be mono- or disubstituted by substituents selected from the group comprising $C_0$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkanoyl, $C_1$-$C_6$-alkoxycarbonyl, halogen, cyano, nitro and formyl; and $R_3$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_3$-$C_8$-cycloalkyl-$C_3$-$C_6$-alkenyl, $C_3$-$C_8$-cycloalkyl-$C_3$-$C_6$alkynyl, $C_1$-$C_6$-alkoxy-$C_1$-$C_6$-alkyl, $C_1$-$C_6$-alkoxy-$C_3$-$C_6$-alkenyl, $C_1$-$C_6$-alkoxy-$C_3$-$C_6$alkynyl, $C_1$-$C_{10}$-haloalkyl, $C_3$-$C_{10}$-haloalkenyl, $C_3$-$C_{10}$-haloalkynyl, phenyl-$C_1$-$C_6$-alkyl, phenyl-$C_{11}$-$C_6$alkenyl or phenyl-$C_1$-$C_6$-alkynyl, wherein the phenyl groups are optionally mono- or disubstituted by radicals selected from the group comprising $C_1$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$alkylthio, $C_1$-$C_6$-haloalkylthio, $C_1$-$C_6$-alkanoyl, $C_1$-$C_6$-alkoxycarbonyl, halogen, cyano, nitro and formyl; and $R_4$ is $C_1$-$C_6$-alkyl, $C_1$-$C_6$-haloalkyl, $C_1$-$C_6$-alkoxy, $C_3$-$C_6$-alkenyloxy, $C_3$-$C_6$-alkynyloxy, $C_1$-$C_6$alkylthio, halogen, cyano or nitro; and $R_5$ is hydrogen, $C_1$-$C_6$-alkyl, $C_3$-$C_6$-alkenyl or $C_3$-$C_6$-alkynyl; and n is an integer from 0 to 2; and $B_2$ is an alkylene-bridge of the formula —$CH(R_{20})$—$(CH_2)_p$—, wherein $R_{20}$ stands for hydrogen or $C_1$-$C_4$-alkyl and p is an integer 0, 1 or 2; or wherein A is phenyl, naphthyl, 1,4-biphenyl, tetralinyl, indanyl, methylendioxyphenyl, thienyl, each optionally substituted by one, two or three substituents selected from the group comprising $C_1$-$C_{10}$-alkyl, $C_1$-$C_{10}$-haloalkyl, $C_2$-$C_{10}$-alkenyl, $C_2$-$C_{10}$-alkynyl, benzyl, $C_1$-$C_{10}$alkoxy, $C_1$-$C_{10}$-haloalkoxy, $C_1$-$C_{10}$-alkylthio, $C_1$-$C_{10}$-haloalkylthio, $C_1$-$C_{10}$-alkanoyl, $C_1$-$C_{10}$-alkoxycarbonyl, halogen, cyano, nitro and formyl; and X is oxygen or sulfur; and Y is oxygen or sulfur; and $R_1$ is hydrogen, $C_1$-$C_8$-alkyl, $C_3$-$C_8$-alkenyl or $C_3$-$C_8$-alkynyl; and $R_2$ stands for hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl, $C_1$-$C_4$-alkoxy-$C_3$-$C_4$-alkynyl, $C_1$-$C_8$-haloalkyl or $C_3$-$C_8$-haloalkynyl; and $R_3$ is hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl, $C_1$-$C_4$-alkoxy-$C_3$$C_4$alkynyl, $C_1$-$C_8$-haloalkyl or $C_3$-$C_8$-haloalkynyl; and $R_4$ is $C_1$-$C_6$-alkoxy, $C_3$-$C_6$-alkenyloxy, $C_3$-$C_6$-alkynyloxy or halogen; and $R_5$ is hydrogen or $C_1$-$C_4$alkyl; and $B_1$ stands for —$CH_2$—, —$CH(CH_3)$— or —$C(CH_3)_2$—; and n is the integer 0 or 1; and $B_2$ is an alkylene-bridge of the formula —$CH(R_{20})$—$(CH_2)_p$—, wherein $R_{20}$ stands for hydrogen or $C_1$-$C_4$alkyl and p is an integer 0, 1 or 2; or wherein A is phenyl or thienyl, optionally substituted by one or two substituents selected from the group comprising $C_1$-$C_4$-alkyl, $C_1$-$C_4$-haloalkyl, $C_2$-$C_4$-alkenyl, $C_1$-$C_4$-alkoxy, $C_1$-$C_{10}$-alkylthio, $C_1$-$C_4$-alkanoyl, halogen and cyano; and X is oxygen; and Y is oxygen; and $R_1$ is hydrogen, $C_1$-$C_8$-alkyl, $C_3$-$C_8$-alkenyl or $C_3$-$C_8$-alkynyl; and $R_2$ is hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl or $C_1$-$C_4$-alkoxy-$C_3$-$C_4$-alkynyl; and $R_3$ is hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl or $C_1$-$C_4$-alkoxy-$C_3$-$C_4$-alkynyl; and $R_4$ is 3-$C_1$-$C_6$-alkoxy; and $R_5$ is hydrogen or methyl; and $B_1$ is selected from —$CH_2$—, —$CH(CH_3)$— and —$C(CH_3)_2$—; and n is the integer 0 or 1; and $B_2$ is —$CH_2$—$CH_2$—, $CH_2$—, $CH(CH_3)$—$CH_2$— or $CH(CH_3)$—; or wherein A is phenyl, optionally substituted by one or two substituents selected from the group comprising $C_1$-$C_4$-alkyl, $C_1$-$C_4$-haloalkyl, halogen and cyano; and X and Y are both oxygen; and $R_1$ is hydrogen; and $R_2$ is hydrogen, $C_1$-$C_4$-alkyl, $C_3$-$C_4$-alkenyl or $C_3$-$C_4$-alkynyl; and $R_3$ is $C_1$-$C_4$-alkyl, $C_3$-$C_4$-alkenyl or $C_3$-$C_4$-alkynyl; and $R_4$ is 3-methoxy or 3-ethoxy; and $R_5$ is hydrogen; and $B_1$ is selected from —$CH_2$—, —$CH(CH_3)$— and —$C(CH_3)_2$—; and n is the integer 1; and $B_2$ is —$CH_2$—$CH_2$—. Preferred individual compounds are:

2-hydroxy-N-[2-(3-methoxy-4-prop-2-ynyloxy-phenyl)-ethyl]-3-phenyl-propionamide,
2-ethoxy-N-[2-(3-methoxy-4-prop-2-ynyloxy-phenyl)-ethyl]-3-phenyl-propionamide,
N-[2-(3-methoxy-4-prop-2-ynyloxy-phenyl)-ethyl]-3-phenyl-2-prop-2-ynyloxy-propionamide,
3-(4-chloro-phenyl)-N-[2-(3-methoxy-4-prop-2-ynyloxy-phenyl)-ethyl]-2-prop-2-ynyloxy-propionamide,
3-(4-chloro-phenyl)-2-methoxy-N-[2-(3-methoxy-4-prop-2-ynyloxy-phenyl)-ethyl]-propionamide,
3-(4-chloro-phenyl)-2-hydroxy-N-[2-(3-methoxy-4-prop-2-ynyloxy-phenyl)-ethyl]-propionamide,
3-(4-fluoro-phenyl)-2-hydroxy-N-[2-(3-methoxy-4-prop-2-ynyloxy-phenyl)-ethyl]-propionamide,
2-ethoxy-3-(4-fluoro-phenyl)-N-[2-(3-methoxy-4-prop-2-ynyloxy-phenyl)-ethyl]-propionamide,
3-(4-fluoro-phenyl)-N-[2-(3-methoxy-4-prop-2-ynyloxy-phenyl)-ethyl]-2-prop-2-ynyloxy-propionamide,
3-(4-bromo-phenyl)-2-hydroxy-N-[2-(3-methoxy-4-prop-2-ynyloxy-phenyl)-ethyl]-propionamide,
3-(4-bromo-phenyl)-N-[2-(3-methoxy-4-prop-2-ynyloxy-phenyl)-ethyl]-2-prop-2-ynyloxy-propionamide,
3-(4-bromo-phenyl)-2-methoxy-N-[2-(3-methoxy-4-prop-2-ynyloxy-phenyl)-ethyl]-propionamide,
3-(4-bromo-phenyl)-2-ethoxy-N-[2-(3-methoxy-4-prop-2-ynyloxy-phenyl)-ethyl]-propionamide,
N-[2-(3-methoxy-4-prop-2-ynyloxy-phenyl)-ethyl]-2-prop-2-ynyloxy-3-p-tolyl-propionamide,
3-(4-ethyl-phenyl)-N-[2-(3-methoxy-4-prop-2-ynyloxy-phenyl)-ethyl]-2-prop-2-ynyloxy-propionamide, and
2-ethoxy-3-(4-ethyl-phenyl)-N-[2-(3-methoxy-4-prop-2-ynyloxy-phenyl)-ethyl]-propionamide.

The optically pure enantiomers of these compounds are mostly obtained as mixtures of the R— and S— forms. It is however possible to obtain the pure enantiomers either by classical separation methods or by stereoselective synthesis methods. In practical preparation enantio-enriched mixture of both forms may be obtained, while on laboratory scale analytically pure enatiomers may be obtained, such as:

(R)-2-hydroxy-N-[2-(3-methoxy-4-prop-2-ynyloxy-phenyl)-ethyl]-3-phenyl-propionamide,
(R)-2-ethoxy-N-[2-(3-methoxy-4-prop-2-ynyloxy-phenyl)-ethyl]-3-phenyl-propionamide,
(R)-N-[2-(3-methoxy-4-prop-2-ynyloxy-phenyl)-ethyl]-3-phenyl-2-prop-2-ynyloxy-propionamide,
(R)-3-(4-chloro-phenyl)-N-[2-(3-methoxy-4-prop-2-ynyloxy-phenyl)-ethyl]-2-prop-2-ynyloxy-propionamide,
(R)-3-(4-chloro-phenyl)-2-methoxy-N-[2-(3-methoxy-4-prop-2-ynyloxy-phenyl)-ethyl]-propionamide,
(R)-3-(4-chloro-phenyl)-2-hydroxy-N-[2-(3-methoxy-4-prop-2-ynyloxy-phenyl)-ethyl]-propionamide,
(R)-3-(4-fluoro-phenyl)-2-hydroxy-N-[2-(3-methoxy-4-prop-2-ynyloxy-phenyl)-ethyl]-propionamide,
(R)-2-ethoxy-3-(4-fluoro-phenyl)-N-[2-(3-methoxy-4-prop-2-ynyloxy-phenyl)-ethyl]-propionamide,
(R)-3-(4-fluoro-phenyl)-N-[2-(3-methoxy-4-prop-2-ynyloxy-phenyl)-ethyl]-2-prop-2-ynyloxy-propionamide,
(R)-3-(4-bromo-phenyl)-2-hydroxy-N-[2-(3-methoxy-4-prop-2-ynyloxy-phenyl)-ethyl]-propionamide,
(R)-3-(4-bromo-phenyl)-N-[2-(3-methoxy-4-prop-2-ynyloxy-phenyl)-ethyl]-2-prop-2-ynyloxy-propionamide,
(R)-3-(4-bromo-phenyl)-2-methoxy-N-[2-(3-methoxy-4-prop-2-ynyloxy-phenyl)-ethyl]-propionamide,
(R)-3-(4-bromo-phenyl)-2-ethoxy-N-[2-(3-methoxy-4-prop-2-ynyloxy-phenyl)-ethyl]-propionamide,
(R)-N-[2-(3-methoxy-4-prop-2-ynyloxy-phenyl)-ethyl]-2-prop-2-ynyloxy-3-p-tolyl-propionamide,
(R)-3-(4-ethyl-phenyl)-N-[2-(3-methoxy-4-prop-2-ynyloxy-phenyl)-ethyl]-2-prop-2-ynyloxy-propionamide,
(R)-2-ethoxy-3-(4-ethyl-phenyl)-N-[2-(3-methoxy-4-prop-2-ynyloxy-phenyl)-ethyl]-propionamide.
(S)-2-hydroxy-N-[2-(3-methoxy-4-prop-2-ynyloxy-phenyl)-ethyl]-3-phenyl-propionamide,
(S)-2-ethoxy-N-[2-(3-methoxy-4-prop-2-ynyloxy-phenyl)-ethyl]-3-phenyl-propionamide,
(S)-N-[2-(3-methoxy-4-prop-2-ynyloxy-phenyl)-ethyl]-3-phenyl-2-prop-2-ynyloxy-propionamide,
(S)-3-(4-chloro-phenyl)-N-[2-(3-methoxy-4-prop-2-ynyloxy-phenyl)-ethyl]-2-prop-2-ynyloxy-propionamide,
(S)-3-(4-chloro-phenyl)-2-methoxy-N-[2-(3-methoxy-4-prop-2-ynyloxy-phenyl)-ethyl]-propionamide,
(S)-3-(4-chloro-phenyl)-2-hydroxy-N-[2-(3-methoxy-4-prop-2-ynyloxy-phenyl)-ethyl]-propionamide,
(S)-3-(4-fluoro-phenyl)-2-hydroxy-N-[2-(3-methoxy-4-prop-2-ynyloxy-phenyl)-ethyl]-propionamide,
(S)-2-ethoxy-3-(4-fluoro-phenyl)-N-[2-(3-methoxy-4-prop-2-ynyloxy-phenyl)-ethyl]-propionamide,
(S)-3-(4-fluoro-phenyl)-N-[2-(3-methoxy-4-prop-2-ynyloxy-phenyl)-ethyl]-2-prop-2-ynyloxy-propionamide,
(S)-3-(4-bromo-phenyl)-2-hydroxy-N-[2-(3-methoxy-4-prop-2-ynyloxy-phenyl)-ethyl]-propionamide,
(S)-3-(4-bromo-phenyl)-N-[2-(3-methoxy-4-prop-2-ynyloxy-phenyl)-ethyl]-2-prop-2-ynyloxy-propionamide,
(S)-3-(4-bromo-phenyl)-2-methoxy-N-[2-(3-methoxy-4-prop-2-ynyloxy-phenyl)-ethyl]-propionamide,
(S)-3-(4-bromo-phenyl)-2-ethoxy-N-[2-(3-methoxy-4-prop-2-ynyloxy-phenyl)-ethyl]-propionamide,
(S)-N-[2-(3-methoxy-4-prop-2-ynyloxy-phenyl)-ethyl]-2-prop-2-ynyloxy-3-p-tolyl-propionamide,
(S)-3-(4-ethyl-phenyl)-N-[2-(3-methoxy-4-prop-2-ynyloxy-phenyl)-ethyl]-2-prop-2-ynyloxy-propionamide, and
(S)-2-ethoxy-3-(4-ethyl-phenyl)-N-[2-(3-methoxy-4-prop-2-ynyloxy-phenyl)-ethyl]-propionamide.

Certain mandelic acid derivatives have been proposed for controlling plant-destructive fungi (for example in WO 94/29267 in WO 96/17840 and in PCT/EP01/05530). The action of those preparations is not, however, satisfactory in all aspects and needs of the agricultural practices. Surprisingly, with the compound structure of formula I, new kinds of microbiocides having a high level of activity have been found.

Some of the compounds of formula I are described in the literature as pharmacologically active compounds. Though they have now been found to be useful as plant protectants, these compounds will not be subject of the group of claimed novel compounds. The known pharmacologically active compounds falling within the scope of formula I have been isolated as natural products and disclosed by G. R. Pettit et al. in J. Nat. Prod, 1996, (59), pp. 927-934. In this disclosure the compounds are designated as Hemibastadinols, and have the chemical designations follows:

2-hydroxy-N-[2-(3-bromo-4-hydroxy-phenyl)-ethyl]-3-(3-bromo-4-hydroxy-phenyl)propionamide,
2-hydroxy-N-[2-(3-bromo-4-methoxy-phenyl)-ethyl]-3-(3-bromo-4-methoxy-phenyl)propionamide,
2-hydroxy-N-[2-(3-bromo-4-methoxy-phenyl)-ethyl]-3-(3,5-dibromo-4-hydroxy-phenyl)propionamide,
2-hydroxy-N-[2-(3,5-dibromo-4-hydroxy-phenyl)-ethyl]-3-(3-bromo-4-hydroxy-phenyl)propionamide,
2-hydroxy-N-[2-(3,5-dibromo-4-methoxy-phenyl)-ethyl]-3-(3-bromo-4-methoxy-phenyl)propionamide, and
2-hydroxy-N-[2-(3-bromo-4-methoxy-phenyl)-ethyl]-3-(3,5-dibromo-4-methoxy-phenyl)propionamide.

The compounds of formula I may be obtained according to one of the processes of Schemes 1 to 5:

Scheme 1:

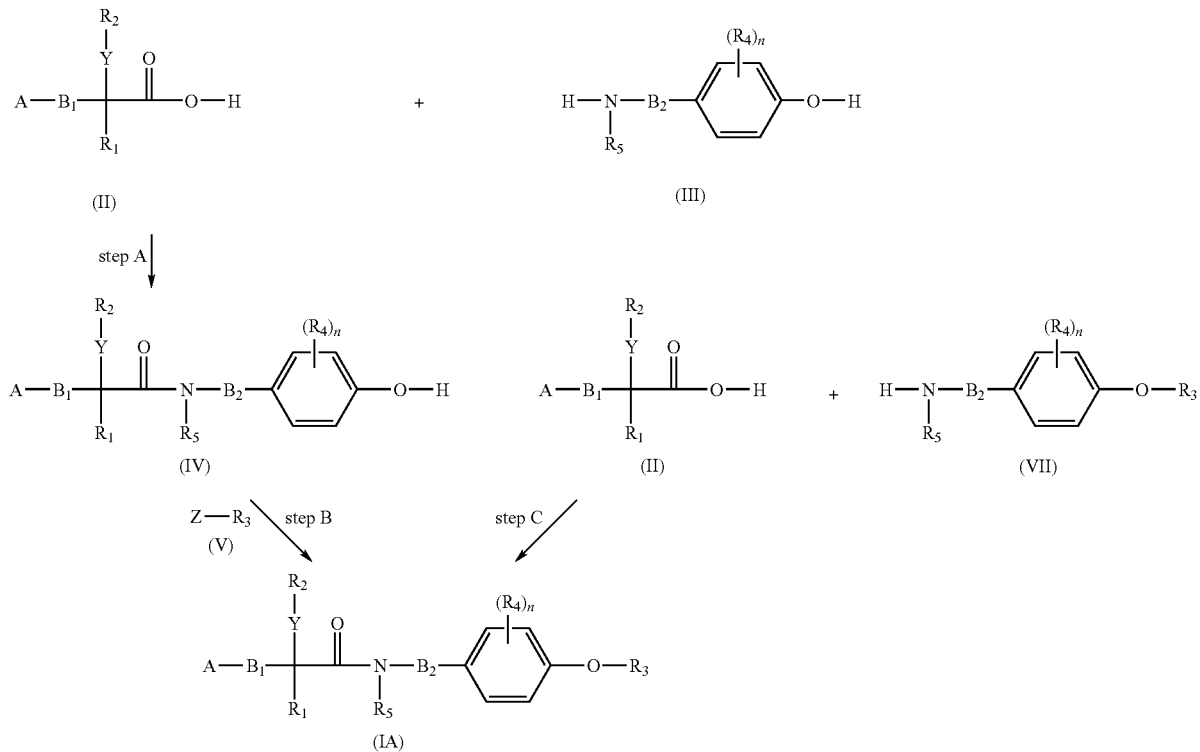

Step A: An acid of formula II or a carboxy-activated derivative of an acid of formula II wherein A, $B_1$, $R_1$, $R_2$ and Y are as defined for formula I is reacted with an amine of formula III wherein $B_2$, $R_4$ and $R_5$ are as defined for formula I, optionally in the presence of a base and optionally in the presence of a diluting agent.

Carboxy-activated derivatives of the acid of formula II are all compounds having an activated carboxyl group like an acid halide, such as an acid chloride; like symmetrical or mixed anhydrides, such as mixed anhydrides with O-alkyl-carbonates; like activated esters, such as p-nitrophenylesters or N-hydroxysuccinimidesters, or even normal esters, such as methylesters, ethylesters, n-propylesters, iso-propylesters, n-butylesters, tert-butylesters, neo-pentylesters or iso-amy-lesters; as well as in-situ-formed activated forms of the acid of formula II with condensating agents, such as dicyclohexyl-carbodiimide, carbonyldiimidazole, benzotriazol-1-yloxy-tris(dimethylamino)phosphonium hexafluorophosphate, O-benzotriazol-1-yl-N,N,N',N'-bis(pentamethylene)uro-nium hexafluorophosphate, O-benzotriazol-1-yl-N,N,N',N'-bis(tetramethylene)uronium hexafluorophosphate, O-benzo-triazol-1-yl-N,N,N',N'-tetramethyluronium hexafluorophosphate or benzotriazol-1-yloxy-tripyrrolidino-phosphonium hexafluorophosphate. The mixed anhydrides of the acids of the formula II may be prepared by reaction of an acid of formula II with chloroformic acid esters like chloroformic acid alkylesters, such as ethyl chloroformate or isobutyl chloroformate, optionally in the presence of an organic or inorganic base like a tertiary amine, such as triethylamine, N,N-diisopropylethylamine, pyridine, N-methyl-piperidine or N-methyl-morpholine.

The present reaction is preferably performed in a solvent like aromatic, non-aromatic or halogenated hydrocarbons, such as chlorohydrocarbons e.g. dichloromethane or toluene; ketones e.g. acetone; esters e.g. ethyl acetate; amides e.g. N,N-dimethylformamide; nitriles e.g. acetonitrile; or ethers e.g. diethylether, tert-butyl-methylether, dioxane or tetrahydrofuran or water. It is also possible to use mixtures of these solvents. The reaction is performed optionally in the presence of an organic or inorganic base like a tertiary amine, e.g. triethylamine, N,N-diisopropyl-ethylamine, pyridine, N-methyl-piperidine or N-methyl-morpholine, like a metal hydroxide or a metal carbonate, preferentially an alkali hydroxide or an alkali carbonate, such as lithium hydroxide, sodium hydroxide or potassium hydroxide at temperatures ranging from −80° C. to +150° C., preferentially at temperatures ranging from −40° C. to +40° C.

Step B: The compounds of formula IA may be prepared as final product by reacting a phenol of formula IV wherein A, $B_1$, $B_2$, $R_1$, $R_2$, $R_4$, $R_5$ and Y are as defined for formula I with a compound of formula V wherein $R_3$ is as defined for formula I and wherein Z is a leaving group like a halide such as chloride or bromide or a sulfonic ester such as a tosylate, mesylate or triflate.

The reaction is advantageously performed in a solvent like aromatic, non-aromatic or halogenated hydrocarbons, such as chlorohydrocarbons e.g. dichloromethane or toluene; ketones e.g. acetone or 2-butanone; esters e.g. ethyl acetate, ethers e.g. diethylether, tert-butyl-methylether, dioxane or tetrahydrofuran; amides e.g. N,N-dimethylformamide; nitriles e.g. acetonitrile; alcohols e.g. methanol, ethanol, iso-propanol, n-butanol or tert-butanol; sulfoxides e.g. dimethyl-sulfoxide or water. It is also possible to use mixtures of these solvents. The reaction is performed optionally in the presence of an organic or inorganic base like a tertiary amine, such as triethylamine, N,N-diisopropyl-ethylamine, pyridine, N-methyl-piperidine or N-methyl-morpholine, like a metal hydroxide, a metal carbonate or a metal alkoxide, preferentially an alkali hydroxide, an alkali carbonate or an alkali alkoxide, such as lithium hydroxide, sodium hydroxide, potassium hydroxide, sodium carbonate, potassium carbonate, sodium methoxide, potassium methoxide, sodium ethoxide, potassium ethoxide, sodium tert-butoxide or potassium tert-butoxide at temperatures ranging from −80° C. to +200° C., preferentially at temperatures ranging from 0° C. to +120° C.

Step C: Alternatively to step A and step B, an acid of formula II or a carboxy-activated derivative of an acid of formula II wherein A, $B_1$, $R_1$, $R_2$ and Y are as defined for formula I is reacted with an amine of formula VII wherein $B_2$, $R_3$, $R_4$ and $R_5$ are as defined for formula I under the same conditions as defined for step A, optionally in the presence of a base and optionally in the presence of a diluting agent.

Step D: A compound of formula VIII wherein $B_2$ and $R_4$ are as defined for formula I is alkylated with a compound of formula V (see Scheme 1) wherein $R_3$ and Z are as defined for Scheme 1 under the same conditions as defined for step B in Scheme 1.

Step E: A compound of formula IX wherein $B_2$, $R_3$ and $R_4$ are as defined for formula I is dehydrated to an isocyanide of formula X wherein $B_2$, $R_3$ and $R_4$ are as defined for formula I under conditions known per se (D. Seebach, G. Adam, T. Gees, M. Schiess, W. Weigang, *Chem. Ber.* 1988, 121, 507).

Step F: An isocyanide of formula X wherein $B_2$, $R_3$ and $R_4$ are as defined for formula I is reacted in a three-component Passerini reaction (J. March, *Advanced Organic Chemistry*, 5th ed., Wiley, 2001, p. 1252) with an aldehyde or ketone of formula XI, wherein A, $B_1$ and $R_1$ are as defined for formula I in the presence of a carboxylic acid XII wherein $R_6$ is hydrogen or lower alkyl, typically acetic acid, to give a Scheme 2:

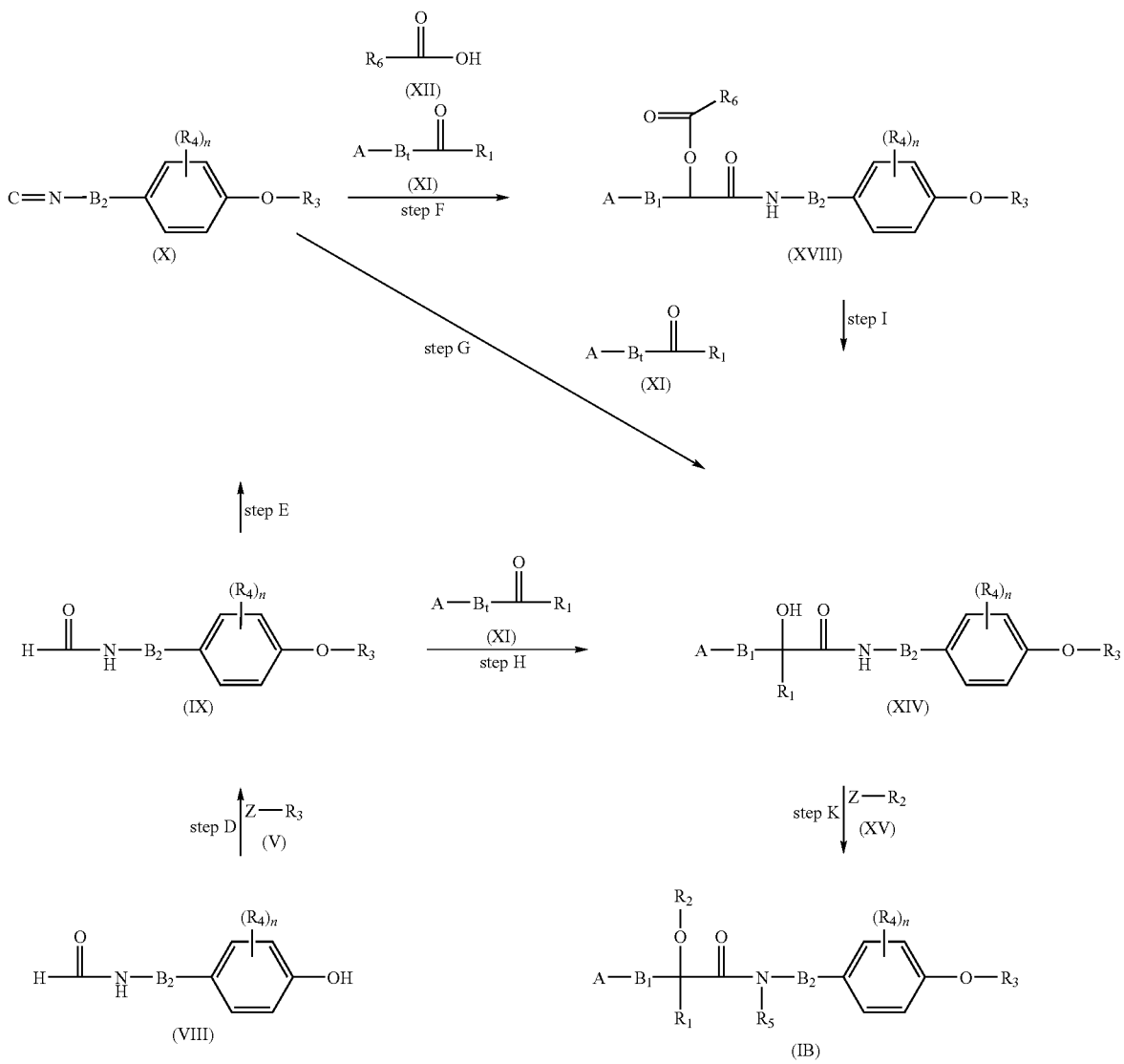

O-acyl-a-hydroxy amide of formula XIII, wherein A, $B_1$, $B_2$, $R_1$, $R_3$ and $R_4$ are as defined for formula I and $R_6$ is hydrogen or lower alkyl.

Step G: Alternatively to step F, an isocyanide of formula X wherein $B_2$, $R_3$ and $R_4$ are as defined for formula I is reacted with an aldehyde or ketone of formula XI wherein A, $B_1$ and $R_1$ are as defined for formula I in the presence of titanium tetrachloride to give an α-hydroxy amide of the formula XIV (where A, $B_1$, $B_2$, $R_1$, $R_3$ and $R_4$ have the same meaning as defined above) under conditions known per se (D. Seebach, G. Adam, T. Gees, M. Schiess, W. Weigang, *Chem. Ber.* 1988, 121, 507; O. Ort, U. Döller, W. Reissel, S. D. Lindell, T. L. Hough, D. J. Simpson, J. P. Chung, Pesticide Sci. 1997, 50, 331).

Step H: Alternatively to step E and step F, a compound of formula IX, wherein $B_2$, $R_3$ and $R_4$ are as defined for formula I is treated with one phosgene equivalent (e.g. triphosgene) and a base (e.g. triethylamine) and in a second step, without isolation of the isocyanide intermediate, is further treated with titanium tetrachloride and an aldehyde or ketone of formula XI, wherein A, $B_1$ and $R_1$ are as defined for formula I under conditions known per se (WO 96/17840) to give an α-hydroxy amide of the formula XIV, wherein A, $B_1$, $B_2$, $R_1$, $R_3$ and $R_4$ are as defined for formula I.

Step I: An O-acyl-α-hydroxy amide of formula XIII wherein A, $B_1$, $B_2$, $R_1$, $R_3$ and $R_4$ are as defined above and $R_6$ is hydrogen or lower alkyl is hydrolyzed to an α-hydroxy amide of formula XIV, wherein A, $B_1$, $B_2$, $R_1$, $R_3$ and $R_4$ are as defined for formula I under classical conditions (J. March, *Advanced Organic Chemistry*, 4th ed., Wiley, 1992).

Step K: An α-hydroxy amide of formula XIV wherein A, $B_1$, $B_2$, $R_1$, $R_3$ and $R_4$ are as defined for formula I is reacted with a compound XV wherein $R_2$ is alkyl, alkenyl or alkynyl and Z is a leaving group like a halide such as a chloride or bromide or a sulfonic ester such as a tosylate, mesylate or triflate to a compound of formula IB wherein A, $B_1$, $B_2$, $R_1$, $R_2$, $R_3$ and $R_4$ are as defined for formula I and under the same conditions as defined for step B in Scheme 1.

Scheme 3: Preparation of α-hydroxy-acids (examples of formula II):

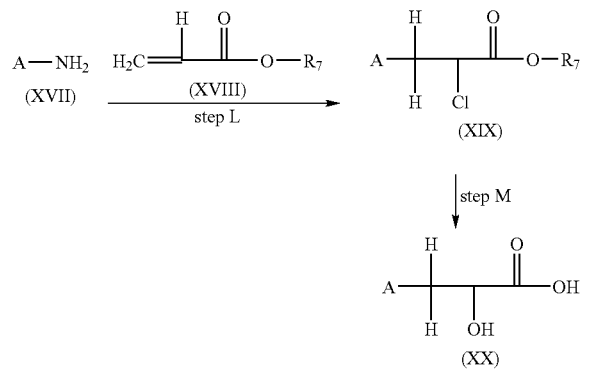

Step L: An amine of formula XVII wherein A is as defined for formula I is reacted with an acrylic acid derivative of formula XVIII, wherein $R_7$ is hydrogen or lower alkyl in the presence of sodium nitrate, hydrochloric acid and a copper salt such as copper(I) bromide or copper(I) iodide to give an α-chloro-acid derivative of formula XIX, wherein A is as defined for formula I and $R_7$ is hydrogen or lower alkyl under conditions known per se (D. Haigh, L. J. Jefcott, K. Magee, H. McNab, *J. Chem. Soc., Perkin Trans. I* 1996, 2895).

Step M: An α-chloro-acid derivative of formula XIX wherein A is as defined for formula I and $R_7$ is hydrogen or lower alkyl is then hydrolyzed to an α-hydroxy-acid of formula XX wherein A is as defined for formula I with a strong alkali base like sodium hydroxide or potassium hydroxide in the presence of a weaker base such as sodium bicarbonate, sodium carbonate, potassium carbonate or calcium carbonate under conditions known per se (D. Haigh, L. J. Jefcott, K. Magee, H. McNab, *J. Chem. Soc., Perkin Trans. I* 1996, 2895).

Scheme 4:

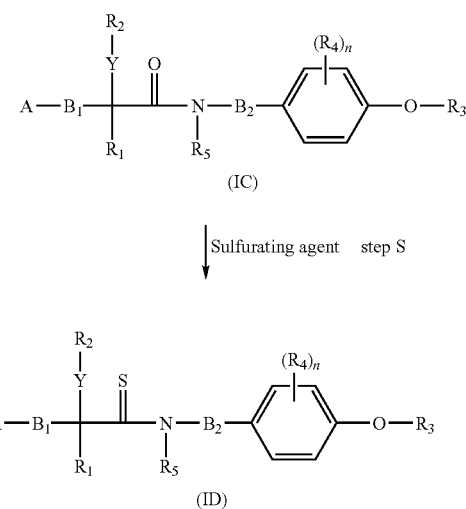

Step S: An amid of formula VI wherein A, $B_1$, $B_2$, $R_1$, $R_2$, $R_3$, $R_4$, and $R_5$ are as defined above is transformed to a thioamide of formula XXX, wherein A, $B_1$, $B_2$, $R_1$, $R_2$, $R_3$, $R_4$, and $R_5$ are as defined for formula I with a sulfurating agent, like a phosphorus sulfur compound, e.g. phosphorus pentasulfide or 2,4-bis(4-methoxyphenyl)-1,3-dithia-2,4-diphosphetane-2,4-disulfide (Lawesson's reagent), in an inert diluting agent, like an inert organic solvent such as aromatic, non aromatic or halogenated hydrocarbons, e.g. benzene, toluene, xylene, chlorobenzene or chloroform, at temperatures ranging from −80° C. to +200° C., preferably at temperatures ranging from 0 to +100° C.

Scheme 5:

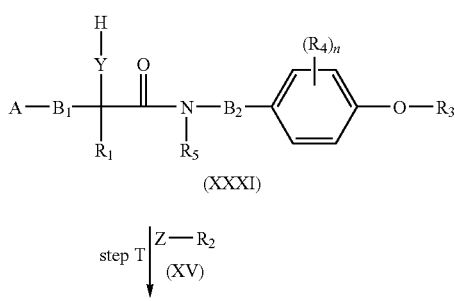

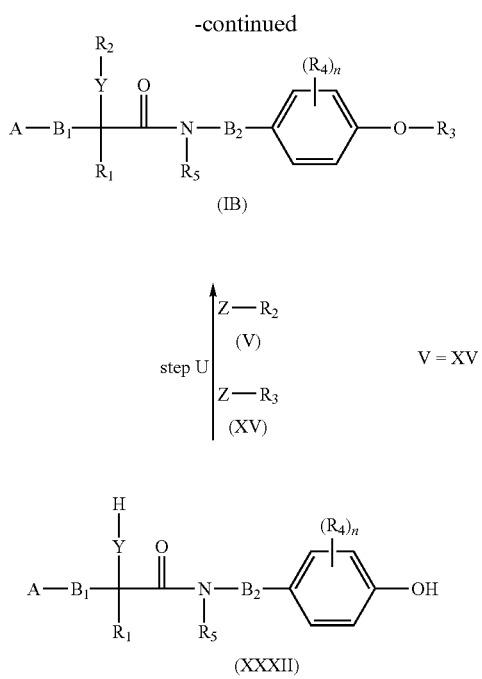

Step T: An amid of formula IB wherein A, $B_1$, $B_2$, $R_1$, $R_2$, $R_3$, $R_4$, $R_5$ and Y are as defined for formula I may be obtained by reaction of an amide of formula XXXI, wherein A, $B_1$, $B_2$, $R_1$, $R_3$, $R_4$, $R_5$ and Y are as defined for formula I with a compound of formula XV wherein $R_2$ is as defined for formula I and wherein Z is a leaving group like a halide such as chloride or bromide or a sulfonic ester such as a tosylate, mesylate or triflate under the same conditions as defined for step B in Scheme 1.

Step U: An amide of formula XXXII wherein A, $B_1$, $B_2$, $R_1$, $R_4$ and Y are as defined for formula I is reacted with a compound XV wherein $R_2$ is as defined for formula I and Z is a leaving group like a halide such as a chloride or bromide or a sulfonic ester such as a tosylate, mesylate or triflate and which is equal to a compound V wherein $R_3$ is as defined for formula I and Z is also a leaving group like a halide such as a chloride or bromide or a sulfonic ester such as a tosylate, mesylate or triflate to a compound of formula IB wherein A, $B_1$, $B_2$, $R_1$, $R_2$, $R_3$, $R_4$ and Y are as defined for formula I and under the same conditions as defined for step B in Scheme 1.

The compounds of formula I are oils or solids at room temperature and are distinguished by valuable microbiocidal properties. They can be used in the agricultural sector or related fields preventatively and curatively in the control of plant-destructive microorganisms. The compounds of formula I according to the invention are distinguished at low rates of concentration not only by outstanding microbiocidal, especially fungicidal, activity but also by being especially well tolerated by plants.

Surprisingly, it has now been found that the compounds of formula I have for practical purposes a very advantageous microbiocidal spectrum in the control of phytopathogenic microorganisms, especially fungi. They possess very advantageous curative and preventive properties and are used in the protection of numerous crop plants. With the compounds of formula I it is possible to inhibit or destroy phytopathogenic microorganisms that occur on various crops of useful plants or on parts of such plants (fruit, blossom, leaves, stems, tubers, roots), while parts of the plants which grow later also remain protected, for example, against phytopathogenic fungi.

The novel compounds of formula I prove to be effective against specific genera of the fungus class Fungi imperfecti (e.g. *Cercospora*), *Basidiomycetes* (e.g. *Puccinia*) and *Ascomycetes* (e.g. *Erysiphe* and *Venturia*) and especially against Oomycetes (e.g. *Plasmopara, Peronospora, Pythium* and *Phytophthora*). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Also included is a method of treating plants which is distinguished by the application of the novel compounds of formula I or of the novel compositions.

Target crops to be protected within the scope of this invention comprise, for example, the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally used in the form of compositions and can be applied to the area or plant to be treated simultaneously or in succession with other active ingredients. Those other active ingredients may be fertilisers, micronutrient donors or other preparations that influence plant growth. It is also possible to use selective herbicides or insecticides, fungicides, bactericides, nematicides, molluscicides or mixtures of several of those preparations, if desired together with further carriers, surfactants or other application-promoting adjuvants customarily employed in formulation technology.

The compounds of formula I can be mixed with other fungicides, resulting in some cases in unexpected synergistic activities. Such mixtures are not limited to two active ingredients (one of formula I and one of the list of other fungicides), but to the contrary many comprise more than one active ingredient of the component of formula I and more than one other fungicide. Mixing components which are particularly suited for this purpose include e.g. azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triconazole; pyrimidinyl carbinoles, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin), BAS 520; dithiocarbamates, such as ferbam, mancozeb, maneb, metiram, propineb, thiram, zineb, ziram; N-halomethylthiotetrahydrophthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxinecopper; nitrophenol-derivatives, such as dinocap, nitrothal-isopropyl; organo-p-derivatives, such as edifenphos, iprobenphos, isoprothiolane, phosdiphen, pyrazophos, tolclofos-methyl; various others, such as acibenzolar-S-methyl, anilazine, benthiavalicarb, blasticidin-S, chinomethionate, chloroneb, chlorothalonil, cyflufenamid, cymoxanil, dichlone, diclomezine, dicloran, diethofencarb, dimethomorph, SYP-LI90 (proposed name: flumorph), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, IKF-916 (cyazofamid), kasugamycin, methasulfocarb, metrafenone, nicobifen (new proposal: boscalid), pencycuron, phthalide, polyoxins, probenazole, propamocarb, pyroquilon, quinoxyfen, quintozene, sulfur, triazoxide, tricyclazole, triforine, validamycin, zoxamide (RH7281).

In the above mentioned mixtures, the mixture ratio of the active ingredients is so selected that it reaches optional control of the phytopathogenic microorganism on the host plants. This ratio is in general between 100:1 and 1:100, more preferably between 10:1 and 1:10 of a compound of formula I vis-à-vis the second fungicide. The mixtures may not only comprise one of the listed combinational active ingredients, but may comprise more than one additional active ingredients selected from that specified group, thus forming for example 3-way- or even 4-way-mixtures.

Suitable carriers and surfactants may be solid or liquid and correspond to the substances ordinarily employed in formulation technology, such as e.g. natural or regenerated mineral substances, solvents, dispersants, wetting agents, tackifiers, thickeners, binders or fertilisers. Such carriers and additives are described, for example, in WO 95/30651.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to seed grains (coating) either by impregnating the grains with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, diluter emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the compound(s) (active ingredient(s)) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.01 to 99% by weight, preferably 0.1 to 95% by weight, of a compound of formula I, 99.99 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilisers or other active ingredients for obtaining special effects.

The following Examples illustrate the described invention, without limiting the scope thereof in any way. Temperatures are given in degrees Celsius. Ph stands for phenyl.

PREPARATION EXAMPLES

Example E1

N-[2-(3-Methoxy-4-prop-2-ynyloxy-phenyl)-ethyl]-3-phenyl-2-prop-2-ynyloxy-butyramide (E1.24)

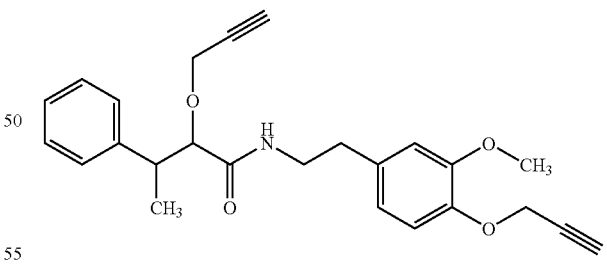

a) N-[2-(4-Hydroxy-3-methoxy-phenyl)-ethyl]-formamide

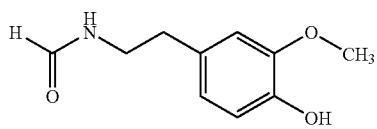

Formic acid (230 g, 5.0 mol) is added dropwise to acetic anhydride (383 g, 3.75 mol) at 0° C. This mixture is stirred for 2 hours at +55° C. and subsequently cooled again to 0° C. Tetrahydrofuran (500 ml) is added at this temperature followed by 4-(2-amino-ethyl)-2-methoxyphenol hydrochloride (50 g, 0.25 mol). The resulting white suspension is stirred for 18 hours at +75° C., changing into a yellow solution. The reaction mixture is evaporated and the residue is submitted to flash-chromatography to yield N-[2-(4-hydroxy-3-methoxyphenyl)-ethyl]-formamide.

¹H-NMR (300 MHz, CDCl₃): 2.85 (t, 2H, CH₂CH₂), 3.57 (t, 2H, CH₂CH₂), 3.82 (s, 3H, OCH₃), 5.69 (bs, 1H, NH), 6.67-7.09 (m, 3H, CH arom.), 8.12 (s, 1H, CHO).

b) N-[2-(3-Methoxy-4-prop-2-ynyloxy-phenyl)-ethyl]-formamide

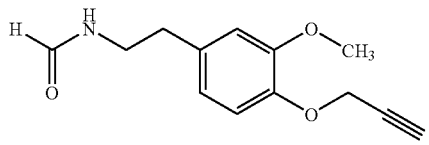

Sodium methoxide (32 ml of a 5.4 M solution in methanol, 0.17 mol) is added to a solution of N-[2-(4-hydroxy-3-methoxy-phenyl)-ethyl]-formamide (32 g, 0.16 mol) in methanol (400 ml). Propargyl bromide (20 g, 0.17 mol) is added and the mixture is refluxed for 4 hours. After evaporation the residue is taken up in ethyl acetate (400 ml) and washed with water (2×200 ml). The organic layer is dried over magnesium sulfate and evaporated. The residue is submitted to flash-chromatography to give the N-[2-(3-methoxy-4-prop-2-ynyloxy-phenyl)-ethyl]-formamide.

¹H-NMR (300 MHz, CDCl₃): 2.44 (t, 1H, C≡CH), 2.73 (t, 2H, CH₂CH₂), 3.51 (t, 2H, CH₂CH₂), 3.82 (s, 3H, OCH₃), 4.69 (m, 2H, OCH₂), 5.53 (bs, 1H, NH), 6.62-6.95 (m, 3H, CH arom.), 8.09 (s, 1H, CHO).

c) 2-Hydroxy-N-[2-(3-methoxy-4-prop-2-ynyloxy-phenyl)-ethyl]-3-phenyl-butyramide (E1.23)

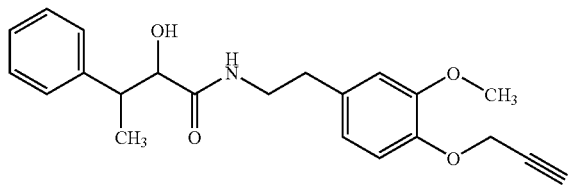

N-[2-(3-Methoxy-4-prop-2-ynyloxy-phenyl)-ethyl]-formamide (8.0 g, 34 mmol) and triethylamine (8.3 g, 82 mmol) are dissolved in dichloromethane (80 ml). Bis(trichloromethyl)carbonate (triphosgene, 4.0 g, 14 mmol) in dichloromethane (40 ml) is added at +5° C. The mixture is stirred for 4 hours at +5° C. and then cooled to −78° C. A solution of titanium tetrachloride (7.0 g, 38 mmol) in dichloromethane (70 ml) is added and the mixture is stirred for 2 hours at −40° C. 2-Phenylpropionaldehyde (4.8 g, 36 mmol) in dichloromethane (50 ml) is added dropwise and the mixture is stirred for 17 hours at room temperature. The mixture is hydrolysed with 5N HCl (25 ml), stirred 30 minutes at room temperature and washed with water. After evaporation of the organic layer the residue is submitted to flash-chromatography (ethyl acetate/hexane 6:3) to give 2-hydroxy-M[2-(3-methoxy-4-prop-2-ynyloxy-phenyl)-ethyl]-3-phenyl-butyramide (E1.23).

¹H-NMR (300 MHz, CDCl₃): 1.26 (d, 3H, CH₃), 2.52 (t, 1H, C≡CH), 2.76 (t, 2H, CH₂CH₂), 3.36-3.61 (m, 3H, CH, CH₂CH₂), 3.90 (s, 3H, OCH₃), 4.19 (m, 1H, CHO), 4.78 (d, 2H, OCH₂), 6.71-7.38 (m, 9H, NH, CH arom.).

c) A 80% solution of propargyl bromide in toluene (1.2 g, 7.8 mmol) is added slowly at room temperature to a mixture of 2-hydroxy-N-[2-(3-methoxy-4-prop-2-ynyloxy-phenyl) ethyl]-3-phenyl-butyramide (2.4 g, 6.5 mmol), 30% sodium hydroxide solution (6.0 ml, 33 mmol) and catalytic amounts of tetrabutylammonium bromide (50 mg) in 25 ml of dichloromethane. The reaction is stirred for 16 hours at +40° C. Subsequently the mixture is evaporated and the residue is diluted with water and dichloromethane. The phases are separated and the aqueous phase is extracted three times with dichloromethane. The combined organic layer is washed with brine, dried over sodium sulfate and evaporated. The remaining oil is purified by chromatography on silica gel (ethyl acetate/hexane 1:1) to yield N-[2-(3-methoxy-4-prop-2-ynyloxy-phenyl)-ethyl]-3-phenyl-2-prop-2-ynyloxy-butyramide (E1.24).

¹H-NMR (300 MHz, CDCl₃): 1.02 (d, 3H, CH₃), 2.08 (t, 1H, C≡CH), 2.27 (t, 1H, C≡CH), 2.53 (q, 2H, CH₂CH₂), 3.18 (dq, 1H, CH), 3.30 (q, 2H, CH₂CH₂), 3.41 (dd, 1H, OCH₂), 3.65 (s, 3H, OCH₃), 3.72 (dd, 1H, OCH₂), 3.90 (q, 1H, CHO), 4.51 (d, 2H, OCH₂), 6.49-7.10 (m, 9H, NH, CH arom.).

Example E2

2-Allyloxy-N-[2-(3-methoxy-4-prop-2-ynyloxy-phenyl)-ethyl]-3-p-tolyl-propionamide (E1.17)

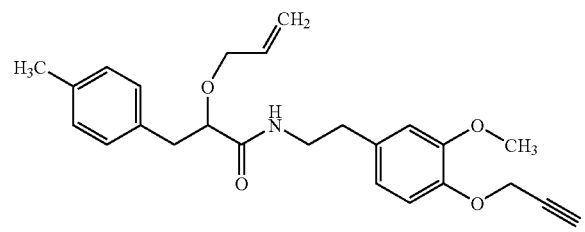

a) 2-Chloro-3-p-tolyl-propionic acid methyl ester

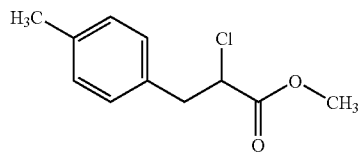

A solution of sodium nitrite (16.5 g, 0.24 mol) in 50 ml of water is slowly added to a mechanically stirred, acetone-dry ice cooled suspension of p-toluidine (23.5 g, 0.22 mol), 250 ml of acetone and 50 ml of concentrated hydrochloric acid in such manner, that the reaction temperature does not exceed +5° C. The mixture is stirred for 1 hour at +5° C. and then 100 ml of methyl acrylate are added. The suspension is then warmed to +30° C. Copper(I) iodide (1 g, 5 mmol) is added portionwise over 30 minutes such that the temperature of the reaction mixture does not exceed +35° C., and the stirring is continued for an additional 30 minutes at this temperature. The solvent is evaporated under reduced pressure, the residue is diluted with water and extracted with dichloromethane. The combined organic layer is washed with water, dried over magnesium sulfate and evaporated. The residue is purified by chromatography on silica gel (ethyl acetate/hexane 9:1) to obtain 2-chloro-3-p-tolyl-propionic acid methyl ester.

$^1$H-NMR (300 MHz, CDCl$_3$): 2.14 (s, 3H, CH$_3$), 2.94 (dd, 1H, CH$_2$), 3.15 (dd, 1H, CH$_2$), 3.56 (s, 3H, OCH$_3$), 4.23 (t, 1H, CHCl), 6.89-6.97 (m, 4H).

b) 2-Hydroxy-3->tolyl-Propionic acid

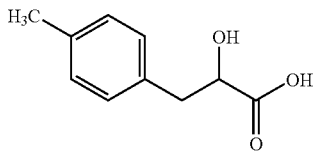

A mechanically stirred suspension of 2-chloro-3-p-tolyl-propionic acid methyl ester (23 g, 0.1 mol), calcium carbonate (11 g, 0.1 mol), sodium hydroxide (5.5 g, 0.11 mol), 200 ml of dioxane and 300 ml of water is heated at reflux for 16 hours. After cooling to room temperature, 1.3 l of 2 N hydrochloric acid are added and the mixture is extracted with ethyl acetate. The combined organic layer is washed with brine, dried over magnesium sulfate and evaporated to yield 2-hydroxy-3-p-tolyl-propionic acid, which is sufficiently pure to be used in the next step.

$^1$H-NMR (300 MHz, CDCl$_3$): 2.25 (s, 3H, CH$_3$), 2.89 (dd, 1H, CH$_2$), 3.10 (dd, 1H, CH$_2$), 4.40 (q, 1H, CHCl), 7.00-7.07 (m, 4H).

c) 2-Hydroxy-N-[2-(3-methoxy-4-prop-2-ynyloxy-phenyl)-ethyl]-3-tolyl-propionamide (E1.16)

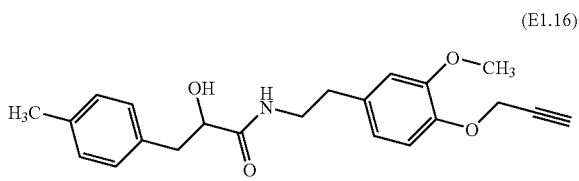

2-(3-Methoxy-4-prop-2-ynyloxy-phenyl)-ethylamine hydrochloride (11.5 g, 47 mmol) and N,N-diisopropylethylamine (23 g, 0.18 mol) are dissolved in 100 ml of N,N-dimethylformamide. To this solution 2-hydroxy-3-p-tolyl-propionic acid (8.1 g, 45 mmol) and (benzotriazol-1-yloxy)-tris-(dimethylamino)-phosphonium hexafluorophosphate (22 g, 49 mmol) are added successively. The reaction mixture is stirred for 16 hours at room temperature, subsequently poured on ice-water and extracted several times with ethyl acetate. The combined organic layer is washed with brine, dried over sodium sulfate and evaporated in vacuum. The remaining oil is purified by chromatography on silicagel (ethyl acetate/hexane 1:1) to afford 2-hydroxy-N-[2-(3-methoxy-4-prop-2-ynyloxy-phenyl)-ethyl]-3-p-tolyl-propionamide (E1.16).

$^1$H-NMR (300 MHz, CDCl$_3$): 2.32 (s, 3H, CH$_3$), 2.50 (t, 1H, C≡CH), 2.73 (dt, 2H, CH$_2$CH$_2$), 2.86(dd, 1H, CH$_2$), 3.19(dd, 1H, CH$_2$), 3.51 (q, 2H, CH$_2$CH$_2$), 3.85 (s, 3H, OCH$_3$), 4.25 (q, 1H, CHOH), 4.74 (d, 2H, OCH$_2$), 6.59 (bs, 1H, NH), 6.67-7.29 (m, 7H, CH arom.). M.p.: 85° C.

d) Allyl bromide (1.2 g, 10 mmol) is added slowly at room temperature to a mixture of 2-hydroxy-N-[2-(3-methoxy-4-prop-2-ynyloxy-phenyl)-ethyl]-3-p-tolyl-propionamide (3.0 g, 8.2 mmol), 30% sodium hydroxide solution (6.5 ml, 41 mmol) and catalytic amounts of tetrabutylammonium bromide (50 mg) in 30 ml of dichloromethane. The reaction is stirred for 16 hours at +40° C. Subsequently the mixture is evaporated and the residue is diluted with water and dichloromethane. The phases are separated and the aqueous phase is extracted three times with dichloromethane. The combined organic layer is washed with brine, dried over sodium sulfate and evaporated. The remaining oil is purified by chromatography on silica gel (ethyl acetate/hexane 1:1) to give 2-allyloxy-N-[2-(3-methoxy-4-prop-2-ynyloxy-phenyl)-ethyl]-3-p-tolyl-propionamide (E1.17).

$^1$H-NMR (300 MHz, CDCl$_3$): 2.32 (s, 3H, CH$_3$), 2.51 (t, 1H, C≡CH), 2.70 (dt, 2H, CH$_2$CH$_2$), 2.89 (dd, 1H, CH$_2$), 3.12 (dd, 1H, CH$_2$), 3.50 (q, 2H, CH$_2$CH$_2$), 3.86 (s, 3H, OCH$_3$), 3.99 (q, 1H, CHOH), 4.73 (d, 2H, OCH$_2$), 5.08-5.15 (m, 2H, C═CH$_2$), 5.69 (dt, 1H, CH═C), 6.52 (bs, 1H, NH), 6.62-7.15 (m, 7H, CH arom.).

According to the procedures of Examples E1 and E2 the compounds listed in table E1 are obtained.

TABLE E1

| No. | A | B | R$_2$ | $^1$H-NMR |
|---|---|---|---|---|
| E1.01 | Ph | —CH$_2$— | H | 2.49 (t, 1H), 2.72 (dt, 2H), 2.86 (dd, 1H), 3.20 (dd, 1H), 3.48 (q, 2H), 3.84 (s, 3H), 4.27 (q, 1H), 4.72 (d, 2H), 6.63-7.34 (m, 8H). |
| E1.02 | Ph | —CH$_2$— | CH$_2$CH$_3$ | 0.96 (t, 3H), 2.42 (t, 1H), 2.60 (m, 2H), 2.80 (dd, 1H), 3.06 (dd, 1H), 3.23-3.41 (m, 4H), 3.79 (s, 3H), 3.82 (q, 1H), 4.66(d, 2H), 6.55-7.23 (m, 8H). |
| E1.03 | Ph | —CH$_2$— | CH$_2$C═CH | 2.40 (t, 1H), 2.51 (t, 1H), 2.68 (m, 2H), 2.96 (dd, 1H), 3.20 (dd, 1H), 3.49 (q, 2H), 3.88 (s, 3H), 3.93 (dd, 1H), 4.05 (dd, 1H), 4.18 (q, 1H), 4.77 (d, 2H), 6.65-7.31 (m, 8H). |

TABLE E1-continued

Structure: A—B₁—C(OR₂)(H)—C(=O)—NH—CH₂—CH(H)—(3-methoxy-4-propargyloxyphenyl)

| No. | A | B | R₂ | ¹H-NMR |
|---|---|---|---|---|
| E1.04 | 4-F-Ph | —CH₂— | H | 2.43 (t, 1H), 2.62 (dt, 2H), 2.78 (dd, 1H), 3.07 (dd, 1H), 3.40 (q, 2H), 3.78 (s, 3H), 4.17 (q, 1H), 4.66 (d, 2H), 6.59-7.13 (m, 7H). |
| E1.05 | 4-F-Ph | —CH₂— | CH₂CH₃ | 0.97 (t, 3H), 2.42 (t, 1H), 2.61 (m, 2H), 2.79 (dd, 1H), 3.02 (dd, 1H), 3.28 (q, 2H), 3.40 (q, 2H), 3.78-3.82 (m, 4H), 4.67 (d, 2H), 6.57-7.12 (m, 7H). |
| E1.06 | 4-F-Ph | —CH₂— | CH₂C≡CH | 2.32 (t, 1H), 2.43 (t, 1H), 2.62 (m, 2H), 2.88 (dd, 1H), 3.05 (dd, 1H), 3.39 (q, 2H), 3.80 (s, 3H), 3.88 (dd, 1H), 3.97 (dd, 1H), 4.06 (q, 1H), 4.68 (d, 2H), 6.58-7.14 (m, 7H). |
| E1.07 | 4-Cl-Ph | —CH₂— | H | 2.31 (t, 1H), 2.54 (dt, 2H), 2.68 (dd, 1H), 2.97 (dd, 1H), 3.30 (q, 2H), 3.68 (s, 3H), 4.07 (q, 1H), 4.54 (d, 2H), 6.48-7.10 (m, 7H). |
| E1.08 | 4-Cl-Ph | —CH₂— | CH₃ | 2.50 (t, 1H), 2.69 (m, 2H), 2.89 (dd, 1H), 3.09 (dd, 1H), 3.27 (s, 3H), 3.48 (q, 2H), 3.82 (q, 1H), 3.90 (s, 3H), 4.75 (d, 2H), 6.62-7.28 (m, 7H). |
| E1.09 | 4-Cl-Ph | —CH₂— | CH₂CH=CH₂ | 2.67 (t, 1H), 2.85 (m, 2H), 3.05 (dd, 1H), 3.24 (dd, 1H), 3.63 (q, 2H), 4.03 (s, 3H), 4.12 (q, 1H), 4.92 (d, 2H), 5.26-5.32 (m, 2H), 5.82 (dt, 1H), 6.78-7.43 (m, 7H). |
| E1.10 | 4-Cl-Ph | —CH₂— | CH₂C≡CH | 2.40 (t, 1H), 2.51 (t, 1H), 2.71 (m, 2H), 2.95 (dd, 1H), 3.14 (dd, 1H), 3.49 (q, 2H), 3.89 (s, 3H), 3.99 (dd, 1H), 4.06 (dd, 1H), 4.15 (q, 1H), 4.75 (d, 2H), 6.62-7.28 (m, 7H). |
| E1.11 | 4-Br-Ph | —CH₂— | H | 2.52 (t, 1H), 2.72 (dt, 2H), 2.83 (dd, 1H), 3.14 (dd, 1H), 3.50 (q, 2H), 3.85 (s, 3H), 4.28 (q, 1H), 4.76 (d, 2H), 6.68-7.48 (m, 7H). |
| E1.12 | 4-Br-Ph | —CH₂— | CH₃ | 2.43 (t, 1H), 2.62 (m, 2H), 2.80 (dd, 1H), 2.99 (dd, 1H), 3.18 (s, 3H), 3.40 (dq, 2H), 3.73 (q, 2H), 3.81 (s, 3H), 4.70 (d, 2H), 6.57-7.33 (m, 7H). |
| E1.13 | 4-Br-Ph | —CH₂— | CH₂CH₃ | 1.10 (t, 3H), 2.32 (t, 1H), 2.52 (dt, 2H), 2.67 (dd, 1H), 2.98 (dd, 1H), 3.27-3.44 (m, 4H), 3.70 (s, 3H), 4.08 (m, 1H), 4.58 (d, 2H), 6.48-7.28 (m, 7H). |
| E1.14 | 4-Br-Ph | —CH₂— | CH₂CH=CH₂ | 2.42 (t, 1H), 2.61 (m, 2H), 2.80 (dd, 1H), 2.98 (dd, 1H), 3.40 (q, 2H), 3.78 (s, 3H), 3.89 (q, 1H), 4.68 (d, 2H), 5.02-5.10 (m, 2H), 5.59 (dt, 1H), 6.55-7.34 (m, 7H). |
| E1.15 | 4-Br-Ph | —CH₂— | CH₂C≡CH | 2.41 (t, 1H), 2.51 (t, 1H), 2.68 (m, 2H), 2.91 (dd, 1H), 3.10 (dd, 1H), 3.47 (q, 2H), 3.88 (s, 3H), 3.96 (dd, 1H), 4.07 (dd, 1H), 4.13 (m, 1H), 4.78 (d, 2H), 6.68-7.42 (m, 7H). |
| E1.16 | 4-CH₃-Ph | —CH₂— | H | 2.32 (s, 3H), 2.50 (t, 1H), 2.73 (dt, 2H), 2.86 (dd, 1H), 3.19 (dd, 1H), 3.51 (q, 2H), 3.85 (s, 3H), 4.25 (q, 1H), 4.74 (d, 2H), 6.67-7.29 (m, 7H). |
| E1.17 | 4-CH₃-Ph | —CH₂— | CH₂CH=CH₂ | 2.32 (s, 3H), 2.51 (t, 1H), 2.70 (dt, 2H), 2.89 (dd, 1H), 3.12 (dd, 1H), 3.50 (q, 2H), 3.86 (s, 3H), 3.99 (q, 1H), 4.73 (d, 2H), 5.08-5.15 (m, 2H), 5.69 (dt, 1H), 6.62-7.15 (m, 7H). |
| E1.18 | 4-CH₃-Ph | —CH₂— | CH₂C≡CH | 2.33 (s, 3H), 2.40 (t, 1H), 2.52 (t, 1H), 2.79 (m, 2H), 2.93 (dd, 1H), 3.15 (dd, 1H), 3.48 (q, 2H), 3.87 (s, 3H), 3.93 (dd, 1H), 4.04 (dd, 1H), 4.16 (m, 1H), 4.75 (d, 2H), 6.66-7.16 (m, 7H). |
| E1.19 | 4-CH₃CH₂-Ph | —CH₂— | H | 1.25 (t, 3H), 2.51 (t, 1H), 2.60-2.84 (m, 5H), 3.21 (dd, 1H), 3.53 (q, 2H), 3.87 (s, 3H), 4.28 (q, 1H), 4.74 (d, 2H), 6.65-7.27 (m, 7H). |

TABLE E1-continued

| No. | A | B | R₂ | ¹H-NMR |
|---|---|---|---|---|
| E1.20 | 4-CH$_3$CH$_2$-Ph | —CH$_2$— | CH$_2$CH$_3$ | 0.86 (1, 3H), 1.08 (t, 3H), 2.33 (t, 1H), 2.48 (q, 2H), 2.57 (t, 2H), 2.69 (dd, 1H), 2.95-3.07 (m, 3H), 3.33 (q, 2H), 3.70 (s, 3H), 4.09 (q, 1H), 4.60 (d, 2H), 6.49-7.10 (m, 7H). |
| E1.21 | 4-CH$_3$CH$_2$-Ph | —CH$_2$— | CH$_2$CH=CH$_2$ | 1.24 (t, 3H), 2.51 (1, 1H), 2.57-2.76 (m, 4H), 2.90 (dd, 1H), 3.12 (dd, 1H), 3.48 (q, 2H), 3.85 (s, 3H), 3.99 (q, 1H), 4.76 (d, 2H), 5.07-5.15 (m, 2H), 5.68(dt, 1H), 6.61-7.28 (m, 7H). |
| E1.22 | 4-CH$_3$CH$_2$-Ph | —CH$_2$— | CH$_2$C≡CH | 1.22 (t, 3H), 2.40 (t, 1H), 2.51 (t, 1H), 2.58-2.71 (m, 4H), 2.93 (dd, 1H), 3.16 (dd, 1H), 3.49 (q, 2H), 3.88 (s, 3H), 3.94 (dd, 1H), 4.06 (dd, 1H), 4.18 (q, 1H), 4.75 (d, 2H), 6.63-7.18 (m, 7H). |
| E1.23 | Ph | —CH(CH$_3$)— | H | 1.26 (d, 3H), 2.52 (t, 1H), 2.76 (t, 1H), 3.36-3.61 (m, 3H), 3.90 (s, 3H), 4.19 (m, 1H), 4.78 (d, 2H), 6.71-7.38 (m, 8H). |
| E1.24 | Ph | —CH(CH$_3$)— | CH$_2$C≡CH | 1.02 (d, 3H), 2.08 (t, 1H), 2.27 (t, 1H), 2.53 (q, 2H), 3.18 (dq, 1H), 3.30 (q, 2H), 3.41 (dd, 1H), 3.65 (s, 3H), 3.72 (dd, 1H), 3.90 (g, 1H), 4.51 (d, 2H), 6.49-7.10 (m, 8H). |

(Ph designates phenyl)

Analogously to the above examples the compounds of tables 1 to 3 are obtained.

TABLE 1

Compounds represented by the Formula I.01

(I.01)

wherein the combination of the groups A, R$_1$, R$_2$, R$_3$, R$_4$ and X corresponds each to one row in table A.

TABLE 2

Compounds represented by the Formula I.02

(I.02)

wherein the combination of the groups A, R$_1$, R$_2$, R$_3$, R$_4$ and X corresponds each to one row in table A.

TABLE 3

Compounds represented by the Formula I.03

(I.03)

wherein the combination of the groups A, R$_1$, R$_2$, R$_3$, R$_4$ and X corresponds each to one row in table A.

TABLE A

| No. | A | R$_1$ | R$_2$ | R$_3$ | R$_4$ | X |
|---|---|---|---|---|---|---|
| 001 | Ph | H | H | CH$_2$C≡CH | OCH$_3$ | O |
| 002 | Ph | H | CH$_3$ | CH$_2$C=OH | OCH$_3$ | O |
| 003 | Ph | H | CH$_2$CH$_3$ | OCH$_3$ | | O |
| 004 | Ph | H | CH$_2$O=CH | CH$_3$ | OCH$_3$ | O |

TABLE A-continued

| No. | A | $R_1$ | $R_2$ | $R_3$ | $R_4$ | X |
|---|---|---|---|---|---|---|
| 005 | Ph | H | $CH_2C\equiv CH$ | $CH_2CH_3$ | $OCH_3$ | O |
| 006 | Ph | H | $CH_2C\equiv OH$ | $CH_2C\equiv CH$ | $OCH_3$ | O |
| 007 | Ph | $CH_3$ | $CH_2OECH$ | $CH_2C\equiv CH$ | $OCH_3$ | O |
| 008 | Ph | H | $CH_2C\equiv CH$ | $CH_2C\equiv OH$ | $CH_3$ | O |
| 009 | Ph | H | $CH_2C\equiv CH$ | $CH_2C\equiv OH$ | $OCH_3$ | S |
| 010 | 4-F-Ph | H | H | $CH_2C\equiv CH$ | $OCH_3$ | O |
| 011 | 4-F-Ph | H | $CH_3$ | $CH_2C\equiv CH$ | $OCH_3$ | O |
| 012 | 4-F-Ph | H | $CH_2CH_3$ | $CH_2C\equiv CH$ | $OCH_3$ | O |
| 013 | 4-F-Ph | H | $CH_2C\equiv CH$ | $CH_3$ | $OCH_3$ | O |
| 014 | 4-F-Ph | H | $CH_2C\equiv CH$ | $CH_2CH_3$ | $OCH_3$ | O |
| 015 | 4-F-Ph | H | $CH_2C\equiv CH$ | $CH_2C\equiv CH$ | $OCH_3$ | O |
| 016 | 4-F-Ph | $CH_3$ | $CH_2C\equiv CH$ | $CH_2C\equiv CH$ | $OCH_3$ | O |
| 017 | 4-F-Ph | H | $CH_2C\equiv CH$ | $CH_2C\equiv CH$ | $CH_3$ | O |
| 018 | 4-F-Ph | H | $CH_2C\equiv CH$ | $CH_2C\equiv CH$ | $OCH_3$ | S |
| 019 | 4-Cl-Ph | H | H | $CH_2C\equiv CH$ | $OCH_3$ | O |
| 020 | 4-Cl-Ph | H | $CH_3$ | $CH_2C\equiv CH$ | $OCH_3$ | O |
| 021 | 4-Cl-Ph | H | $CH_2CH_3$ | $CH_2C\equiv CH$ | $OCH_3$ | O |
| 022 | 4-Cl-Ph | H | $CH_2C\equiv CH$ | $CH_3$ | $OCH_3$ | O |
| 023 | 4-Cl-Ph | H | $CH_2C\equiv CH$ | $CH_2CH_3$ | $OCH_3$ | O |
| 024 | 4-Cl-Ph | H | $CH_2O\equiv CH$ | $CH_2C\equiv CH$ | $OCH_3$ | O |
| 025 | 4-Cl-Ph | $CH_3$ | $CH_2C\equiv CH$ | $CH_2C\equiv CH$ | $OCH_3$ | O |
| 026 | 4-Cl-Ph | H | $CH_2C\equiv CH$ | $CH_2C\equiv CH$ | $CH_3$ | O |
| 027 | 4-Cl-Ph | H | $CH_2C\equiv CH$ | $CH_2C\equiv CH$ | $OCH_3$ | S |
| 028 | 4-Br-Ph | H | H | $CH_2C\equiv CH$ | $OCH_3$ | O |
| 029 | 4-Br-Ph | H | $CH_3$ | $CH_2C\equiv CH$ | $OCH_3$ | O |
| 030 | 4-Br-Ph | H | $CH_2CH_3$ | $CH_2C\equiv CH$ | $OCH_3$ | O |
| 031 | 4-Br-Ph | H | $CH_2C\equiv CH$ | $CH_3$ | $OCH_3$ | O |
| 032 | 4-Br-Ph | H | $CH_2C\equiv CH$ | $CH_2CH_3$ | $OCH_3$ | O |
| 033 | 4-Br-Ph | H | $CH_2C\equiv CH$ | $CH_2C\equiv CH$ | $OCH_3$ | O |
| 034 | 4-Br-Ph | $CH_3$ | $CH_2C\equiv CH$ | $CH_2C\equiv CH$ | $OCH_3$ | O |
| 035 | 4-Br-Ph | H | $CH_2C\equiv CH$ | $CH_2C\equiv CH$ | $CH_3$ | O |
| 036 | 4-Br-Ph | H | $CH_2C\equiv CH$ | $CH_2C\equiv CH$ | $OCH_3$ | S |
| 037 | $4-CH_3$-Ph | H | H | $CH_2C\equiv CH$ | $OCH_3$ | O |
| 038 | $4-CH_3$-Ph | H | $CH_3$ | $CH_2C\equiv CH$ | $OCH_3$ | O |
| 039 | $4-CH_3$-Ph | H | $CH_2CH_3$ | $CH_2C\equiv CH$ | $OCH_3$ | O |
| 040 | $4-CH_3$-Ph | H | $CH_2C\equiv CH$ | $CH_3$ | $OCH_3$ | O |
| 041 | $4-CH_3$-Ph | H | $CH_2C\equiv CH$ | $CH_2CH_3$ | $OCH_3$ | O |
| 042 | $4-CH_3$-Ph | H | $CH_2C\equiv CH$ | $CH_2C\equiv CH$ | $OCH_3$ | O |
| 043 | $4-CH_3$-Ph | $CH_3$ | $CH_2C\equiv CH$ | $CH_2C\equiv CH$ | $OCH_3$ | O |
| 044 | $4-CH_3$-Ph | H | $CH_2C\equiv CH$ | $CH_2C\equiv CH$ | $CH_3$ | O |
| 045 | $4-CH_3$-Ph | H | $CH_2C\equiv CH$ | $CH_2C\equiv CH$ | $OCH_3$ | S |
| 046 | $4-CF_3$-Ph | H | H | $CH_2C\equiv CH$ | $OCH_3$ | O |
| 047 | $4-CF_3$-Ph | H | $CH_3$ | $CH_2C\equiv CH$ | $OCH_3$ | O |
| 048 | $4-CF_3$-Ph | H | $CH_2CH_3$ | $CH_2C\equiv CH$ | $OCH_3$ | O |
| 049 | $4-CF_3$-Ph | H | $CH_2C\equiv CH$ | $CH_3$ | $OCH_3$ | O |
| 050 | $4-CF_3$-Ph | H | $CH_2C\equiv CH$ | $CH_2CH_3$ | $OCH_3$ | O |
| 051 | $4-CF_3$-Ph | H | $CH_2C\equiv CH$ | $CH_2C\equiv CH$ | $OCH_3$ | O |
| 052 | $4-CF_3$-Ph | $CH_3$ | $CH_2C\equiv CH$ | $CH_2C\equiv CH$ | $OCH_3$ | O |
| 053 | $4-CF_3$-Ph | H | $CH_2C\equiv CH$ | $CH_2C\equiv CH$ | $CH_3$ | O |
| 054 | $4-CF_3$-Ph | H | $CH_2C\equiv CH$ | $CH_2C\equiv CH$ | $OCH_3$ | S |
| 055 | $4-CH_3CH_2$-Ph | H | H | $CH_2C\equiv CH$ | $OCH_3$ | O |
| 056 | $4-CH_3CH_2$-Ph | H | $CH_3$ | $CH_2C\equiv CH$ | $OCH_3$ | O |
| 057 | $4-CH_3CH_2$-Ph | H | $CH_2CH_3$ | $CH_2C\equiv CH$ | $OCH_3$ | O |
| 058 | $4-CH_3CH_2$-Ph | H | $CH_2C\equiv CH$ | $CH_3$ | $OCH_3$ | O |
| 059 | $4-CH_3CH_2$-Ph | H | $CH_2C\equiv CH$ | $CH_2CH_3$ | $OCH_3$ | O |
| 060 | $4-CH_3CH_2$-Ph | H | $CH_2C\equiv CH$ | $CH_2C\equiv CH$ | $OCH_3$ | O |
| 061 | $4-CH_3CH_2$-Ph | $CH_3$ | $CH_2C\equiv CH$ | $CH_2C\equiv CH$ | $OCH_3$ | O |
| 062 | $4-CH_3CH_2$-Ph | H | $CH_2C\equiv CH$ | $CH_2OEOH$ | $CH_3$ | O |
| 063 | $4-CH_3CH_2$-Ph | H | $CH_2C\equiv CH$ | $CH_2C\equiv CH$ | $OCH_3$ | S |
| 064 | $4-CH_3O$-Ph | H | H | $CH_2C\equiv CH$ | $OCH_3$ | O |
| 065 | $4-CH_3O$-Ph | H | $CH_3$ | $CH_2C\equiv CH$ | $OCH_3$ | O |
| 066 | $4-CH_3O$-Ph | H | $CH_2CH_3$ | $CH_2C\equiv CH$ | $OCH_3$ | O |
| 067 | $4-CH_3O$-Ph | H | $CH_2C\equiv CH$ | $CH_3$ | $OCH_3$ | O |
| 068 | $4-CH_3O$-Ph | H | $CH_2C\equiv CH$ | $CH_2CH_3$ | $OCH_3$ | O |
| 069 | $4-CH_3O$-Ph | H | $CH_2C\equiv CH$ | $CH_2C\equiv CH$ | $OCH_3$ | O |
| 070 | $4-CH_3O$-Ph | $CH_3$ | $CH_2C\equiv CH$ | $CH_2C\equiv CH$ | $OCH_3$ | O |
| 071 | $4-CH_3O$-Ph | H | $CH_2C\equiv CH$ | $CH_2C\equiv CH$ | $CH_3$ | O |
| 072 | $4-CH_3O$-Ph | H | $CH_2C\equiv CH$ | $CH_2C\equiv CH$ | $OCH_3$ | S |
| 073 | $3,4-Cl_2$-Ph | H | H | $CH_2C\equiv CH$ | $OCH_3$ | O |
| 074 | $3,4-Cl_2$-Ph | H | $CH_3$ | $CH_2C\equiv CH$ | $OCH_3$ | O |
| 075 | $3,4-Cl_2$-Ph | H | $CH_2CH_3$ | $CH_2C\equiv CH$ | $OCH_3$ | O |
| 076 | $3,4-Cl_2$-Ph | H | $CH_2C\equiv CH$ | $CH_3$ | $OCH_3$ | O |
| 077 | $3,4-Cl_2$-Ph | H | $CH_2C\equiv CH$ | $CH_2CH_3$ | $OCH_3$ | O |
| 078 | $3,4-Cl_2$-Ph | H | $CH_2C\equiv CH$ | $CH_2C\equiv CH$ | $OCH_3$ | O |
| 079 | $3,4-Cl_2$-Ph | $CH_3$ | $CH_2C\equiv CH$ | $CH_2C\equiv CH$ | $OCH_3$ | O |
| 080 | $3,4-Cl_2$-Ph | H | $CH_2C\equiv CH$ | $CH_2C\equiv CH$ | $CH_3$ | O |
| 081 | $3,4-Cl_2$-Ph | H | $CH_2C\equiv CH$ | $CH_2C\equiv CH$ | $OCH_3$ | S |

TABLE A-continued

| No. | A | R₁ | R₂ | R₃ | R₄ | X |
|---|---|---|---|---|---|---|
| 082 | 2-F-Ph | H | H | CH₂C≡CH | OCH₃ | O |
| 083 | 2-F-Ph | H | CH₃ | CH₂C≡CH | OCH₃ | O |
| 084 | 2-F-Ph | H | CH₂CH3 | CH₂C≡CH | OCH₃ | O |
| 085 | 2-F-Ph | H | CH₂C≡CH | CH₃ | OCH₃ | O |
| 086 | 2-F-Ph | H | CH₂C≡CH | CH₂CH₃ | OCH₃ | O |
| 087 | 2-F-Ph | H | CH₂C≡CH | CH₂C≡CH | 0CH₃ | O |
| 088 | 2-Cl-Ph | H | H | CH₂C≡CH | OCH₃ | O |
| 089 | 2-Cl-Ph | H | CH₃ | CH₂C≡CH | OCH₃ | O |
| 090 | 2-Cl-Ph | H | CH₂CH₃ | CH₂C≡CH | 0CH₃ | O |
| 091 | 2-Cl-Ph | H | CH₂C≡CH | CH₃ | OCH₃ | O |
| 092 | 2-Cl-Ph | H | CH₂C≡CH | CH₂CH₃ | OCH₃ | O |
| 093 | 2-Cl-Ph | H | CH₂C≡CH | CH₂C≡CH | OCH₃ | O |
| 094 | 2-CH₃-Ph | H | H | CH₂C≡CH | OCH₃ | O |
| 095 | 2-CH₃-Ph | H | CH₃ | CH₂C≡CH | OCH₃ | O |
| 096 | 2-CH₃-Ph | H | CH₂CH3 | CH₂C≡CH | OCH₃ | O |
| 097 | 2-CH₃-Ph | H | CH₂C≡CH | CH₃ | OCH₃ | O |
| 098 | 2-CH₃-Ph | H | CH₂OEOH | CH₂CH₃ | OCH₃ | O |
| 099 | 2-CH₃-Ph | H | CH₂C≡CH | CH₂C≡CH | OCH₃ | O |
| 100 | 2-CF₃-Ph | H | H | CH₂C≡CH | OCH₃ | O |
| 101 | 2-CF₃-Ph | H | CH₃ | CH₂C≡CH | OCH₃ | O |
| 102 | 2-CF₃-Ph | H | CH₂CH₃ | CH₂C≡CH | OCH₃ | O |
| 103 | 2-CF₃-Ph | H | CH₂C≡CH | CH₃ | OCH₃ | O |
| 104 | 2-CF₃-Ph | H | CH₂C≡CH | CH₂CH₃ | OCH₃ | O |
| 105 | 2-CF₃-Ph | H | CH₂C≡CH | CH₂C≡CH | OCH₃ | O |
| 106 | 2-CN-Ph | H | H | CH₂C≡CH | OCH₃ | O |
| 107 | 2-CN-Ph | H | CH₃ | CH₂C≡CH | OCH₃ | O |
| 108 | 2-CN-Ph | H | CH₂CH₃ | CH₂C≡CH | OCH₃ | O |
| 109 | 2-CN-Ph | H | CH₂C≡CH | CH₃ | OCH₃ | O |
| 110 | 2-CN-Ph | H | CH₂C≡CH | CH₂CH₃ | OCH₃ | O |
| 111 | 2-CN-Ph | H | CH₂C≡CH | CH₂C≡CH | OCH₃ | O |
| 112 | 2-CH₃O-Ph | H | H | CH₂C≡CH | OCH₃ | O |
| 113 | 2-CH₃O-Ph | H | CH₃ | CH₂C≡CH | OCH₃ | O |
| 114 | 2-CH₃O-Ph | H | CH₂CH₃ | CH₂C≡CH | OCH₃ | O |
| 115 | 2-CH₃O-Ph | H | CH₂C≡CH | CH₃ | OCH₃ | O |
| 116 | 2-CH₃O-Ph | H | CH₂C≡CH | CH₂CH₃ | OCH₃ | O |
| 117 | 2-CH₃O-Ph | H | CH₂C≡CH | CH₂C≡CH | OCH₃ | O |
| 118 | 3-F-Ph | H | H | CH₂C≡CH | OCH₃ | O |
| 119 | 3-F-Ph | H | CH₃ | CH₂C≡CH | OCH₃ | O |
| 120 | 3-F-Ph | H | CH₂CH₃ | CH₂C≡CH | OCH₃ | O |
| 121 | 3-F-Ph | H | CH₂C≡CH | CH₃ | OCH₃ | O |
| 122 | 3-F-Ph | H | CH₂C≡CH | CH₂CH₃ | OCH₃ | O |
| 123 | 3-F-Ph | H | CH₂C≡CH | CH₂C≡CH | OCH3 | O |
| 124 | 3-Cl-Ph | H | H | CH₂C≡CH | OCH₃ | O |
| 125 | 3-Cl-Ph | H | CH₃ | CH₂C≡CH | OCH₃ | O |
| 126 | 3-Cl-Ph | H | CH₂CH3 | CH₂C≡CH | OCH₃ | O |
| 127 | 3-Cl-Ph | H | CH₂C≡CH | CH₃ | OCH₃ | O |
| 128 | 3-Cl-Ph | H | CH₂C≡CH | CH₂CH₃ | OCH₃ | O |
| 129 | 3-Cl-Ph | H | CH₂C≡CH | CH₂C≡CH | OCH₃ | O |
| 130 | 3-Br-Ph | H | H | CH₂C≡CH | OCH₃ | O |
| 131 | 3-Br-Ph | H | CH₃ | CH₂C≡CH | OCH₃ | O |
| 132 | 3-Br-Ph | H | CH₂CH₃ | CH₂C≡CH | OCH₃ | O |
| 133 | 3-Br-Ph | H | CH₂C≡CH | CH₃ | OCH₃ | O |
| 134 | 3-Br-Ph | H | CH₂C≡CH | CH₂CH₃ | OCH₃ | O |
| 135 | 3-Br-Ph | H | CH₂C≡CH | CH₂C≡CH | OCH₃ | O |
| 136 | 3-CH₃-Ph | H | H | CH₂C≡CH | OCH₃ | O |
| 137 | 3-CH₃-Ph | H | CH₃ | CH₂C≡CH | OCH₃ | O |
| 138 | 3-CH₃-Ph | H | CH₂CH₃ | CH₂C≡CH | OCH₃ | O |
| 139 | 3-CH₃-Ph | H | CH₂C≡CH | CH₃ | OCH₃ | O |
| 140 | 3-CH₃-Ph | H | CH₂C≡CH | CH₂CH₃ | OCH₃ | O |
| 141 | 3-CH₃-Ph | H | CH₂C≡CH | CH₂C≡CH | OCH₃ | O |
| 142 | 3-CF₃-Ph | H | H | CH₂C≡CH | OCH₃ | O |
| 143 | 3-CF₃-Ph | H | CH₃ | CH₂C≡CH | OCH₃ | O |
| 144 | 3-CF₃-Ph | H | CH₂CH₃ | CH₂C≡CH | OCH₃ | O |
| 145 | 3-CF₃-Ph | H | CH₂C≡CH | CH₃ | OCH₃ | O |
| 146 | 3-CF₃-Ph | H | CH₂C≡CH | CH₂CH₃ | OCH₃ | O |
| 147 | 3-CF₃-Ph | H | CH₂C≡CH | CH₂C≡CH | OCH₃ | O |
| 148 | 3-CN-Ph | H | H | CH₂C≡CH | OCH₃ | O |
| 149 | 3-CN-Ph | H | CH₃ | CH₂C≡CH | OCH₃ | O |
| 150 | 3-CN-Ph | H | CH₂CH₃ | CH₂C≡CH | OCH₃ | O |
| 151 | 3-CN-Ph | H | CH₂C≡CH | CH₃ | OCH₃ | O |
| 152 | 3-CN-Ph | H | CH₂C≡CH | CH₂CH₃ | OCH₃ | O |
| 153 | 3-CN-Ph | H | CH₂C≡CH | CH₂C≡CH | OCH₃ | O |
| 154 | 3-CH₃O-Ph | H | H | CH₂C≡CH | OCH₃ | O |
| 155 | 3-CH₃O-Ph | H | CH₃ | CH₂C≡CH | OCH₃ | O |
| 156 | 3-CH₃O-Ph | H | CH₂CH₃ | CH₂C≡CH | OCH₃ | O |
| 157 | 3-CH₃O-Ph | H | CH₂C≡CH | CH₃ | OCH₃ | O |
| 158 | 3-CH₃O-Ph | H | CH₂C≡CH | CH₂CH₃ | OCH₃ | O |

TABLE A-continued

| No. | A | R₁ | R₂ | R₃ | R₄ | X |
|---|---|---|---|---|---|---|
| 159 | 3-CH₃O-Ph | H | CH₂C≡CH | CH₂C≡CH | OCH₃ | O |
| 160 | 3-CF₃O-Ph | H | H | CH₂C≡CH | OCH₃ | O |
| 161 | 3-CF₃O-Ph | H | CH₃ | CH₂C≡CH | OCH₃ | O |
| 162 | 3-CF₃O-Ph | H | CH₂CH₃ | CH₂C≡CH | OCH₃ | O |
| 163 | 3-CF₃O-Ph | H | CH₂C≡CH | CH₃ | OCH₃ | O |
| 164 | 3-CF₃O-Ph | H | CH₂C≡CH | CH₂CH₃ | OCH₃ | O |
| 165 | 3-CF₃O-Ph | H | CH₂C≡CH | CH₂C≡CH | OCH₃ | O |
| 166 | 4-CH₂═CH-Ph | H | H | CH₂C≡CH | OCH₃ | O |
| 167 | 4-CH₂═CH-Ph | H | CH₃ | CH₂C≡CH | OCH₃ | O |
| 168 | 4-CH₂═CH-Ph | H | CH₂CH₃ | CH₂C≡CH | OCH₃ | O |
| 169 | 4-CH₂═CH-Ph | H | CH₂C≡CH | CH₃ | OCH₃ | O |
| 170 | 4-CH₂═CH-Ph | H | CH₂C≡CH | CH₂CH₃ | OCH₃ | O |
| 171 | 4-CH₂═CH-Ph | H | CH₂C≡CH | CH₂C≡CH | OCH₃ | O |
| 172 | 4-CH≡C-Ph | H | H | CH₂C≡CH | OCH₃ | O |
| 173 | 4-CH≡C-Ph | H | CH₃ | CH₂C≡CH | OCH₃ | O |
| 174 | 4-CH≡C-Ph | H | CH₂CH₃ | CH₂C≡CH | OCH₃ | O |
| 175 | 4-CH≡C-Ph | H | CH₂C≡CH | CH₃ | OCH₃ | O |
| 176 | 4-CH≡C-Ph | H | CH₂C≡CH | CH₂CH₃ | OCH₃ | O |
| 177 | 4-CH≡C-Ph | H | CH₂C≡CH | CH₂C≡CH | OCH₃ | O |
| 178 | 4-CH₃CH₂CH₂-Ph | H | H | CH₂C≡CH | OCH₃ | O |
| 179 | 4-CH₃CH₂CH₂-Ph | H | CH₃ | CH₂C≡CH | OCH₃ | O |
| 180 | 4-CH₃CH₂CH₂-Ph | H | CH₂CH₃ | CH₂C≡CH | OCH₃ | O |
| 181 | 4-CH₃CH₂CH₂-Ph | H | CH₂C≡CH | CH₃ | OCH₃ | O |
| 182 | 4-CH₃CH₂CH₂-Ph | H | CH₂C≡CH | CH₂OHS | OCH₃ | O |
| 183 | 4-CH₃CH₂CH₂-Ph | H | CH₂C≡CH | CH₂C≡CH | OCH₃ | O |
| 184 | 4-(CH₃)₂CH-Ph | H | H | CH₂C≡CH | OCH₃ | O |
| 185 | 4-(CH₃)₂CH-Ph | H | CH₃ | CH₂C≡CH | OCH₃ | O |
| 186 | 4-(CH₃)₂CH-Ph | H | CH₂CH₃ | CH₂C≡CH | OCH₃ | O |
| 187 | 4-(CH₃)₂CH-Ph | H | CH₂C≡CH | CH₃ | OCH₃ | O |
| 188 | 4-(CH₃)₂CH-Ph | H | CH₂C≡CH | CH₂CH₃ | OCH₃ | O |
| 189 | 4-(CH₃)₂CH-Ph | H | CH₂C≡CH | CH₂C≡CH | OCH₃ | O |
| 190 | 4-(CH₃)₃C-Ph | H | H | CH₂C≡CH | OCH₃ | O |
| 191 | 4-(CH₃)₃C-Ph | H | CH₃ | CH₂C≡CH | OCH₃ | O |
| 192 | 4-(CH₃)₃C-Ph | H | CH₂CH₃ | CH₂C≡CH | OCH₃ | O |
| 193 | 4-(CH₃)₃C-Ph | H | CH₂C≡CH | CH₃ | OCH₃ | O |
| 194 | 4-(CH₃)₃C-Ph | H | CH₂C≡CH | CH₂CH₃ | OCH₃ | O |
| 195 | 4-(CH₃)₃C-Ph | H | CH₂C≡CH | CH₂C≡CH | OCH₃ | O |
| 196 | 4-CN-Ph | H | H | CH₂C≡CH | OCH₃ | O |
| 197 | 4-CN-Ph | H | CH₃ | CH₂C≡CH | OCH₃ | O |
| 198 | 4-CN-Ph | H | CH₂CH₃ | CH₂C≡CH | OCH₃ | O |
| 199 | 4-CN-Ph | H | CH₂C≡CH | CH₃ | OCH₃ | O |
| 200 | 4-CN-Ph | H | CH₂C≡CH | CH₂CH₃ | OCH₃ | O |
| 201 | 4-CN-Ph | H | CH₂C≡CH | CH₂C≡CH | OCH₃ | O |
| 202 | 4-CF₃O-Ph | H | H | CH₂C≡CH | OCH₃ | O |
| 203 | 4-CF₃O-Ph | H | CH₃ | CH₂C≡CH | OCH₃ | O |
| 204 | 4-CF₃O-Ph | H | CH₂CH₃ | CH₂C≡CH | OCH₃ | O |
| 205 | 4-CF₃O-Ph | H | CH₂C≡CH | CH₃ | OCH₃ | O |
| 206 | 4-CF₃O-Ph | H | CH₂C≡CH | CH₂CH₃ | OCH₃ | O |
| 207 | 4-CF₃O-Ph | H | CH₂C≡CH | CH₂C≡CH | OCH₃ | O |
| 208 | 4-CH₃S-Ph | H | H | CH₂C≡CH | OCH₃ | O |
| 209 | 4-CH₃S-Ph | H | CH₃ | CH₂C≡CH | OCH₃ | O |
| 210 | 4-CH₃S-Ph | H | CH₂CH₃ | CH₂C≡CH | OCH₃ | O |
| 211 | 4-CH₃S-Ph | H | CH₂C≡CH | CH₃ | OCH₃ | O |
| 212 | 4-CH₃S-Ph | H | CH₂C≡CH | CH₂CH₃ | OCH₃ | O |
| 213 | 4-CH₃S-Ph | H | CH₂C≡CH | CH₂C≡CH | OCH₃ | O |
| 214 | 4-CF₃S-Ph | H | H | CH₂C≡CH | OCH₃ | O |
| 215 | 4-CF₃S-Ph | H | CH₃ | CH₂C≡CH | OCH₃ | O |
| 216 | 4-CF₃S-Ph | H | CH₂CH₃ | CH₂C≡CH | OCH₃ | O |
| 217 | 4-CF₃S-Ph | H | CH₂C≡CH | CH₃ | OCH₃ | O |
| 218 | 4-CF₃S-Ph | H | CH₂C≡CH | CH₂CH₃ | OCH₃ | O |
| 219 | 4-CF₃S-Ph | H | CH₂C≡CH | CH₂C≡CH | OCH₃ | O |
| 220 | 4-CH₃CH₂O-Ph | H | H | CH₂C≡CH | OCH₃ | O |
| 221 | 4-CH₃CH₂O-Ph | H | CH₃ | CH₂C≡CH | OCH₃ | O |
| 222 | 4-CH₃CH₂O-Ph | H | CH₂CH₃ | CH₂C≡CH | OCH₃ | O |
| 223 | 4-CH₃CH₂O-Ph | H | CH₂C≡CH | CH₃ | OCH₃ | O |
| 224 | 4-CH₃CH₂O-Ph | H | CH₂C≡CH | CH₂CH₃ | OCH₃ | O |
| 225 | 4-CH₃CH₂O-Ph | H | CH₂C≡CH | CH₂C≡CH | OCH₃ | O |
| 226 | 4-CH₃CH₂CH₂O-Ph | H | H | CH₂C≡CH | OCH₃ | O |
| 227 | 4-CH₃CH₂CH₂O-Ph | H | CH₃ | CH₂C≡CH | OCH₃ | O |
| 228 | 4-CH₃CH₂CH₂O-Ph | H | CH₂CH₃ | CH₂C≡CH | OCH₃ | O |
| 229 | 4-CH₃CH₂CH₂O-Ph | H | CH₂C≡CH | CH₃ | OCH₃ | O |
| 230 | 4-CH₃CH₂CH₂O-Ph | H | CH₂C≡CH | CH₂CH₃ | OCH₃ | O |
| 231 | 4-CH₃CH₂CH₂O-Ph | H | CH₂C≡CH | CH₂C≡CH | OCH₃ | O |
| 232 | 3,4-Br₂-Ph | H | H | CH₂C≡CH | OCH₃ | O |
| 233 | 3,4-Br₂-Ph | H | CH₃ | CH₂C≡CH | OCH₃ | O |
| 234 | 3,4-Br₂-Ph | H | CH₂CH₃ | CH₂C≡CH | OCH₃ | O |
| 235 | 3,4-Br₂-Ph | H | CH₂C≡CH | CH₃ | OCH₃ | O |

TABLE A-continued

| No. | A | $R_1$ | $R_2$ | $R_3$ | $R_4$ | X |
|---|---|---|---|---|---|---|
| 236 | 3,4-Br$_2$-Ph | H | CH$_2$C≡CH | CH$_2$CH$_3$ | OCH$_3$ | O |
| 237 | 3,4-Br$_2$-Ph | H | CH$_2$C≡CH | CH$_2$C≡CH | OCH$_3$ | O |
| 238 | 3,5-Br$_2$-Ph | H | H | CH$_2$C≡CH | OCH$_3$ | O |
| 239 | 3,5-Br$_2$-Ph | H | CH$_3$ | CH$_2$C≡CH | OCH$_3$ | O |
| 240 | 3,5-Br$_2$-Ph | H | CH$_2$CH$_3$ | CH$_2$C≡CH | OCH$_3$ | O |
| 241 | 3,5-Br$_2$-Ph | H | CH$_2$C≡CH | CH$_3$ | OCH$_3$ | O |
| 242 | 3,5-Br$_2$-Ph | H | CH$_2$C≡CH | CH$_2$CH$_3$ | OCH$_3$ | O |
| 243 | 3,5-Br$_2$-Ph | H | CH$_2$C≡CH | CH$_2$C≡CH | OCH$_3$ | O |
| 244 | 2,3-Cl$_2$-Ph | H | H | CH$_2$C≡CH | OCH$_3$ | O |
| 245 | 2,3-Cl$_2$-Ph | H | CH$_3$ | CH$_2$C≡CH | OCH$_3$ | O |
| 246 | 2,3-Cl$_2$-Ph | H | CH$_2$CH$_3$ | CH$_2$C≡CH | OCH$_3$ | O |
| 247 | 2,3-Cl$_2$-Ph | H | CH$_2$C≡CH | CH$_3$ | OCH$_3$ | O |
| 248 | 2,3-Cl$_2$-Ph | H | CH$_2$C≡CH | CH$_2$CH$_3$ | OCH$_3$ | O |
| 249 | 2,3-Cl$_2$-Ph | H | CH$_2$C≡CH | CH$_2$C≡CH | OCH$_3$ | O |
| 250 | 2,4-Cl$_2$-Ph | H | H | CH$_2$C≡CH | OCH$_3$ | O |
| 251 | 2,4-Cl$_2$-Ph | H | CH$_3$ | CH$_2$C≡CH | OCH$_3$ | O |
| 252 | 2,4-Cl$_2$-Ph | H | CH$_2$CH$_3$ | CH$_2$C≡CH | OCH$_3$ | O |
| 253 | 2,4-Cl$_2$-Ph | H | CH$_2$C≡CH | CH$_3$ | OCH$_3$ | O |
| 254 | 2,4-Cl$_2$-Ph | H | CH$_2$C≡CH | CH$_2$CH$_3$ | OCH$_3$ | O |
| 255 | 2,4-Cl$_2$-Ph | H | CH$_2$C≡CH | CH$_2$C≡CH | OCH$_3$ | O |
| 256 | 3,5-Cl$_2$-Ph | H | H | CH$_2$C≡CH | OCH$_3$ | O |
| 257 | 3,5-Cl$_2$-Ph | H | CH$_3$ | CH$_2$C≡CH | OCH$_3$ | O |
| 258 | 3,5-Cl$_2$-Ph | H | CH$_2$CH$_3$ | CH$_2$C≡CH | OCH$_3$ | O |
| 259 | 3,5-Cl$_2$-Ph | H | CH$_2$C≡CH | CH$_3$ | OCH$_3$ | O |
| 260 | 3,5-Cl$_2$-Ph | H | CH$_2$C≡CH | CH$_2$CH$_3$ | OCH$_3$ | O |
| 261 | 3,5-Cl$_2$-Ph | H | CH$_2$C≡CH | CH$_2$C≡CH | OCH$_3$ | O |
| 262 | 2,4-F$_2$-Ph | H | H | CH$_2$C≡CH | OCH$_3$ | O |
| 263 | 2,4-F$_2$-Ph | H | CH$_3$ | CH$_2$C≡CH | OCH$_3$ | O |
| 264 | 2,4-F$_2$-Ph | H | CH$_2$CH$_3$ | CH$_2$C≡CH | OCH$_3$ | O |
| 265 | 2,4-F$_2$-Ph | H | CH$_2$C≡CH | CH$_3$ | OCH$_3$ | O |
| 266 | 2,4-F$_2$-Ph | H | CH$_2$C≡CH | CH$_2$CH$_3$ | OCH$_3$ | O |
| 267 | 2,4-F$_2$-Ph | H | CH$_2$C≡CH | CH$_2$C≡CH | OCH$_3$ | O |
| 268 | 3,4-F$_2$-Ph | H | H | CH$_2$C≡CH | OCH$_3$ | O |
| 269 | 3,4-F$_2$-Ph | H | CH$_3$ | CH$_2$C≡CH | OCH$_3$ | O |
| 270 | 3,4-F$_2$-Ph | H | CH$_2$CH$_3$ | CH$_2$C≡CH | OCH$_3$ | O |
| 271 | 3,4-F$_2$-Ph | H | CH$_2$C≡CH | CH$_3$ | OCH$_3$ | O |
| 273 | 3,4-F$_2$-Ph | H | CH$_2$C≡CH | CH$_2$CH$_3$ | OCH$_3$ | O |
| 274 | 3,4-F$_2$-Ph | H | CH$_2$C≡CH | CH$_2$C≡CH | OCH$_3$ | O |
| 275 | 3,5-F$_2$-Ph | H | H | CH$_2$C≡CH | OCH$_3$ | O |
| 276 | 3,5-F$_2$-Ph | H | CH$_3$ | CH$_2$C≡CH | OCH$_3$ | O |
| 277 | 3,5-F$_2$-Ph | H | CH$_2$CH$_3$ | CH$_2$C≡CH | OCH$_3$ | O |
| 278 | 3,5-F$_2$-Ph | H | CH$_2$C≡CH | CH$_3$ | OCH$_3$ | O |
| 279 | 3,5-F$_2$-Ph | H | CH$_2$C≡CH | CH$_2$CH$_3$ | OCH$_3$ | O |
| 280 | 3,5-F$_2$-Ph | H | CH$_2$C≡CH | CH$_2$C≡CH | OCH$_3$ | O |
| 281 | 3-Br-4-F-Ph | H | H | CH$_2$C≡CH | OCH$_3$ | O |
| 282 | 3-Br-4-F-Ph | H | CH$_3$ | CH$_2$C≡CH | OCH$_3$ | O |
| 283 | 3-Br-4-F-Ph | H | CH$_2$CH$_3$ | CH$_2$C≡CH | OCH$_3$ | O |
| 284 | 3-Br-4-F-Ph | H | CH$_2$C≡CH | CH$_3$ | OCH$_3$ | O |
| 285 | 3-Br-4-F-Ph | H | CH$_2$C≡CH | CH$_2$CH$_3$ | OCH$_3$ | O |
| 286 | 3-Br-4-F-Ph | H | CH$_2$C≡CH | CH$_2$C≡CH | OCH$_3$ | O |
| 287 | 3-Cl-4-F-Ph | H | H | CH$_2$C≡CH | OCH$_3$ | O |
| 288 | 3-Cl-4-F-Ph | H | CH$_3$ | CH$_2$C≡CH | OCH$_3$ | O |
| 289 | 3-Cl-4-F-Ph | H | CH$_2$CH$_3$ | CH$_2$C≡CH | OCH$_3$ | O |
| 290 | 3-Cl-4-F-Ph | H | CH$_2$C≡CH | CH$_3$ | OCH$_3$ | O |
| 291 | 3-Cl-4-F-Ph | H | CH$_2$C≡CH | CH$_2$CH$_3$ | OCH$_3$ | O |
| 292 | 3-Cl-4-F-Ph | H | CH$_2$C≡CH | CH$_2$C≡CH | OCH$_3$ | O |
| 293 | 3-F-4-Cl-Ph | H | H | CH$_2$C≡CH | OCH$_3$ | O |
| 294 | 3-F-4-Cl-Ph | H | CH$_3$ | CH$_2$C≡CH | OCH$_3$ | O |
| 295 | 3-F-4-Cl-Ph | H | CH$_2$CH$_3$ | CH$_2$C≡CH | OCH$_3$ | O |
| 296 | 3-F-4-Cl-Ph | H | CH$_2$C≡CH | CH$_3$ | OCH$_3$ | O |
| 297 | 3-F-4-Cl-Ph | H | CH$_2$C≡CH | CH$_2$CH$_3$ | OCH$_3$ | O |
| 298 | 3-F-4-Cl-Ph | H | CH$_2$C≡CH | CH$_2$C≡CH | OCH$_3$ | O |
| 299 | 3-CF$_3$-4-Cl-Ph | H | H | CH$_2$C≡CH | OCH$_3$ | O |
| 300 | 3-CF$_3$-4-Cl-Ph | H | CH$_3$ | CH$_2$C≡CH | OCH$_3$ | O |
| 301 | 3-CF$_3$-4-Cl-Ph | H | CH$_2$CH$_3$ | CH$_2$C≡CH | OCH$_3$ | O |
| 302 | 3-CF$_3$-4-Cl-Ph | H | CH$_2$C≡CH | CH$_3$ | OCH$_3$ | O |
| 303 | 3-CF$_3$-4-Cl-Ph | H | CH$_2$C≡CH | CH$_2$CH$_3$ | OCH$_3$ | O |
| 304 | 3-CF$_3$-4-Cl-Ph | H | CH$_2$C≡CH | CH$_2$C≡CH | OCH$_3$ | O |
| 305 | 3,4-(CH$_3$)$_2$-Ph | H | H | CH$_2$C≡CH | OCH$_3$ | O |
| 306 | 3,4-(CH$_3$)$_2$-Ph | H | CH$_3$ | CH$_2$C≡CH | OCH$_3$ | O |
| 307 | 3,4-(CH$_3$)$_2$-Ph | H | CH$_2$CH$_3$ | CH$_2$C≡CH | OCH$_3$ | O |
| 308 | 3,4-(CH$_3$)$_2$-Ph | H | CH$_2$C≡CH | CH$_3$ | OCH$_3$ | O |
| 309 | 3,4-(CH$_3$)$_2$-Ph | H | CH$_2$C≡CH | CH$_2$CH$_3$ | OCH$_3$ | O |
| 310 | 3,4-(CH$_3$)$_2$-Ph | H | CH$_2$C≡CH | CH$_2$C≡CH | OCH$_3$ | O |
| 311 | 3,5-(CH$_3$)$_2$-Ph | H | H | CH$_2$C≡CH | OCH$_3$ | O |
| 312 | 3,5-(CH$_3$)$_2$-Ph | H | CH$_3$ | CH$_2$C≡CH | OCH$_3$ | O |
| 313 | 3,5-(CH$_3$)$_2$-Ph | H | CH$_2$CH$_3$ | CH$_2$C≡CH | OCH$_3$ | O |

TABLE A-continued

| No. | A | R₁ | R₂ | R₃ | R₄ | X |
|---|---|---|---|---|---|---|
| 314 | 3,5-(CH₃)₂-Ph | H | CH₂C≡CH | CH₃ | OCH₃ | O |
| 315 | 3,5-(CH₃)₂-Ph | H | CH₂C≡CH | CH₂CH₃ | OCH₃ | O |
| 316 | 3,5-(CH₃)₂-Ph | H | CH₂C≡CH | CH₂C≡CH | OCH₃ | O |
| 317 | 3,4-(CH₃O)₂-Ph | H | H | CH₂C≡CH | OCH₃ | O |
| 318 | 3,4-(CH₃O)₂-Ph | H | CH₃ | CH₂C≡CH | OCH₃ | O |
| 319 | 3,4-(CH₃O)₂-Ph | H | CH₂CH₃ | CH₂C≡CH | OCH₃ | O |
| 320 | 3,4-(CH₃O)₂-Ph | H | CH₂C≡CH | CH₃ | OCH₃ | O |
| 321 | 3,4-(CH₃O)₂-Ph | H | CH₂C≡CH | CH₂CH₃ | OCH₃ | O |
| 322 | 3,4-(CH₃O)₂-Ph | H | CH₂C≡CH | CH₂C≡CH | OCH₃ | O |
| 323 | 3,5-(CH₃O)₂-Ph | H | H | CH₂C≡CH | OCH₃ | O |
| 324 | 3,5-(CH₃O)₂-Ph | H | CH₃ | CH₂C≡CH | OCH₃ | O |
| 325 | 3,5-(CH₃O)₂-Ph | H | CH₂CH₃ | CH₂C≡CH | OCH₃ | O |
| 326 | 3,5-(CH₃O)₂-Ph | H | CH₂C≡CH | CH₃ | OCH₃ | O |
| 327 | 3,5-(CH₃O)₂-Ph | H | CH₂C≡CH | CH₂CH₃ | OCH₃ | O |
| 328 | 3,5-(CH₃O)₂-Ph | H | CH₂C≡CH | CH₂C≡CH | OCH₃ | O |
| 329 | 3-CH₃-4-CH₃O-Ph | H | H | CH₂C≡CH | OCH₃ | O |
| 330 | 3-CH₃-4-CH₃O-Ph | H | CH₃ | CH₂C≡CH | OCH₃ | O |
| 331 | 3-CH₃-4-CH₃O-Ph | H | CH₂CH₃ | CH₂C≡CH | OCH₃ | O |
| 332 | 3-CH₃-4-CH₃O-Ph | H | CH₂C≡CH | CH₃ | OCH₃ | O |
| 333 | 3-CH₃-4-CH₃O-Ph | H | CH₂C≡CH | CH₂CH₃ | OCH₃ | O |
| 334 | 3-CH₃-4-CH₃O-Ph | H | CH₂C≡CH | CH₂C≡CH | OCH₃ | O |
| 335 | 3-F-4-CH₃O-Ph | H | H | CH₂C≡CH | OCH₃ | O |
| 336 | 3-F-4-CH₃O-Ph | H | CH₃ | CH₂C≡CH | OCH₃ | O |
| 337 | 3-F-4-CH₃O-Ph | H | CH₂CH₃ | CH₂C≡CH | OCH₃ | O |
| 338 | 3-F-4-CH₃O-Ph | H | CH₂C≡CH | CH₃ | OCH₃ | O |
| 339 | 3-F-4-CH₃O-Ph | H | CH₂C≡CH | CH₂CH₃ | OCH₃ | O |
| 340 | 3-F-4-CH₃O-Ph | H | CH₂C≡CH | CH₂C≡CH | OCH₃ | O |
| 341 | 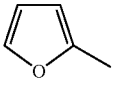 | H | H | CH₂C≡CH | OCH₃ | O |
| 342 | 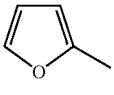 | H | CH₃ | CH₂C≡CH | OCH₃ | O |
| 343 | 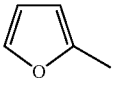 | H | CH₂CH₃ | CH₂C≡CH | OCH₃ | O |
| 344 | 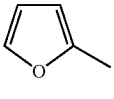 | H | CH₂C≡CH | CH₃ | OCH₃ | O |
| 345 | 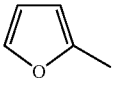 | H | CH₂C≡CH | CH₂CH₃ | OCH₃ | O |
| 346 | 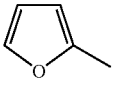 | H | CH₂C≡CH | CH₂C≡CH | OCH₃ | O |
| 347 | 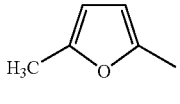 | H | H | CH₂C≡CH | OCH₃ | O |
| 348 | 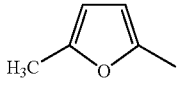 | H | CH₃ | CH₂C≡CH | OCH₃ | O |
| 349 | 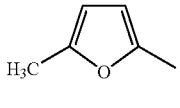 | H | CH₂CH₃ | CH₂C≡CH | OCH₃ | O |
| 350 | 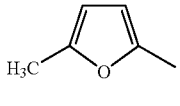 | H | CH₂C≡CH | CH₃ | OCH₃ | O |

TABLE A-continued

| No. | A | $R_1$ | $R_2$ | $R_3$ | $R_4$ | X |
|---|---|---|---|---|---|---|
| 351 | 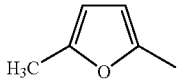 | H | $CH_2C\equiv CH$ | $CH_2CH_3$ | $OCH_3$ | O |
| 352 | 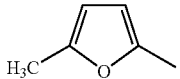 | H | $CH_2C\equiv CH$ | $CH_2C\equiv CH$ | $OCH_3$ | O |
| 353 | 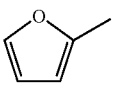 | H | H | $CH_2C\equiv CH$ | $OCH_3$ | O |
| 354 | 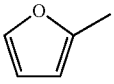 | H | $CH_3$ | $CH_2C\equiv CH$ | $OCH_3$ | O |
| 355 | 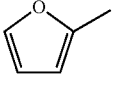 | H | $CH_2CH_3$ | $CH_2C\equiv CH$ | $OCH_3$ | O |
| 356 | 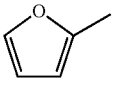 | H | $CH_2C\equiv CH$ | $CH_3$ | $OCH_3$ | O |
| 357 | 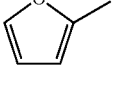 | H | $CH_2C\equiv CH$ | $CH_2CH_3$ | $OCH_3$ | O |
| 358 | 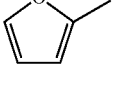 | H | $CH_2C\equiv CH$ | $CH_2C\equiv CH$ | $OCH_3$ | O |
| 359 | 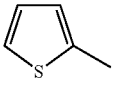 | H | H | $CH_2C\equiv CH$ | $OCH_3$ | O |
| 360 | 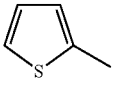 | H | $CH_3$ | $CH_2C\equiv CH$ | $OCH_3$ | O |
| 361 | 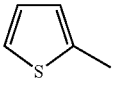 | H | $CH_2CH_3$ | $CH_2C\equiv CH$ | $OCH_3$ | O |
| 362 | 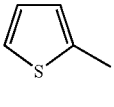 | H | $CH_2C\equiv CH$ | $CH_3$ | $OCH_3$ | O |
| 363 | 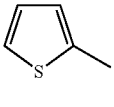 | H | $CH_2C\equiv CH$ | $CH_2CH_3$ | $OCH_3$ | O |
| 364 | 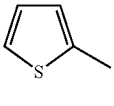 | H | $CH_2C\equiv CH$ | $CH_2C\equiv CH$ | $OCH_3$ | O |
| 365 | 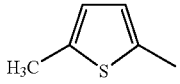 | H | H | $CH_2C\equiv CH$ | $OCH_3$ | O |
| 366 | 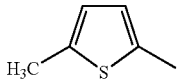 | H | $CH_3$ | $CH_2C\equiv CH$ | $OCH_3$ | O |

TABLE A-continued

| No. | A | R$_1$ | R$_2$ | R$_3$ | R$_4$ | X |
|---|---|---|---|---|---|---|
| 367 | 2,5-dimethylthiophene | H | CH$_2$CH$_3$ | CH$_2$C≡CH | OCH$_3$ | O |
| 368 | 2,5-dimethylthiophene | H | CH$_2$C≡CH | CH$_3$ | OCH$_3$ | O |
| 369 | 2,5-dimethylthiophene | H | CH$_2$C≡CH | CH$_2$CH$_3$ | OCH$_3$ | O |
| 370 | 2,5-dimethylthiophene | H | CH$_2$C≡CH | CH$_2$C≡CH | OCH$_3$ | O |
| 371 | 2-thienyl | H | H | CH$_2$C≡CH | OCH$_3$ | O |
| 372 | 2-thienyl | H | CH$_3$ | CH$_2$C≡CH | OCH$_3$ | O |
| 373 | 2-thienyl | H | CH$_2$CH$_3$ | CH$_2$C≡CH | OCH$_3$ | O |
| 374 | 2-thienyl | H | CH$_2$C≡CH | CH$_3$ | OCH$_3$ | O |
| 375 | 2-thienyl | H | CH$_2$C≡CH | CH$_2$CH$_3$ | OCH$_3$ | O |
| 376 | 2-thienyl | H | CH$_2$C≡CH | CH$_2$C≡CH | OCH$_3$ | O |
| 377 | 5-methylisoxazol-3-yl | H | H | CH$_2$C≡CH | OCH$_3$ | O |
| 378 | 5-methylisoxazol-3-yl | H | CH$_3$ | CH$_2$C≡CH | OCH$_3$ | O |
| 379 | 5-methylisoxazol-3-yl | H | CH$_2$CH$_3$ | CH$_2$C≡CH | OCH$_3$ | O |
| 380 | 5-methylisoxazol-3-yl | H | CH$_2$C≡CH | CH$_3$ | OCH$_3$ | O |
| 381 | 5-methylisoxazol-3-yl | H | CH$_2$C≡CH | CH$_2$CH$_3$ | OCH$_3$ | O |
| 382 | 5-methylisoxazol-3-yl | H | CH$_2$C≡CH | CH$_2$C≡CH | OCH$_3$ | O |

TABLE A-continued

| No. | A | R₁ | R₂ | R₃ | R₄ | X |
|---|---|---|---|---|---|---|
| 383 | 5-methylthiazolyl | H | H | CH₂C≡CH | OCH₃ | O |
| 384 | 5-methylthiazolyl | H | CH₃ | CH₂C≡CH | OCH₃ | O |
| 385 | 5-methylthiazolyl | H | CH₂CH₃ | CH₂C≡CH | OCH₃ | O |
| 386 | 5-methylthiazolyl | H | CH₂C≡CH | CH₃ | OCH₃ | O |
| 387 | 5-methylthiazolyl | H | CH₂C≡CH | CH₂CH₃ | OCH₃ | O |
| 388 | 5-methylthiazolyl | H | CH₂C≡CH | CH₂C≡CH | OCH₃ | O |
| 389 | 2-pyridyl | H | H | CH₂C≡CH | OCH₃ | O |
| 390 | 2-pyridyl | H | CH₃ | CH₂C≡CH | OCH₃ | O |
| 391 | 2-pyridyl | H | CH₂CH₃ | CH₂C≡CH | OCH₃ | O |
| 392 | 2-pyridyl | H | CH₂C≡CH | CH₃ | OCH₃ | O |
| 393 | 2-pyridyl | H | CH₂C≡CH | CH₂CH₃ | OCH₃ | O |
| 394 | 2-pyridyl | H | CH₂C≡CH | CH₂C≡CH | OCH₃ | O |
| 395 | 3-pyridyl | H | H | CH₂C≡CH | OCH₃ | O |
| 396 | 3-pyridyl | H | CH₃ | CH₂C≡CH | OCH₃ | O |
| 397 | 3-pyridyl | H | CH₂CH₃ | CH₂C≡CH | OCH₃ | O |

TABLE A-continued

| No. | A | R₁ | R₂ | R₃ | R₄ | X |
|---|---|---|---|---|---|---|
| 398 | 3-pyridyl | H | CH₂C≡CH | CH₃ | OCH₃ | O |
| 399 | 3-pyridyl | H | CH₂C≡CH | CH₂CH₃ | OCH₃ | O |
| 400 | 3-pyridyl | H | CH₂C≡CH | CH₂C≡CH | OCH₃ | O |
| 401 | 6-Cl-3-pyridyl | H | H | CH₂C≡CH | OCH₃ | O |
| 402 | 6-Cl-3-pyridyl | H | CH₃ | CH₂C≡CH | OCH₃ | O |
| 403 | 6-Cl-3-pyridyl | H | CH₂CH₃ | CH₂C≡CH | OCH₃ | O |
| 404 | 6-Cl-3-pyridyl | H | CH₂C≡CH | CH₃ | OCH₃ | O |
| 405 | 6-Cl-3-pyridyl | H | CH₂C≡CH | CH₂CH₃ | OCH₃ | O |
| 406 | 6-Cl-3-pyridyl | H | CH₂C≡CH | CH₂C≡CH | OCH₃ | O |
| 407 | 4-pyridyl | H | H | CH₂C≡CH | OCH₃ | O |
| 408 | 4-pyridyl | H | CH₃ | CH₂C≡CH | OCH₃ | O |
| 409 | 4-pyridyl | H | CH₂CH₃ | CH₂C≡CH | OCH₃ | O |
| 410 | 4-pyridyl | H | CH₂C≡CH | CH₃ | OCH₃ | O |
| 411 | 4-pyridyl | H | CH₂C≡CH | CH₂CH₃ | OCH₃ | O |
| 412 | 4-pyridyl | H | CH₂C≡CH | CH₂C≡CH | OCH₃ | O |

TABLE A-continued

| No. | A | R$_1$ | R$_2$ | R$_3$ | R$_4$ | X |
|---|---|---|---|---|---|---|
| 413 | pyridazin-3-yl | H | H | CH$_2$C≡CH | OCH$_3$ | O |
| 414 | pyridazin-3-yl | H | CH$_3$ | CH$_2$C≡CH | OCH$_3$ | O |
| 415 | pyridazin-3-yl | H | CH$_2$CH$_3$ | CH$_2$C≡CH | OCH$_3$ | O |
| 416 | pyridazin-3-yl | H | CH$_2$C≡CH | CH$_3$ | OCH$_3$ | O |
| 417 | pyridazin-3-yl | H | CH$_2$C≡CH | CH$_2$CH$_3$ | OCH$_3$ | O |
| 418 | pyridazin-3-yl | H | CH$_2$C≡CH | CH$_2$C≡CH | OCH$_3$ | O |
| 419 | 6-chloropyridazin-3-yl | H | H | CH$_2$C≡CH | OCH$_3$ | O |
| 420 | 6-chloropyridazin-3-yl | H | CH$_3$ | CH$_2$C≡CH | OCH$_3$ | O |
| 421 | 6-chloropyridazin-3-yl | H | CH$_2$CH$_3$ | CH$_2$C≡CH | OCH$_3$ | O |
| 422 | 6-chloropyridazin-3-yl | H | CH$_2$C≡CH | CH$_3$ | OCH$_3$ | O |
| 423 | 6-chloropyridazin-3-yl | H | CH$_2$C≡CH | CH$_2$CH$_3$ | OCH$_3$ | O |
| 424 | 6-chloropyridazin-3-yl | H | CH$_2$C≡CH | CH$_2$C≡CH | OCH$_3$ | O |
| 425 | pyrimidin-5-yl | H | H | CH$_2$C≡CH | OCH$_3$ | O |
| 426 | pyrimidin-5-yl | H | CH$_3$ | CH$_2$C≡CH | OCH$_3$ | O |
| 427 | pyrimidin-5-yl | H | CH$_2$CH$_3$ | CH$_2$C≡CH | OCH$_3$ | O |

TABLE A-continued

| No. | A | R₁ | R₂ | R₃ | R₄ | X |
|---|---|---|---|---|---|---|
| 428 | 4-pyrimidinyl | H | CH₂C≡CH | CH₃ | OCH₃ | O |
| 429 | 4-pyrimidinyl | H | CH₂C≡CH | CH₂CH₃ | OCH₃ | O |
| 430 | 4-pyrimidinyl | H | CH₂C≡CH | CH₂C≡CH | OCH₃ | O |
| 431 | 6-Cl-4-pyrimidinyl | H | H | CH₂C≡CH | OCH₃ | O |
| 432 | 6-Cl-4-pyrimidinyl | H | CH₃ | CH₂C≡CH | OCH₃ | O |
| 433 | 6-Cl-4-pyrimidinyl | H | CH₂CH₃ | CH₂C≡CH | OCH₃ | O |
| 434 | 6-Cl-4-pyrimidinyl | H | CH₂C≡CH | CH₃ | OCH₃ | O |
| 435 | 6-Cl-4-pyrimidinyl | H | CH₂C≡CH | CH₂CH₃ | OCH₃ | O |
| 436 | 6-Cl-4-pyrimidinyl | H | CH₂C≡CH | CH₂C≡CH | OCH₃ | O |
| 437 | 2-pyrimidinyl | H | H | CH₂C≡CH | OCH₃ | O |
| 438 | 2-pyrimidinyl | H | CH₃ | CH₂C≡CH | OCH₃ | O |
| 439 | 2-pyrimidinyl | H | CH₂CH₃ | CH₂C≡CH | OCH₃ | O |
| 440 | 2-pyrimidinyl | H | CH₂C≡CH | CH₃ | OCH₃ | O |
| 441 | 2-pyrimidinyl | H | CH₂C≡CH | CH₂CH₃ | OCH₃ | O |

TABLE A-continued

| No. | A | R$_1$ | R$_2$ | R$_3$ | R$_4$ | X |
|---|---|---|---|---|---|---|
| 442 | 2-pyrimidinyl | H | CH$_2$C≡CH | CH$_2$C≡CH | OCH$_3$ | O |
| 443 | 2-pyrazinyl | H | H | CH$_2$C≡CH | OCH$_3$ | O |
| 444 | 2-pyrazinyl | H | CH$_3$ | CH$_2$C≡CH | OCH$_3$ | O |
| 445 | 2-pyrazinyl | H | CH$_2$CH$_3$ | CH$_2$C≡CH | OCH$_3$ | O |
| 446 | 2-pyrazinyl | H | CH$_2$C≡CH | CH$_3$ | OCH$_3$ | O |
| 447 | 2-pyrazinyl | H | CH$_2$C≡CH | CH$_2$CH$_3$ | OCH$_3$ | O |
| 448 | 2-pyrazinyl | H | CH$_2$C≡CH | CH$_2$C≡CH | OCH$_3$ | O |
| 449 | 2-quinolinyl | H | H | CH$_2$C≡CH | OCH$_3$ | O |
| 450 | 2-quinolinyl | H | CH$_3$ | CH$_2$C≡CH | OCH$_3$ | O |
| 451 | 2-quinolinyl | H | CH$_2$CH$_3$ | CH$_2$C≡CH | OCH$_3$ | O |
| 452 | 2-quinolinyl | H | CH$_2$C≡CH | CH$_3$ | OCH$_3$ | O |
| 453 | 2-quinolinyl | H | CH$_2$C≡CH | CH$_2$CH$_3$ | OCH$_3$ | O |
| 454 | 2-quinolinyl | H | CH$_2$C≡CH | CH$_2$C≡CH | OCH$_3$ | O |

TABLE A-continued

| No. | A | R₁ | R₂ | R₃ | R₄ | X |
|---|---|---|---|---|---|---|
| 455 | 2,3-dihydro-1,4-benzodioxin-6-yl | H | H | CH₂C≡CH | OCH₃ | O |
| 456 | 2,3-dihydro-1,4-benzodioxin-6-yl | H | CH₃ | CH₂C≡CH | OCH₃ | O |
| 457 | 2,3-dihydro-1,4-benzodioxin-6-yl | H | CH₂CH₃ | CH₂C≡CH | OCH₃ | |
| 458 | 2,3-dihydro-1,4-benzodioxin-6-yl | H | CH₂C≡CH | CH₃ | OCH₃ | O |
| 459 | 2,3-dihydro-1,4-benzodioxin-6-yl | H | CH₂C≡CH | CH₂CH₃ | OCH₃ | O |
| 460 | 2,3-dihydro-1,4-benzodioxin-6-yl | H | CH₂C≡CH | CH₂C≡CH | OCH₃ | O |
| 461 | 1,3-benzodioxol-5-yl | H | H | CH₂C≡CH | OCH₃ | O |
| 462 | 1,3-benzodioxol-5-yl | H | CH₃ | CH₂C≡CH | OCH₃ | O |
| 463 | 1,3-benzodioxol-5-yl | H | CH₂CH₃ | CH₂C≡CH | OCH₃ | O |
| 464 | 1,3-benzodioxol-5-yl | H | CH₂C≡CH | CH₃ | OCH₃ | O |
| 465 | 1,3-benzodioxol-5-yl | H | CH₂C≡CH | CH₂CH₃ | OCH₃ | O |
| 466 | 1,3-benzodioxol-5-yl | H | CH₂C≡CH | CH₂C≡CH | OCH₃ | O |
| 467 | 2,3-dihydro-1-benzofuran-5-yl | H | H | CH₂C≡CH | OCH₃ | O |

TABLE A-continued

| No. | A | $R_1$ | $R_2$ | $R_3$ | $R_4$ | X |
|---|---|---|---|---|---|---|
| 468 | 2,3-dihydrobenzofuran-5-yl | H | $CH_3$ | $CH_2C\equiv CH$ | $OCH_3$ | O |
| 469 | 2,3-dihydrobenzofuran-5-yl | H | $CH_2CH_3$ | $CH_2C\equiv CH$ | $OCH_3$ | O |
| 470 | 2,3-dihydrobenzofuran-5-yl | H | $CH_2C\equiv CH$ | $CH_3$ | $OCH_3$ | O |
| 471 | 2,3-dihydrobenzofuran-5-yl | H | $CH_2C\equiv CH$ | $CH_2CH_3$ | $OCH_3$ | O |
| 472 | 2,3-dihydrobenzofuran-5-yl | H | $CH_2C\equiv CH$ | $CH_2C\equiv CH$ | $OCH_3$ | O |
| 473 | indan-5-yl | H | H | $CH_2C\equiv CH$ | $OCH_3$ | O |
| 474 | indan-5-yl | H | $CH_3$ | $CH_2C\equiv CH$ | $OCH_3$ | O |
| 475 | indan-5-yl | H | $CH_2CH_3$ | $CH_2C\equiv CH$ | $OCH_3$ | O |
| 476 | indan-5-yl | H | $CH_2C\equiv CH$ | $CH_3$ | $OCH_3$ | O |
| 477 | indan-5-yl | H | $CH_2C\equiv CH$ | $CH_2CH_3$ | $OCH_3$ | O |
| 478 | indan-5-yl | H | $CH_2C\equiv CH$ | $CH_2C\equiv CH$ | $OCH_3$ | O |
| 479 | fluoren-2-yl | H | H | $CH_2C\equiv CH$ | $OCH_3$ | O |
| 480 | fluoren-2-yl | H | $CH_3$ | $CH_2C\equiv CH$ | $OCH_3$ | O |

TABLE A-continued
| No. | A | R₁ | R₂ | R₃ | R₄ | X |
|---|---|---|---|---|---|---|
| 481 | 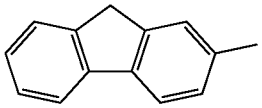 | H | CH₂CH₃ | CH₂C≡CH | OCH₃ | O |
| 482 | 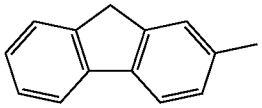 | H | CH₂C≡CH | CH₃ | OCH₃ | O |
| 483 | 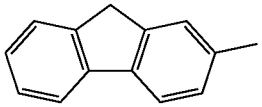 | H | CH₂C≡CH | CH₂CH₃ | OCH₃ | O |
| 484 | 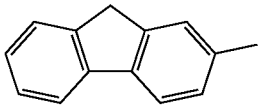 | H | CH₂C≡CH | CH₂C≡CH | OCH₃ | O |
| 485 | 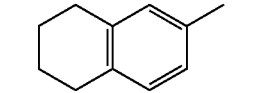 | H | H | CH₂C≡CH | OCH₃ | O |
| 486 | 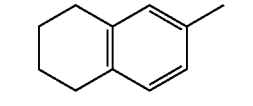 | H | CH₃ | CH₂C≡CH | OCH₃ | O |
| 487 | 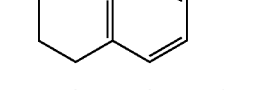 | H | CH₂CH₃ | CH₂C≡CH | OCH₃ | O |
| 488 | 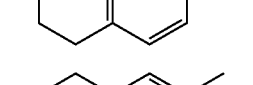 | H | CH₂C≡CH | CH₃ | OCH₃ | O |
| 489 | 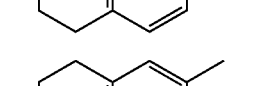 | H | CH₂C≡CH | CH₂CH₃ | OCH₃ | O |
| 490 | 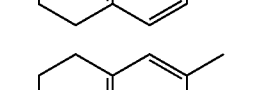 | H | CH₂C≡CH | CH₂C≡CH | OCH₃ | O |
| 491 | 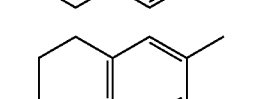 | CH₃ | CH₂C≡CH | CH₂C≡CH | OCH₃ | O |
| 492 | 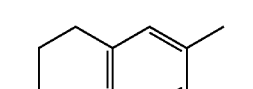 | H | CH₂C≡CH | CH₂C≡CH | CH₃ | O |
| 493 | 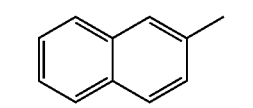 | H | CH₂C≡CH | CH₂C≡CH | OCH₃ | S |
| 494 |  | H | H | CH₂C≡CH | OCH₃ | O |

TABLE A-continued

| No. | A | R₁ | R₂ | R₃ | R₄ | X |
|---|---|---|---|---|---|---|
| 495 | 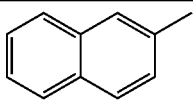 | H | CH₃ | CH₂C≡CH | OCH₃ | O |
| 496 | 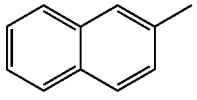 | H | CH₂CH₃ | CH₂C≡CH | OCH₃ | O |
| 497 | 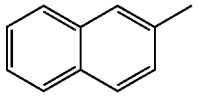 | H | CH₂C≡CH | CH₃ | OCH₃ | O |
| 498 | 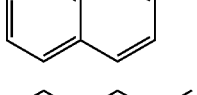 | H | CH₂C≡CH | CH₂CH₃ | OCH₃ | O |
| 499 | 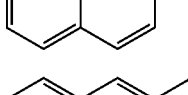 | H | CH₂C≡CH | CH₂C≡CH | OCH₃ | O |
| 500 | 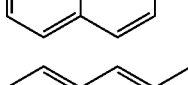 | CH₃ | CH₂C≡CH | CH₂C≡CH | OCH₃ | O |
| 5Cl | 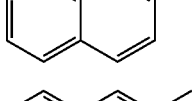 | H | CH₂C≡CH | CH₂C≡CH | CH₃ | O |
| 502 | 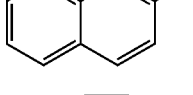 | H | CH₂C≡CH | CH₂C≡CH | OCH₃ | S |
| 503 | 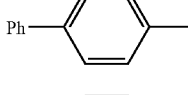 | H | H | CH₂C≡CH | OCH₃ | O |
| 504 | 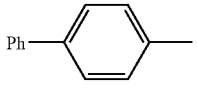 | H | CH₃ | CH₂C≡CH | OCH₃ | O |
| 505 | 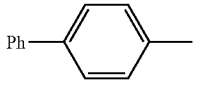 | H | CH₂CH₃ | CH₂C≡CH | OCH₃ | O |
| 506 | 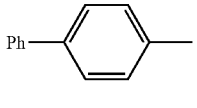 | H | CH₂C≡CH | CH₃ | OCH₃ | O |
| 507 | 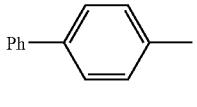 | H | CH₂C≡CH | CH₂CH₃ | OCH₃ | O |
| 508 | 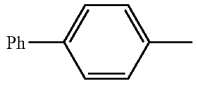 | H | CH₂C≡CH | CH₂C≡CH | OCH₃ | O |
| 509 | 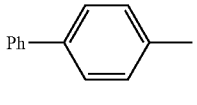 | CH₃ | CH₂C≡CH | CH₂C≡CH | OCH₃ | O |

TABLE A-continued

| No. | A | R$_1$ | R$_2$ | R$_3$ | R$_4$ | X |
|---|---|---|---|---|---|---|
| 510 | 4-Ph-C$_6$H$_4$ | H | CH$_2$C≡CH | CH$_2$C≡CH | CH$_3$ | O |
| 511 | 4-Ph-C$_6$H$_4$ | H | CH$_2$C≡CH | CH$_2$C≡CH | OCH$_3$ | S |
| 512 | Ph | H | H | CH$_3$ | Cl | O |
| 513 | Ph | H | CH$_3$ | CH$_3$ | Cl | O |
| 514 | Ph | H | CH$_2$CH$_3$ | CH$_3$ | Cl | O |
| 515 | Ph | H | CH$_2$C≡CH | CH$_3$ | Cl | O |
| 516 | Ph | H | H | CH$_2$CH$_3$ | Cl | O |
| 517 | Ph | H | CH$_3$ | CH$_2$CH$_3$ | Cl | O |
| 518 | Ph | H | CH$_2$CH$_3$ | CH$_2$CH$_3$ | Cl | O |
| 519 | Ph | H | CH$_2$C≡CH | CH$_2$CH$_3$ | Cl | O |
| 520 | Ph | H | H | CH$_2$C≡CH | Cl | O |
| 521 | Ph | H | CH$_3$ | CH$_2$C≡CH | Cl | O |
| 522 | Ph | H | CH$_2$CH$_3$ | CH$_2$C≡CH | Cl | O |
| 523 | Ph | H | CH$_2$C≡CH | CH$_2$C≡CH | Cl | O |
| 524 | 4-Cl-Ph | H | H | CH$_3$ | Cl | O |
| 525 | 4-Cl-Ph | H | CH$_3$ | CH$_3$ | Cl | O |
| 526 | 4-Cl-Ph | H | CH$_2$CH$_3$ | CH$_3$ | Cl | O |
| 527 | 4-Cl-Ph | H | CH$_2$C≡CH | CH$_3$ | Cl | O |
| 528 | 4-Cl-Ph | H | H | CH$_2$CH$_3$ | Cl | O |
| 529 | 4-Cl-Ph | H | CH$_3$ | CH$_2$CH$_3$ | Cl | O |
| 530 | 4-Cl-Ph | H | CH$_2$CH$_3$ | CH$_2$CH$_3$ | Cl | O |
| 531 | 4-Cl-Ph | H | CH$_2$C≡CH | CH$_2$CH$_3$ | Cl | O |
| 532 | 4-Cl-Ph | H | H | CH$_2$C≡CH | Cl | O |
| 533 | 4-Cl-Ph | H | CH$_3$ | CH$_2$C≡CH | Cl | O |
| 534 | 4-Cl-Ph | H | CH$_2$CH$_3$ | CH$_2$C≡CH | Cl | O |
| 535 | 4-Cl-Ph | H | CH$_2$C≡CH | CH$_2$C≡CH | Cl | O |
| 536 | 4-Cl-Ph | H | H | CH$_3$ | Br | O |
| 537 | 4-Cl-Ph | H | CH$_3$ | CH$_3$ | Br | O |
| 538 | 4-Cl-Ph | H | CH$_2$CH$_3$ | CH$_3$ | Br | O |
| 539 | 4-Cl-Ph | H | CH$_2$C≡CH | CH$_3$ | Br | O |
| 540 | 4-Cl-Ph | H | H | CH$_2$CH$_3$ | Br | O |
| 541 | 4-Cl-Ph | H | CH$_3$ | CH$_2$CH$_3$ | Br | O |
| 542 | 4-Cl-Ph | H | CH$_2$CH$_3$ | CH$_2$CH$_3$ | Br | O |
| 543 | 4-Cl-Ph | H | CH$_2$C≡CH | CH$_2$CH$_3$ | Br | O |
| 544 | 4-Cl-Ph | H | H | CH$_2$C≡CH | Br | O |
| 545 | 4-Cl-Ph | H | CH$_3$ | CH$_2$C≡CH | Br | O |
| 546 | 4-Cl-Ph | H | CH$_2$CH$_3$ | CH$_2$C≡CH | Br | O |
| 547 | 4-Cl-Ph | H | CH$_2$C≡CH | CH$_2$C≡CH | Br | O |
| 548 | 4-Cl-Ph | H | H | CH$_3$ | CN | O |
| 549 | 4-Cl-Ph | H | CH$_3$ | CH$_3$ | CN | O |
| 550 | 4-Cl-Ph | H | CH$_2$CH$_3$ | CH$_3$ | CN | O |
| 551 | 4-Cl-Ph | H | CH$_2$C≡CH | CH$_3$ | CN | O |
| 552 | 4-Cl-Ph | H | H | CH$_2$CH$_3$ | CN | O |
| 553 | 4-Cl-Ph | H | CH$_3$ | CH$_2$CH$_3$ | CN | O |
| 554 | 4-Cl-Ph | H | CH$_2$CH$_3$ | CH$_2$CH$_3$ | CN | O |
| 555 | 4-Cl-Ph | H | CH$_2$C≡CH | CH$_2$CH$_3$ | CN | O |
| 556 | 4-Cl-Ph | H | H | CH$_2$C≡CH | CN | O |
| 557 | 4-Cl-Ph | H | CH$_3$ | CH$_2$C≡CH | CN | O |
| 558 | 4-Cl-Ph | H | CH$_2$CH$_3$ | CH$_2$C≡CH | CN | O |
| 559 | 4-Cl-Ph | H | CH$_2$C≡CH | CH$_2$C≡CH | CN | O |
| 560 | Ph | H | H | CH$_2$C≡CH | Br | O |
| 561 | Ph | H | CH$_3$ | CH$_2$C≡CH | Br | O |
| 562 | Ph | H | CH$_2$CH$_3$ | CH$_2$C≡CH | Br | O |
| 563 | Ph | H | CH$_2$C≡CH | CH$_2$C≡CH | Br | O |
| 564 | Ph | H | H | CH$_2$C≡CH | CN | O |
| 565 | Ph | H | CH$_3$ | CH$_2$C≡CH | CN | O |
| 566 | Ph | H | CH$_2$CH$_3$ | CH$_2$C≡CH | CN | O |
| 567 | Ph | H | CH$_2$C≡CH | CH$_2$C≡CH | CN | O |
| 568 | 4-Br-Ph | H | H | CH$_2$C≡CH | Cl | O |
| 569 | 4-Br-Ph | H | CH$_3$ | CH$_2$C≡CH | Cl | O |
| 570 | 4-Br-Ph | H | CH$_2$CH$_3$ | CH$_2$C≡CH | Cl | O |
| 571 | 4-Br-Ph | H | CH$_2$C≡CH | CH$_2$C≡CH | Cl | O |
| 572 | 4-Br-Ph | H | H | CH$_2$C≡CH | Br | O |
| 573 | 4-Br-Ph | H | CH$_3$ | CH$_2$C≡CH | Br | O |
| 574 | 4-Br-Ph | H | CH$_2$CH$_3$ | CH$_2$C≡CH | Br | O |
| 575 | 4-Br-Ph | H | CH$_2$C≡CH | CH$_2$C≡CH | Br | O |
| 576 | 4-Br-Ph | H | H | CH$_2$C≡CH | CN | O |
| 577 | 4-Br-Ph | H | CH$_3$ | CH$_2$C≡CH | CN | O |
| 578 | 4-Br-Ph | H | CH$_2$CH$_3$ | CH$_2$C≡CH | CN | O |

TABLE A-continued

| No. | A | $R_1$ | $R_2$ | $R_3$ | $R_4$ | X |
|---|---|---|---|---|---|---|
| 579 | 4-Br-Ph | H | $CH_2C{\equiv}CH$ | $CH_2C{=}CH$ | CN | O |
| 580 | 4-$CH_3$-Ph | H | H | $CH_2C{=}CH$ | Cl | O |
| 581 | 4-$CH_3$-Ph | H | $CH_3$ | $CH_2C{=}CH$ | Cl | O |
| 582 | 4-$CH_3$-Ph | H | $CH_2CH_3$ | $CH_2C{=}CH$ | Cl | O |
| 583 | 4-$CH_3$-Ph | H | $CH_2C{=}CH$ | $CH_2C{=}CH$ | Cl | O |
| 584 | 4-$CH_3$-Ph | H | H | $CH_2C{=}CH$ | Br | O |
| 585 | 4-$CH_3$-Ph | H | $CH_3$ | $CH_2C{=}CH$ | Br | O |
| 586 | 4-$CH_3$-Ph | H | $CH_2CH_3$ | $CH_2C{=}CH$ | Br | O |
| 587 | 4-$CH_3$-Ph | H | $CH_2C{=}CH$ | $CH_2C{=}CH$ | Br | O |
| 588 | 4-$CH_3$-Ph | H | H | $CH_2C{=}CH$ | CN | O |
| 589 | 4-$CH_3$-Ph | H | $CH_3$ | $CH_2C{=}CH$ | CN | O |
| 590 | 4-$CH_3$-Ph | H | $CH_2CH_3$ | $CH_2C{=}CH$ | CN | O |
| 591 | 4-$CH_3$-Ph | H | $CH_2C{=}CH$ | $CH_2C{=}CH$ | CN | O |
| 592 | Ph | H | $CH_2C{=}CH$ | $CH_2C{=}CCH_3$ | $OCH_3$ | O |
| 593 | 4-Cl-Ph | H | $CH_2C{=}CH$ | $CH_2C{=}CCH_3$ | $OCH_3$ | O |
| 594 | 4-Br-Ph | H | $CH_2C{=}CH$ | $CH_2C{=}CCH_3$ | $OCH_3$ | O |
| 595 | 4-$CH_3$-Ph | H | $CH_2C{=}CH$ | $CH_2C{=}CCH_3$ | $OCH_3$ | O |
| 596 | Ph | H | $CH_2C{=}CH$ | $CH_2C{=}C{-}C_2H_5$ | $OCH_3$ | O |
| 597 | 4-Cl-Ph | H | $CH_2C{=}CH$ | $CH_2C{=}C{-}C_2H_5$ | $OCH_3$ | O |
| 598 | 4-Br-Ph | H | $CH_2C{=}CH$ | $CH_2C{=}C{-}C_2H_5$ | $OCH_3$ | O |
| 599 | 4-$CH_3$-Ph | H | $CH_2C{=}CH$ | $CH_2C{=}C{-}C_2H_5$ | $OCH_3$ | O |

(Ph designates phenyl)

Formulations may be prepared analogously to those described in, for example, WO 95/30651.

BIOLOGICAL EXAMPLES

D-1: Action Against *Plasmopara Viticola* on Vines a) Residual-protective Action Vine seedlings are sprayed at the 4- to 5-leaf stage with a spray mixture (0.02% active ingredient) prepared from a wettable powder formulation of the test compound. After 24 hours, the treated plants are infected with a sporangia suspension of the fungus. Fungus infestation is evaluated after incubation for 6 days at 95-100% relative humidity and +20° C.

b) Residual-curative Action

Vine seedlings are infected at the 4- to 5-leaf stage with a sporangia suspension of the fungus. After incubation for 24 hours in a humidity chamber at 95-100% relative humidity and +20° C., the infected plants are dried and sprayed with a spray mixture (0.02% active ingredient) prepared from a wettable powder formulation of the test compound. After the spray coating has dried, the treated plants are placed in the humidity chamber again. Fungus infestation is evaluated 6 days after infection.

Compounds of Tables 1 to 3 exhibit a good fungicidal action against *Plasmopara viticola* on vines. Compounds E1.03, E1.10, E1.15, E1.18 and E1.22 at 200 ppm inhibit fungal infestations in both tests D-1a) and D-1b) by 80-100%. At the same time untreated plants showed pathogen attack of 80-100%.

D-2: Action Against *Phytophthora* on Tomato Plants a) Residual-protective Action After a cultivation period of 3 weeks, tomato plants are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 5 days at 90-100% relative humidity and +20° C.

b) Systemic Action

After a cultivation period of 3 weeks, tomato plants are watered with a spray mixture (0.02% active ingredient based on the volume of the soil) prepared from a wettable powder formulation of the test compound. Care is taken that the spray mixture does not come into contact with the parts of the plants that are above the ground. After 96 hours, the treated plants are infected with a sporangia suspension of the fungus. Fungus infestation is evaluated after incubation of the infected plants for 4 days at 90-100% relative humidity and +20° C.

Compounds of Tables 1 to 3 exhibit a good fungicidal action against *Plasmopara viticola* on vines. Compounds E1.03, E1.06, E1.10, E1.15 and E1.22 at 200 ppm inhibit fungal infestations in both tests D-2a) and D-2b) by 80-100%. At the same time untreated plants showed pathogen attack of 80-100%.

D-3: Action Against *Phytophthora* on Potato Plants a) Residual-protective Action 2-3 week old potato plants (Bintje variety) are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90-100% relative humidity and +20° C.

b) Systemic Action 2-3 week old potato plants (Bintje variety) are watered with a spray mixture (0.02% active ingredient based on the volume of the soil) prepared from a wettable powder formulation of the test compound. Care is taken that the spray mixture does not come into contact with the parts of the plants that are above the ground. After 48 hours, the treated plants are infected with a sporangia suspension of the fungus. Fungus infestation is evaluated after incubation of the infected plants for 4 days at 90-100% relative humidity and +20° C.

Fungal infestation is effectively controlled with compounds of Tables 1 to 3. Compounds E1.03, E1.06, E1.10 and E1.15 at 200 ppm inhibit fungal infestations in both tests D-3a) and D-3b) by 80 to 100%. At the same time untreated plants showed pathogen attack of 80 to 100%.

What is claimed is:

1. An agrochemical composition adapted to control and protect against phytopathogenic fungi, comprising an active ingredient together with a suitable carrier, said active ingredient comprising at least one compound of the formula

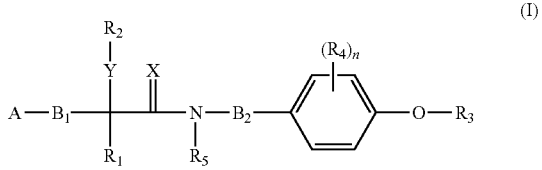

(I)

wherein:
- A stands for aryl optionally substituted by one or more substituents selected from the group consisting of $C_1$-$C_{10}$-alkyl, $C_2$-$C_{10}$-alkenyl, $C_2$-$C_{10}$-alkynyl, $C_1$-$C_8$-cycloalkyl, $C_1$-$C_8$-cycloalkyl-$C_1$-$C_{10}$-alkyl, phenyl, phenyl-$C_1$-$C_{10}$-alkyl, $C_1$-$C_{10}$-alkoxy, $C_3$-$C_{10}$-alkenyloxy, $C_3$-$C_{10}$-alkynyloxy, $C_1$-$C_{10}$-alkylthio, $C_1$-$C_{10}$-alkylsulfonyl, $C_1$-$C_{10}$-alkoxy-$C_1$-$C_{10}$-alkyl, $C_1$-$C_{10}$-alkanoyl, $C_1$-$C_{10}$-alkoxycarbonyl, $C_3$-$C_{10}$-alkenyloxycarbonyl, $C_3$-$C_{10}$-alkynyloxycarbonyl, $C_1$-$C_{10}$-alkylamino, di-$C_1$-$C_{10}$-alkylamino, hydroxy, halogen; cyano, nitro, amino and formyl radicals, wherein in turn the alkyl-, alkenyl-, alkynyl- and cycloalkyl-groups may be optionally substituted by one or more halogen atoms;
- X is oxygen or sulfur;
- Y is oxygen or sulfur;
- $R_1$ is hydrogen, $C_1$-$C_{10}$-alkyl, $C_3$-$C_{10}$-alkenyl, $C_3$-$C_{10}$-alkynyl or $C_3$-$C_8$-cycloalkyl, wherein each alkyl-, alkenyl-, alkynyl- and cycloalkyl- group may be optionally substituted by halogen;
- $R_2$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_1$-$C_6$-alkoxy-$C_1$-$C_6$-alkyl, $C_1$-$C_6$-alkoxy-$C_3$-$C_{10}$-alkenyl or $C_1$-$C_6$-alkoxy-$C_3$-$C_{10}$-alkynyl, wherein all alkyl-, alkenyl-, alkynyl-, or cycloalkyl- groups may be optionally substituted by halogen; or stands for aryl-$C_1$-$C_6$-alkyl, aryl-$C_3$-$C_{10}$-alkenyl, aryl-$C_3$-$C_{10}$-alkynyl or aryloxy-$C_1$-$C_6$-alkyl;
- $R_3$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_1$-$C_6$-alkoxy-$C_1$-$C_6$-alkyl, $C_1$-$C_6$-alkoxy-$C_3$-$C_{10}$-alkenyl or $C_1$-$C_6$-alkoxy-$C_3$-$C_{10}$-alkynyl, wherein all alkyl-, alkenyl-, alkynyl-, or cycloalkyl- groups may be optionally substituted by halogen; or is aryl-$C_1$-$C_6$-alkyl, aryl-$C_3$-$C_{10}$-alkenyl, aryl-$C_3$-$C_{10}$-alkynyl or aryloxy-$C_1$-$C_6$-alkyl;
- $R_4$ is $C_1$-$C_6$-alkyl, $C_3$-$C_6$-alkenyl, $C_3$-$C_6$-alkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-alkynyloxy, $C_1$-$C_6$-alkylthio, $C_1$-$C_6$-alkanoyl, $C_1$-$C_6$-alkylamino, di-$C_1$-$C_6$-alkylamino or $C_1$-$C_6$-alkoxycarbonyl, wherein all alkyl-, alkenyl- or alkynyl- groups may be optionally substituted by halogen; or is cyano, nitro, amino, formyl or carboxyl;
- $R_5$ is hydrogen, $C_1$-$C_6$-alkyl, $C_3$-$C_6$-alkenyl or $C_3$-$C_6$-alkynyl;
- n is an integer 0, 1, 2, 3, or 4;
- $B_1$ represents a bridge member —$CR_{10}R_{11}$—, wherein $R_{10}$ and $R_{11}$ independently of each other are hydrogen or $C_1$-$C_6$-alkyl; and
- $B_2$ is an $C_1$-$C_6$-alkylene bridge.

2. The agrochemical composition according to claim 1 wherein A is phenyl, naphthyl, 1,3-biphenyl, 1,4-biphenyl, fluorenyl, tetralinyl, indanyl, methylendioxyphenyl, (1,2-ethylene) dioxyphenyl, each optionally substituted by one or more substituents selected from the group consisting of $C_1$-$C_{10}$-alkyl, $C_2$-$C_{10}$-alkenyl, $C_2$-$C_{10}$-alkynyl, $C_1$-$C_8$-cycloalkyl, $C_1$-$C_8$-cycloalkyl-$C_1$-$C_{10}$-alkyl, phenyl, phenyl-$C_1$-$C_{10}$-alkyl, $C_1$-$C_{10}$-alkoxy, $C_3$-$C_{10}$-alkenyloxy, $C_3$-$C_{10}$-alkynyloxy, $C_1$-$C_{10}$-alkylthio, $C_1$-$C_{10}$-alkylsulfonyl, $C_1$-$C_{10}$-alkoxy-$C_1$-$C_{10}$-alkyl, $C_1$-$C_{10}$-alkanoyl, $C_1$-$C_{10}$-alkoxycarbonyl, $C_3$-$C_{10}$-alkenyloxycarbonyl, $C_3$-$C_{10}$-alkynyloxycarbonyl, $C_1$-$C_{10}$-alkylamino, di-$C_1$-$C_{10}$-alkylamino, hydroxy, halogen, cyano, nitro, amino and formyl radicals, wherein in turn the alkyl-, alkenyl-, alkynyl- and cycloalkyl-groups may be optionally substituted by one or more halogen atoms; and n is an integer from 0 to 2.

3. The agrochemical composition according to claim 1 wherein A is phenyl, naphthyl, 1,4-biphenyl, tetralinyl, indanyl, methylendioxyphenyl, (1,2-ethylene) dioxyphenyl, each optionally substituted by one, two or three substituents selected from the group consisting of $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, benzyl, $C_1$-$C_{10}$-alkoxy, $C_1$-$C_{10}$-haloalkoxy, $C_3$-$C_{10}$-alkenyloxy, $C_3$-$C_{10}$-alkynyloxy, $C_1$-$C_{10}$-alkylthio, $C_1$-$C_{10}$-haloalkylthio, $C_1$-$C_{10}$-alkylsulfonyl, $C_1$-$C_6$-alkoxy-$C_1$-$C_6$-alkyl, $C_1$-$C_{10}$-alkanoyl, $C_1$-$C_{10}$-alkoxycarbonyl, hydroxy, halogen, cyano, nitro and formyl.

4. The agrochemical composition according to claim 1 wherein A is phenyl, naphthyl, 1,4-biphenyl, tetralinyl, indanyl, methylendioxyphenyl, (1,2-ethylene) dioxyphenyl, each optionally substituted by one, two or three substituents selected from the group consisting of $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, benzyl, $C_1$-$C_{10}$-alkoxy, $C_1$-$C_{10}$-haloalkoxy, $C_3$-$C_{10}$-alkenyloxy, $C_3$-$C_{10}$-alkynyloxy, $C_1$-$C_{10}$-alkylthio, $C_1$-$C_{10}$-haloalkylthio, $C_1$-$C_{10}$-alkylsulfonyl, $C_1$-$C_6$-alkoxy-$C_1$-$C_6$-alkyl, $C_1$-$C_{10}$-alkanoyl, $C_1$-$C_{10}$-alkoxycarbonyl, hydroxy, halogen, cyano, nitro and formyl; $R_1$ is hydrogen, $C_1$-$C_{10}$-alkyl, $C_3$-$C_{10}$-alkenyl, $C_3$-$C_{10}$-alkynyl, $C_1$-$C_{10}$-haloalkyl, $C_3$-$C_{10}$-haloalkenyl or $C_3$-$C_{10}$-haloalkynyl; $R_2$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_3$-$C_8$-cycloalkyl-$C_3$-$C_6$-alkenyl, $C_3$-$C_8$-cycloalkyl-$C_3$-$C_6$-alkynyl, $C_1$-$C_6$-alkoxy-$C_1$-$C_6$-alkyl, $C_1$-$C_6$-alkoxy-$C_3$-$C_6$-alkenyl, $C_1$-$C_6$-alkoxy-$C_3$-$C_6$-alkynyl, $C_1$-$C_{10}$-haloalkyl, $C_3$-$C_{10}$-haloalkenyl, $C_3$-$C_{10}$-haloalkynyl, phenyl-$C_1$-$C_6$-alkyl, phenyl-$C_1$-$C_5$-alkenyl or phenyl-$C_1$-$C_6$-alkynyl, wherein phenyl may optionally be mono- or disubstituted by substituents selected from the group consisting of $C_1$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkanoyl, $C_1$-$C_6$-alkoxycarbonyl, halogen, cyano, nitro and formyl; $R_3$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_3$-$C_8$-cycloalkyl-$C_3$-$C_6$-alkenyl, $C_3$-$C_8$-cycloalkyl-$C_3$-$C_6$-alkynyl, $C_1$-$C_6$-alkoxy-$C_1$-$C_6$-alkyl, $C_1$-$C_6$-alkoxy-$C_3$-$C_6$-alkenyl, $C_1$-$C_6$-alkoxy-$C_3$-$C_6$-alkynyl, $C_1$-$C_{10}$-haloalkyl, $C_3$-$C_{10}$-haloalkenyl, $C_3$-$C_{10}$-haloalkynyl, phenyl-$C_1$-$C_6$-alkyl, phenyl-$C_1$-$C_6$-alkenyl or phenyl-$C_1$-$C_6$-alkynyl, wherein the phenyl groups are optionally mono- or disubstituted by radicals selected from the group consisting of $C_1$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkanoyl, $C_1$-$C_6$-alkoxycarbonyl, halogen, cyano, nitro and formyl; $R_4$ is $C_1$-$C_6$-alkyl, $C_1$-$C_6$-haloalkyl, $C_1$-$C_6$-alkoxy, $C_3$-$C_6$-alkenyloxy, $C_3$-$C_6$-alkynyloxy, $C_1$-$C_6$-alkylthio, cyano or nitro; n is an integer from 0 to 2; and $B_2$ is an alkylene bridge of the formula —CH($R_{20}$)—($CH_2$)$_p$—, wherein $R_{20}$ stands for hydrogen or $C_1$-$C_4$-alkyl and p is an integer 0, 1 or 2.

5. The agrochemical composition according to claim 1 wherein A is phenyl, naphthyl, 1,4-biphenyl, tetralinyl, indanyl, methylendioxyphenyl, each optionally substituted by one, two or three substituents selected from the group consisting of $C_1$-$C_{10}$-alkyl, $C_1$-$C_{10}$-haloalkyl, $C_2$-$C_{10}$-alkenyl, $C_2$-$C_{10}$-alkynyl, benzyl, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-haloalkylthio, $C_1$-$C_{10}$-alkanoyl, $C_1$-$C_{10}$-alkoxycarbonyl, halogen, cyano, nitro and formyl; $R_1$ is hydrogen, $C_1$-$C_8$-alkyl, $C_3$-$C_8$-alkenyl or $C_3$-$C_8$-alkynyl; $R_2$ stands for hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl, $C_1$-$C_4$-alkoxy-$C_3$-$C_4$-alkynyl, $C_1$-$C_8$-haloalkyl or $C_3$-$C_8$-haloalkynyl; $R_3$ is hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl, $C_1$-$C_4$-alkoxy-$C_3$-$C_4$-alkynyl, $C_1$-$C_8$-haloalkyl or $C_3$-$C_8$-haloalkynyl; $R_4$ is $C_1$-$C_6$-alkoxy, $C_3$-$C_6$-alkenyloxy, or $C_3$-$C_6$-alkynyloxy; $R_5$ is hydrogen or $C_1$-$C_4$ alkyl; $B_1$ stands for —$CH_2$—, —CH($CH_3$)— or —C($CH_3$)$_2$—; n is the integer 0 or 1; and $B_2$ is an alkylene-bridge of the formula —CH($R_{20}$)—($CH_2$)$_p$—, wherein $R_{20}$ stands for hydrogen or $C_1$-$C_4$-alkyl and p is an integer 0, 1 or 2.

6. The agrochemical composition according to claim 1 wherein A is phenyl optionally substituted by one or two substituents selected from the group consisting of $C_1$-$C_4$-alkyl, $C_1$-$C_4$-haloalkyl, $C_2$-$C_4$-alkenyl, $C_1$-$C_4$-alkoxy, $C_1$-$C_{10}$-alkylthio, $C_1$-$C_4$-alkanoyl, halogen and cyano; X is oxygen; Y is oxygen; $R_1$ is hydrogen, $C_1$-$C_8$-alkyl, $C_3$-$C_8$-alkenyl or $C_3$-$C_8$-alkynyl; $R_2$ is hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl or $C_1$-$C_4$-alkoxy-$C_3$-$C_4$-alkynyl; $R_3$ is hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl or $C_1$-$C_4$-alkoxy-$C_3$-$C_4$-alkynyl; $R_4$ is 3-$C_1$-$C_6$-alkoxy; $R_5$ is hydrogen or methyl; $B_1$ is selected from —$CH_2$—, —CH($CH_3$)— and —C($CH_3$)$_2$—; n is the integer 0 or 1; and $B_2$ is —$CH_2$—$CH_2$—, —$CH_2$—, —CH($CH_3$)—$CH_2$— or —CH($CH_3$)—.

7. The agrochemical composition according to claim 1, wherein A is phenyl, optionally substituted by one or two substituents selected from the group consisting of $C_1$-$C_4$-alkyl, $C_1$-$C_4$-haloalkyl, halogen and cyano; X and Y are both oxygen; $R_1$ is hydrogen; $R_2$ is hydrogen, $C_1$-$C_4$-alkyl, $C_3$-$C_4$-alkenyl or $C_3$-$C_4$-alkynyl; $R_3$ is $C_1$-$C_4$-alkyl, $C_3$-$C_4$-alkenyl or $C_3$-$C_4$-alkynyl; $R_4$ is 3-methoxy or 3-ethoxy; $R_5$ is hydrogen; $B_1$ is selected from —$CH_2$—, —CH($CH_3$)— and —C($CH_3$)$_2$—; n is the integer 1; and $B_2$ is —$CH_2$—$CH_2$—.

8. A process for the preparation of at least one compound of formula I

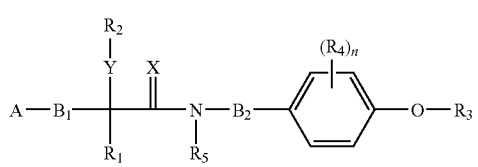

(I)

wherein:

A is aryl optionally substituted by one or more substituents selected from the group consisting of $C_1$-$C_{10}$-alkyl, $C_2$-$C_{10}$-alkenyl, $C_2$-$C_{10}$-alkynyl, $C_1$-$C_8$-cycloalkyl, $C_1$-$C_8$-cycloalkyl -$C_1$-$C_{10}$-alkyl, phenyl, phenyl-$C_1$-$C_{10}$-alkyl, $C_1$-$C_{10}$-alkoxy, $C_3$-$C_{10}$-alkenyloxy, $C_3$-$C_{10}$-alkynyloxy, $C_1$-$C_{10}$-alkylthio, $C_1$-$C_{10}$-alkylsulfonyl, $C_1$-$C_{10}$-alkoxy-$C_1$-$C_{10}$-alkyl, $C_1$-$C_{10}$-alkanoyl, $C_1$-$C_{10}$-alkoxycarbonyl, $C_3$-$C_{10}$-alkenyloxycarbonyl, $C_3$-$C_{10}$-alkynyloxycarbonyl, $C_1$-$C_{10}$-alkylamino, di-$C_1$-$C_{10}$-alkylamino, hydroxy, halogen, cyano, nitro, amino and formyl radicals, wherein in turn the alkyl-, alkenyl-, alkynyl- and cycloalkyl-groups may be optionally substituted by one or more halogen atoms;

X is oxygen or sulfur;

Y is oxygen or sulfur;

$R_1$ is hydrogen, $C_1$-$C_{10}$-alkyl, $C_3$-$C_{10}$-alkenyl, $C_3$-$C_{10}$-alkynyl or $C_3$-$C_8$-cycloalkyl, wherein each alkyl-, alkenyl-, alkynyl- and cycloalkyl- group may be optionally substituted by halogen;

$R_2$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_1$-$C_6$-alkoxy-$C_1$-$C_6$-alkyl, $C_1$-$C_6$-alkoxy-$C_3$-$C_{10}$-alkenyl or $C_1$-$C_6$-alkoxy-$C_3$-$C_{10}$-alkynyl, wherein all alkyl-, alkenyl-, alkynyl-, or cycloalkyl-groups may be optionally substituted by halogen; or stands for aryl-$C_1$-$C_6$-alkyl, aryl-$C_3$-$C_{10}$-alkenyl, aryl-$C_3$-$C_{10}$-alkynyl or aryloxy-$C_1$-$C_6$-alkyl;

$R_3$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_1$-$C_6$-alkoxy-$C_1$-$C_6$-alkyl, $C_1$-$C_6$-alkoxy-$C_3$-$C_{10}$-alkenyl or $C_1$-$C_6$-alkoxy-$C_3$-$C_{10}$-alkynyl, wherein all alkyl-, alkenyl-, alkynyl-, or cycloalkyl-groups may be optionally substituted by halogen; or is aryl-$C_1$-$C_6$-alkyl, aryl-$C_3$-$C_{10}$-alkenyl, aryl-$C_3$-$C_{10}$-alkynyl or aryloxy-$C_1$-$C_6$-alkyl;

$R_4$ is $C_1$-$C_6$-alkyl, $C_3$-$C_6$-alkenyl, $C_3$-$C_6$-alkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-alkynyloxy, $C_1$-$C_6$-alkylthio, $C_1$-$C_6$-alkanoyl, $C_1$-$C_6$-alkylamino, di-$C_1$-$C_6$-alkylamino or $C_1$-$C_6$-alkoxycarbonyl, wherein all alkyl-, alkenyl- or alkynyl-groups may be optionally substituted by halogen; or is halogen, cyano, nitro, amino, formyl or carboxyl;

$R_5$ is hydrogen, $C_1$-$C_6$-alkyl, $C_3$-$C_6$-alkenyl or $C_3$-$C_6$-alkynyl;

n is an integer 0, 1, 2, 3, or 4;

$B_1$ represents a bridge member —$CR_{10}R_{11}$—, wherein $R_{10}$ and $R_{11}$ independently of each other are hydrogen or $C_1$-$C_6$-alkyl; and $B_2$ is an $C_1$-$C_6$-alkylene-bridge;

which comprises a) reacting the phenol of formula VI

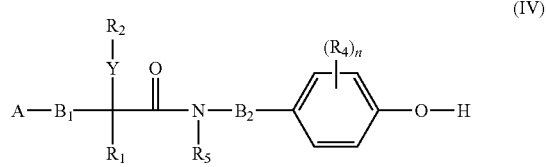

(IV)

wherein A, $R_1$, $R_2$, $R_4$, $R_5$, $B_1$, $B_2$ and n are as defined for formula I with a compound of formula V

Z-$R_3$ (V)

wherein $R_3$ is as defined for formula I and wherein Z is a leaving group yielding the subgroup IA

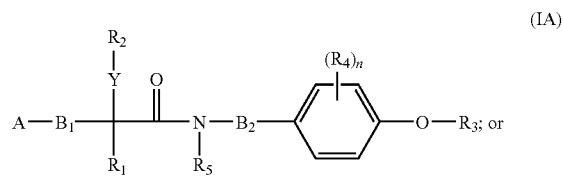

(IA)

b) reacting the acid of formula II

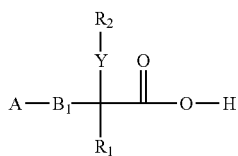

with an amine of formula VII

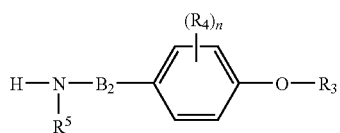

wherein A, $R_1$, $R_2$, $R_3$, $R_4$, $R_5$, $B_1$, $B_2$ and n are as defined for formula I, or c) reacting the compound of formula XIV

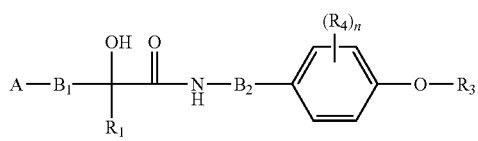

with an etherifying agent of formula XV $$Z-R_2 \quad (XV)$$

wherein A, $R_1$, $R_2$, $R_3$, $R_4$, $R_5$, $B_1$, $B_2$ and n are as defined for formula I and wherein Z is a leaving group; fielding the subgroup IB

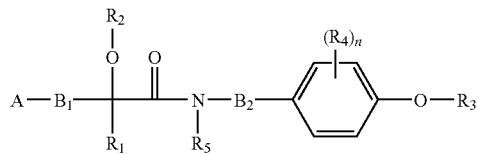

and optionally converting the amide function of the compound of subgroup IA into a thioamide function as in the subgroup IC

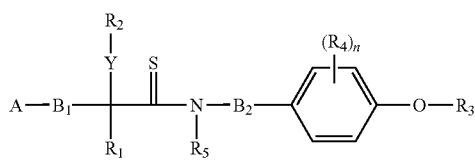

by treatment with a sulfurating agent.

9. A method of controlling an infestation of crop plants by phytopathogenic fungi, which comprises the application of at least one compound of formula I as an active ingredient to the plant, to parts of plants or to the locus thereof, said at least one compound of formula I being:

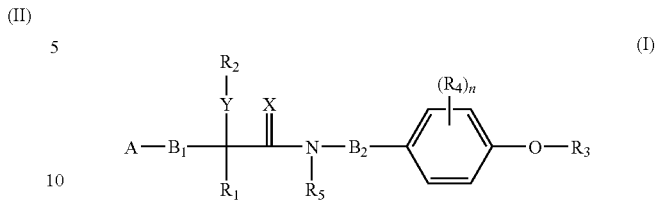

wherein:

A is aryl optionally substituted by one or more substituents selected from the group consisting of $C_1$-$C_{10}$-alkyl, $C_2$-$C_{10}$-alkenyl, $C_2$-$C_{10}$-alkynyl, $C_1$-$C_8$-cycloalkyl, $C_1$-$C_8$-cycloalkyl-$C_1$-$C_{10}$-alkyl, phenyl, phenyl-$C_1$-$C_{10}$-alkyl, $C_1$-$C_{10}$-alkoxy, $C_3$-$C_{10}$-alkenyloxy, $C_3$-$C_{10}$-alkynyloxy, $C_1$-$C_{10}$-alkylthio, $C_1$-$C_{10}$-alkylsulfonyl, $C_1$-$C_{10}$-alkoxy-$C_1$-$C_{10}$-alkyl, $C_1$-$C_{10}$-alkanoyl, $C_1$-$C_{10}$-alkoxycarbonyl, $C_3$-$C_{10}$-alkenyloxycarbonyl, $C_3$-$C_{10}$-alkynyloxycarbonyl, $C_1$-$C_{10}$-alkylamino, di-$C_1$-$C_{10}$-alkylamino, hydroxy, halogen, cyano, nitro, amino and formyl radicals, wherein in turn the alkyl-, alkenyl-, alkynyl- and cycloalkyl-groups may be optionally substituted by one or more halogen atoms;

X is oxygen or sulfur;

Y is oxygen or sulfur;

$R_1$ is hydrogen, $C_1$-$C_{10}$-alkyl, $C_3$-$C_{10}$-alkenyl, $C_3$-$C_{10}$-alkynyl or $C_3$-$C_8$-cycloalkyl, wherein each alkyl-, alkenyl-, alkynyl- and cycloalkyl- group may be optionally substituted by halogen;

$R_2$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_1$-$C_6$-alkoxy-$C_1$-$C_6$-alkyl, $C_1$-$C_6$-alkoxy-$C_3$-$C_{10}$-alkenyl or $C_1$-$C_6$-alkoxy-$C_3$-$C_{10}$-alkynyl, wherein all alkyl-, alkenyl-, alkynyl-, or cycloalkyl-groups may be optionally substituted by halogen; or stands for aryl-$C_1$-$C_6$-alkyl, aryl-$C_3$-$C_{10}$-alkenyl, aryl-$C_3$-$C_{10}$-alkynyl or aryloxy-$C_1$-$C_6$-alkyl;

$R_3$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_1$-$C_6$-alkoxy-$C_1$-$C_6$-alkyl, $C_1$-$C_6$-alkoxy-$C_3$-$C_{10}$-alkenyl or $C_1$-$C_6$-alkoxy-$C_3$-$C_{10}$-alkynyl, wherein all alkyl-, alkenyl-, alkynyl-, or cycloalkyl-groups may be optionally substituted by halogen; or is aryl-$C_1$-$C_6$-alkyl, aryl-$C_3$-$C_{10}$-alkenyl, aryl-$C_3$-$C_{10}$-alkynyl or aryloxy-$C_1$-$C_6$-alkyl;

$R_4$ is $C_1$-$C_6$-alkyl, $C_3$-$C_6$-alkenyl, $C_3$-$C_6$-alkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-alkynyloxy, $C_1$-$C_6$-alkylthio, $C_1$-$C_6$-alkanoyl, $C_1$-$C_6$-alkylamino, di-$C_1$-$C_6$-alkylamino or $C_1$-$C_6$-alkoxycarbonyl, wherein all alkyl-, alkenyl- or alkynyl-groups may be optionally substituted by halogen; or is halogen, cyano, nitro, amino, formyl or carboxyl;

$R_5$ is hydrogen, $C_1$-$C_6$-alkyl, $C_3$-$C_6$-alkenyl or $C_3$-$C_6$-alkynyl;

n is an integer 0, 1, 2, 3, or 4;

$B_1$ represents a bridge member —$CR_{10}R_{11}$—, wherein $R_{10}$ and $R_{11}$ independently of each other are hydrogen or $C_1$-$C_6$-alkyl; and $B_2$ is an $C_1$-$C_6$-alkylene bridge.

10. A compound of the formula

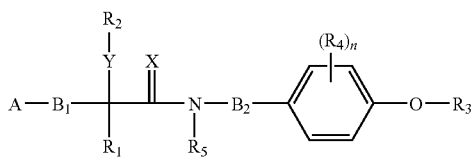

(I)

wherein:
A stands for aryl optionally substituted by one or more substituents selected from the group consisting of $C_1$-$C_{10}$-alkyl, $C_2$-$C_{10}$-alkenyl, $C_2$-$C_{10}$-alkynyl, $C_1$-$C_8$-cycloalkyl, $C_1$-$C_8$-cycloalkyl-$C_1$-$C_{10}$-alkyl, phenyl, phenyl-$C_1$-$C_{10}$-alkyl, $C_1$-$C_{10}$-alkoxy, $C_3$-$C_{10}$-alkenyloxy, $C_3$-$C_{10}$-alkynyloxy, $C_1$-$C_{10}$-alkylthio, $C_1$-$C_{10}$-alkylsulfonyl, $C_1$-$C_{10}$-alkoxy-$C_1$-$C_{10}$-alkyl, $C_1$-$C_{10}$-alkanoyl, $C_1$-$C_{10}$-alkoxycarbonyl, $C_3$-$C_{10}$-alkenyloxycarbonyl, $C_3$-$C_{10}$-alkynyloxycarbonyl, $C_1$-$C_{10}$-alkylamino, di-$C_1$-$C_{10}$-alkylamino, hydroxy, halogen, cyano, nitro, amino and formyl radicals, wherein in turn the alkyl-, alkenyl-, alkynyl- and cycloalkyl-groups may be optionally substituted by one or more halogen atoms;

X is oxygen or sulfur;

Y is oxygen or sulfur;

$R_1$ is hydrogen, $C_1$-$C_{10}$-alkyl, $C_3$-$C_{10}$-alkenyl, $C_3$-$C_{10}$-alkynyl or $C_3$-$C_8$-cycloalkyl, wherein each alkyl-, alkenyl-, alkynyl- and cycloalkyl- group may be optionally substituted by halogen;

$R_2$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_1$-$C_6$-alkoxy-$C_1$-$C_6$-alkyl, $C_1$-$C_6$-alkoxy-$C_3$-$C_{10}$-alkenyl or $C_1$-$C_6$-alkoxy-$C_3$-$C_{10}$-alkynyl, wherein all alkyl-, alkenyl-, alkynyl-, or cycloalkyl-groups may be optionally substituted by halogen; or stands for aryl-$C_1$-$C_6$-alkyl, aryl-$C_3$-$C_{10}$-alkenyl, aryl-$C_3$-$C_{10}$-alkynyl or aryloxy-$C_1$-$C_6$-alkyl;

$R_3$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_1$-$C_6$-alkoxy-$C_1$-$C_6$-alkyl, $C_1$-$C_6$-alkoxy-$C_3$-$C_{10}$-alkenyl or $C_1$-$C_6$-alkoxy-$C_3$-$C_{10}$-alkynyl, wherein all alkyl-, alkenyl-, alkynyl-, or cycloalkyl- groups may be optionally substituted by halogen; or is aryl-$C_1$-$C_6$-alkyl, aryl-$C_3$-$C_{10}$-alkenyl, aryl-$C_3$-$C_{10}$-alkynyl or aryloxy-$C_1$-$C_6$-alkyl;

$R_4$ is $C_1$-$C_6$-alkyl, $C_3$-$C_6$-alkenyl, $C_3$-$C_6$-alkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-alkynyloxy, $C_1$-$C_6$-alkylthio, $C_1$-$C_6$-alkanoyl, $C_1$-$C_6$-alkylamino, di-$C_1$-$C_6$-alkylamino or $C_1$-$C_6$-alkoxycarbonyl, wherein all alkyl-, alkenyl- or alkynyl- groups may be optionally substituted by halogen; or is halogen, cyano, nitro, amino, formyl or carboxyl;

$R_5$ is hydrogen, $C_1$-$C_6$-alkyl, $C_3$-$C_6$-alkenyl or $C_3$-$C_6$-alkynyl;

n is an integer 0, 1, 2, 3, or 4;

$B_1$ represents a bridge member —$CR_{10}R_{11}$—, wherein $R_{10}$ and $R_{11}$ independently of each other are hydrogen or $C_1$-$C_6$-alkyl; and $B_2$ is an $C_1$-$C_6$-alkylene-bridge; with the exception of the compounds 2-hydroxy-N-[2-(3-bromo-4-hydroxy-phenyl)-ethyl]-3-(3-bromo-4-hydroxy-phenyl)-propionamide, 2-hydroxy-N-[2-(3-bromo-4-methoxy-phenyl)-ethyl]-3-(3-bromo-4-methoxy-phenyl)-propionamide, 2-hydroxy-N-[2-(3-bromo-4-methoxy-phenyl)-ethyl]-3-(3,5-dibromo-4-hydroxy-phenyl)-propionamide, 2-hydroxy-N-[2-(3-bromo-4-hydroxy-phenyl)-ethyl]-3-(3,5-dibromo-4-hydroxy-phenyl)-propionamide, 2-hydroxy-N-[2-(3,5-dibromo-4-hydroxy-phenyl)-ethyl]-3-(3-bromo-4-hydroxy-phenyl)-propionamide, 2-hydroxy-N-[2-(3,5-dibromo-4-methoxy-phenyl)-ethyl]-3-(3-bromo-4-methoxy-phenyl)-propionamide, and 2-hydroxy-N-[2-(3-bromo-4-methoxy-phenyl)-ethyl]-3-(3,5-dibromo-4-methoxy-phenyl)-propionamide.

11. A compound according to claim 10 wherein A is phenyl, naphthyl, 1,3-biphenyl, 1,4-biphenyl, fluorenyl, tetralinyl, indanyl, methylendioxyphenyl, (1,2-ethylene) dioxyphenyl, each optionally substituted by one or more substituents selected from the group consisting of $C_1$-$C_{10}$-alkyl, $C_2$-$C_{10}$-alkenyl, $C_2$-$C_{10}$-alkynyl, $C_1$-$C_8$-cycloalkyl, $C_1$-$C_8$-cycloalkyl-$C_1$-$C_{10}$-alkyl, phenyl, phenyl-$C_1$-$C_{10}$-alkyl, $C_1$-$C_{10}$-alkoxy, $C_3$-$C_{10}$-alkenyloxy, $C_3$-$C_{10}$-alkynyloxy, $C_1$-$C_{10}$-alkylthio, $C_1$-$C_{10}$-alkylsulfonyl, $C_1$-$C_{10}$-alkoxy-$C_1$-$C_{10}$-alkyl, $C_1$-$C_{10}$-alkanoyl, $C_1$-$C_{10}$-alkoxycarbonyl, $C_3$-$C_{10}$-alkenyloxycarbonyl, $C_3$-$C_{10}$-alkynyloxycarbonyl, $C_1$-$C_{10}$-alkylamino, di-$C_1$-$C_{10}$-alkylamino, hydroxy, halogen, cyano, nitro, amino and formyl radicals, wherein in turn the alkyl-, alkenyl-, alkynyl- and cycloalkyl-groups may be optionally substituted by one or more halogen atoms; and n is an integer from 0 to 2.

12. A compound according to claim 10 wherein A is phenyl, naphthyl, 1,4-biphenyl, tetralinyl, indanyl, methylendioxyphenyl, (1,2-ethylene) dioxyphenyl, each optionally substituted by one, two or three substituents selected from the group consisting of $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, benzyl, $C_1$-$C_{10}$-alkoxy, $C_1$-$C_{10}$-haloalkoxy, $C_3$-$C_{10}$-alkenyloxy, $C_3$-$C_{10}$-alkynyloxy, $C_1$-$C_{10}$-alkylthio, $C_1$-$C_{10}$-haloalkylthio, $C_1$-$C_{10}$-alkylsulfonyl, $C_1$-$C_6$-alkoxy-$C_1$-$C_6$-alkyl, $C_1$-$C_{10}$-alkanoyl, $C_1$-$C_{10}$-alkoxycarbonyl, hydroxy, halogen, cyano, nitro and formyl.

13. A compound according to claim 10 wherein A is phenyl, naphthyl, 1,4-biphenyl, tetralinyl, indanyl, methylendioxyphenyl, (1,2-ethylene) dioxyphenyl, each optionally substituted by one, two or three substituents selected from the group consisting of $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, benzyl, $C_1$-$C_{10}$-alkoxy, $C_1$-$C_{10}$-haloalkoxy, $C_3$-$C_{10}$-alkenyloxy, $C_3$-$C_{10}$-alkynyloxy, $C_1$-$C_{10}$-alkylthio, $C_1$-$C_{10}$-haloalkylthio, $C_1$-$C_{10}$-alkylsulfonyl, $C_1$-$C_6$-alkoxy-$C_1$-$C_6$-alkyl, $C_1$-$C_{10}$-alkanoyl, $C_1$-$C_{10}$-alkoxycarbonyl, hydroxy, halogen, cyano, nitro and formyl; $R_1$ is hydrogen, $C_1$-$C_{10}$-alkyl, $C_3$-$C_{10}$-alkenyl, $C_3$-$C_{10}$-alkynyl, $C_1$-$C_{10}$-haloalkyl, $C_3$-$C_{10}$-haloalkenyl or $C_3$-$C_{10}$-haloalkynyl; $R_2$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_3$-$C_8$-cycloalkyl-$C_3$-$C_6$-alkenyl, $C_3$-$C_8$-cycloalkyl-$C_3$-$C_6$-alkynyl, $C_1$-$C_6$-alkoxy-$C_1$-$C_6$-alkyl, $C_1$-$C_6$-alkoxy-$C_3$-$C_6$-alkenyl, $C_1$-$C_6$-alkoxy-$C_3$-$C_6$-alkynyl, $C_1$-$C_{10}$-haloalkyl, $C_3$-$C_{10}$-haloalkenyl, $C_3$-$C_{10}$-haloalkynyl, phenyl-$C_1$-$C_6$-alkyl, phenyl-$C_1$-$C_5$-alkenyl or phenyl-$C_1$-$C_6$-alkynyl, wherein phenyl may optionally be mono- or disubstituted by substituents selected from the group consisting of $C_1$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkanoyl, $C_1$-$C_6$-alkoxycarbonyl, halogen, cyano, nitro and formyl; $R_3$ is hydrogen, $C_1$-$C_{10}$-alkyl, $C_3$-$C_{10}$-alkenyl, $C_3$-$C_{10}$-alkynyl, $C_3$-$C_8$-cycloalkyl, $C_3$-$C_8$-cycloalkyl-$C_1$-$C_6$-alkyl, $C_3$-$C_8$-cycloalkyl-$C_3$-$C_6$-alkenyl, $C_3$-$C_8$-cycloalkyl-$C_3$-$C_6$-alkynyl, $C_1$-$C_6$-alkoxy-$C_1$-$C_6$-alkyl, $C_1$-$C_6$-alkoxy-$C_3$-$C_6$-alkenyl, $C_1$-$C_6$- alkoxy-$C_3$-$C_6$-alkynyl, $C_1$-$C_{10}$-haloalkyl, $C_3$-$C_{10}$-haloalkenyl, $C_3$-$C_{10}$-haloalkynyl, phenyl-$C_1$-$C_6$-alkyl, phenyl-$C_1$-$C_6$-alkenyl or phenyl-$C_1$-$C_6$-alkynyl, wherein the phenyl groups are optionally mono- or disubstituted by radicals selected from the group consisting of $C_1$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkanoyl, $C_1$-$C_6$-alkoxycarbonyl, halogen, cyano, nitro and formyl; $R_4$ is $C_1$-$C_6$-alkyl, $C_1$-$C_6$-haloalkyl, $C_1$-$C_6$-alkoxy, $C_3$-$C_6$-alkenyloxy, $C_3$-$C_6$-alkynyloxy, $C_1$-$C_6$-alkylthio, halogen, cyano or nitro; n is an integer from 0 to 2; and $B_2$ is an alkylene-bridge of the formula —CH($R_{20}$)—($CH_2$)$_p$—, wherein $R_{20}$ stands for hydrogen or $C_1$-$C_4$-alkyl and p is an integer 0, 1 or 2.

14. A compound according to claim 10 wherein A is phenyl, naphthyl, 1,4-biphenyl, tetralinyl, indanyl, methylenedioxyphenyl, each optionally substituted by one, two or three substituents selected from the group consisting of $C_1$-$C_{10}$-alkyl, $C_1$-$C_{10}$-haloalkyl, $C_2$-$C_{10}$-alkenyl, $C_2$-$C_{10}$-alkynyl, benzyl, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-haloalkylthio, $C_1$-$C_{10}$-alkanoyl, $C_1$-$C_{10}$-alkoxycarbonyl, halogen, cyano, nitro and formyl; $R_1$ is hydrogen, $C_1$-$C_8$-alkyl, $C_3$-$C_8$-alkenyl or $C_3$-$C_8$-alkynyl; $R_2$ stands for hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl, $C_1$-$C_4$-alkoxy-$C_3$-$C_4$-alkynyl, $C_1$-$C_8$-haloalkyl or $C_3$-$C_8$-haloalkynyl; $R_3$ is hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl, $C_1$-$C_4$-alkoxy-$C_3$-$C_4$-alkynyl, $C_1$-$C_8$-haloalkyl or $C_3$-$C_8$-haloalkynyl; $R_4$ is $C_1$-$C_6$-alkoxy, $C_3$-$C_6$-alkenyloxy, $C_3$-$C_6$-alkynyloxy or halogen; $R_5$ is hydrogen or $C_1$-$C_4$ alkyl; $B_1$ stands for —$CH_2$—, —CH($CH_3$)— or —C($CH_3$)$_2$—; n is the integer 0 or 1; and $B_2$ is an alkylene-bridge of the formula —CH($R_{20}$)—($CH_2$)$_p$—, wherein $R_{20}$ stands for hydrogen or $C_1$-$C_4$-alkyl and p is an integer 0, 1 or 2.

15. A compound according to claim 10 wherein A is phenyl optionally substituted by one or two substituents selected from the group consisting of $C_1$-$C_4$-alkyl, $C_1$-$C_4$-haloalkyl, $C_2$-$C_4$-alkenyl, $C_1$-$C_4$-alkoxy, $C_1$-$C_{10}$-alkylthio, $C_1$-$C_4$-alkanoyl, halogen, and cyano; X is oxygen; Y is oxygen; $R_1$ is hydrogen, $C_1$-$C_8$-alkyl, $C_3$-$C_8$-alkenyl or $C_3$-$C_8$-alkynyl; $R_2$ is hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl or $C_1$-$C_4$-alkoxy-$C_3$-$C_4$-alkynyl; $R_3$ is hydrogen, $C_1$-$C_8$-alkyl, $C_3$-$C_8$-alkenyl, $C_3$-$C_8$-alkynyl, $C_3$-$C_6$-cycloalkyl-$C_3$-$C_4$-alkynyl or $C_1$-$C_4$-alkoxy-$C_3$-$C_4$-alkynyl; $R_4$ is 3-$C_1$-$C_6$-alkoxy; $R_5$ is hydrogen or methyl; $B_1$ is selected from —$CH_2$—, —CH($CH_3$)— and —C($CH_3$)$_2$—; n is the integer 0 or 1; and $B_2$ is —$CH_2$—$CH_2$—, —$CH_2$—, —CH($CH_3$)—$CH_2$— or —CH($CH_3$)—.

16. A compound according to claim 10, wherein A is phenyl, optionally substituted by one or two substituents selected from the group consisting of $C_1$-$C_4$-alkyl, $C_1$-$C_4$-haloalkyl, halogen and cyano; X and Y are both oxygen; $R_1$ is hydrogen; $R_2$ is hydrogen, $C_1$-$C_4$-alkyl, $C_3$-$C_4$-alkenyl or $C_3$-$C_4$-alkynyl; $R_3$ is $C_1$-$C_4$-alkyl, $C_3$-$C_4$-alkenyl or $C_3$-$C_4$-alkynyl; $R_4$ is 3-methoxy or 3-ethoxy; $R_5$ is hydrogen; $B_1$ is selected from —$CH_2$—, —CH($CH_3$)— and —C($CH_3$)$_2$—; n is the integer 1; and $B_2$ is —$CH_2$—$CH_2$—.

17. A compound according to claim 10 selected from the group consisting of:

2-hydroxy-N-[2-(3-methoxy-4-prop-2-ynyloxy-phenyl)-ethyl]-3-phenyl-propionamide, 2-ethoxy-N-[2-(3-methoxy-4-prop-2-ynyloxy-phenyl)-ethyl]-3-phenyl-propionamide, N-[2-(3-methoxy-4-prop-2-ynyloxy-phenyl)-ethyl]-3-phenyl-2-prop-2-ynyloxy-propionamide, 3-(4-chloro-phenyl)-N-[2-(3-methoxy-4-prop-2-ynyloxy-phenyl)-ethyl]-2-prop-2-ynyloxy-propionamide, 3-(4-chloro-phenyl)-2-methoxy-N-[2-(3-methoxy-4-prop-2-ynyloxy-phenyl)-ethyl]-propionamide, 3-(4-chloro-phenyl)-2-hydroxy-N-[2-(3-methoxy-4-prop-2-ynyloxy-phenyl)-ethyl]-propionamide, 3-(4-fluoro-phenyl)-2-hydroxy-N-[2-(3-methoxy-4-prop-2-ynyloxy-phenyl)-ethyl]-propionamide, 2-ethoxy-3-(4-fluoro-phenyl)-N-[2-(3-methoxy-4-prop-2-ynyloxy-phenyl)-ethyl]-propionamide, 3-(4-fluoro-phenyl)-N-[2-(3-methoxy-4-prop-2-ynyloxy-phenyl)-ethyl]-2-prop-2-ynyloxypropionamide, 3-(4-bromo-phenyl)-2-hydroxy-N-[2-(3-methoxy-4-prop-2-ynyloxy-phenyl)-ethyl]-propionamide, 3-(4-bromo-phenyl)-N-[2-(3-methoxy-4-prop-2-ynyloxy-phenyl)-ethyl]-2-prop-2-ynyloxy-propionamide, 3-(4-bromo-phenyl)-2-methoxy-N-[2-(3-methoxy-4-prop-2-ynyloxy-phenyl)-ethyl]-propionamide, 3-(4-bromo-phenyl)-2-ethoxy-N-[2-(3-methoxy-4-prop-2-ynyloxy-phenyl)-ethyl]-propionamide, N-[2-(3-methoxy-4-prop-2-ynyloxy-phenyl)-ethyl]-2-prop-2-ynyloxy-3-p-tolyl-propionamide, 3-(4-ethyl-phenyl)-N-[2-(3-methoxy-4-prop-2-ynyloxy-phenyl)-ethyl]-2-prop-2-ynyloxy-propionamide, 2-ethoxy-3-(4-ethyl-phenyl)-N-[2-(3-methoxy-4-prop-2-ynyloxy-phenyl)-ethyl]-propionamide, (R)-2-hydroxy-N-[2-(3-methoxy-4-prop-2-ynyloxy-phenyl)-ethyl]-3-phenyl-propionamide, (R)-2-ethoxy-N-[2-(3-methoxy-4-prop-2-ynyloxy-phenyl)-ethyl]-3-phenyl-propionamide, (R)-N-[2-(3-methoxy-4-prop-2-ynyloxy-phenyl)-ethyl]-3-phenyl-2-prop-2-ynyloxy-propionamide, (R)-3-(4-chloro-phenyl)-N-[2-(3-methoxy-4-prop-2-ynyloxy-phenyl)-ethyl]-2-prop-2-ynyloxy-propionamide, (R)-3-(4-chloro-phenyl)-2-methoxy-N-[2-(3-methoxy-4-prop-2-ynyloxy-phenyl)-ethyl]-propionamide, (R)-3-(4-chloro-phenyl)-2-hydroxy-N-[2-(3-methoxy-4-prop-2-ynyloxy-phenyl)-ethyl]-propionamide, (R)-3-(4-fluoro-phenyl)-2-hydroxy-N-[2-(3-methoxy-4-prop-2-ynyloxy-phenyl)-ethyl]-propionamide, (R)-2-ethoxy-3-(4-fluoro-phenyl)-N-[2-(3-methoxy-4-prop-2-ynyloxy-phenyl)-ethyl]-propionamide, (R)-3-(4-fluoro-phenyl)-N-[2-(3-methoxy-4-prop-2-ynyloxy-phenyl)-ethyl]-2-prop-2-ynyloxy-propionamide, (R)-3-(4-bromo-phenyl)-2-hydroxy-N-[2-(3-methoxy-4-prop-2-ynyloxy-phenyl)-ethyl]-propionamide, (R)-3-(4-bromo-phenyl)-N-[2-(3-methoxy-4-prop-2-ynyloxy-phenyl)-ethyl]-2-prop-2-ynyloxy-propionamide, (R)-3-(4-bromo-phenyl)-2-methoxy-N-[2-(3-methoxy-4-prop-2-ynyloxy-phenyl)-ethyl]-propionamide, (R)-3-(4-bromo-phenyl)-2-ethoxy-N-[2-(3-methoxy-4-prop-2-ynyloxy-phenyl)-ethyl]-propionamide, (R)-N-[2-(3-methoxy-4-prop-2-ynyloxy-phenyl)-ethyl]-2-prop-2-ynyloxy-3-p-tolyl-propionamide, (R)-3-(4-ethyl-phenyl)-N-[2-(3-methoxy-4-prop-2-ynyloxy-phenyl)-ethyl]-2-prop-2-ynyloxy-propionamide, (R)-2-ethoxy-3-(4-ethyl-phenyl)-N-[2-(3-methoxy-4-prop-2-ynyloxy-phenyl)-ethyl]-propionamide, (S)-2-hydroxy-N-[2-(3-methoxy-4-prop-2-ynyloxy-phenyl)-ethyl]-3-phenyl-propionamide, (S)-2-ethoxy-N-[2-(3-methoxy-4-prop-2-ynyloxy-phenyl)-ethyl]-3-phenyl-propionamide, (S)-N-[2-(3-methoxy-4-prop-2-ynyloxy-phenyl)-ethyl]-3-phenyl-2-prop-2-ynyloxy-propionamide, (S)-3-(4-chloro-phenyl)-N-[2-(3-methoxy-4-prop-2-ynyloxy-phenyl)-ethyl]-2-prop-2-ynyloxy-propionamide, (S)-3-(4-chloro-phenyl)-2-methoxy-N-[2-(3-methoxy-4-prop-2-ynyloxy-phenyl)-ethyl]-propionamide,
(S)-3-(4-chloro-phenyl)-2-hydroxy-N-[2-(3-methoxy-4-prop-2-ynyloxy-phenyl)-ethyl]-propionamide,
(S)-3-(4-fluoro-phenyl)-2-hydroxy-N-[2-(3-methoxy-4-prop-2-ynyloxy-phenyl)-ethyl]-propionamide,
(S)-2-ethoxy-3-(4-fluoro-phenyl)-N-[2-(3-methoxy-4-prop-2-ynyloxy-phenyl)-ethyl]-propionamide,
(S)-3-(4-fluoro-phenyl)-N-[2-(3-methoxy-4-prop-2-ynyloxy-phenyl)-ethyl]-2-prop-2-ynyloxy-propionamide,
(S)-3-(4-bromo-phenyl)-2-hydroxy-N-[2-(3-methoxy-4-prop-2-ynyloxy-phenyl)-ethyl]-propionamide,
(S)-3-(4-bromo-phenyl)-N-[2-(3-methoxy-4-prop-2-ynyloxy-phenyl)-ethyl]-2-prop-2-ynyloxy-propionamide,
(S)-3-(4-bromo-phenyl)-2-methoxy-N-[2-(3-methoxy-4-prop-2-ynyloxy-phenyl)-ethyl]-propionamide,
(S)-3-(4-bromo-phenyl)-2-ethoxy-N-[2-(3-methoxy-4-prop-2-ynyloxy-phenyl)-ethyl]-propionamide,
(S)-N-[2-(3-methoxy-4-prop-2-ynyloxy-phenyl)-ethyl]-2-prop-2-ynyloxy-3-p-tolyl-propionamide,
(S)-3-(4-ethyl-phenyl)-N-[2-(3-methoxy-4-prop-2-ynyloxy-phenyl)-ethyl]-2-prop-2-ynyloxy-propionamide, and
(S)-2-ethoxy-3-(4-ethyl-phenyl)-N-[2-(3-methoxy-4-prop-2-ynyloxy-phenyl)-ethyl]-propionamide.

18. An agrochemical composition adapted to control and protect against phytopathogenic fungi, comprising as an active ingredient the compound of claim 10, together with a suitable carrier.

19. An agrochemical composition adapted to control and protect against phytopathogenic fungi, comprising as an active ingredient the compound of claim 11, together with a suitable carrier.

20. An agrochemical composition adapted to control and protect against phytopathogenic fungi, comprising as an active ingredient the compound of claim 17, together with a suitable carrier.

* * * * *